US011459573B2

(12) United States Patent
Chan et al.

(10) Patent No.: US 11,459,573 B2
(45) Date of Patent: Oct. 4, 2022

(54) DEADMAN AND PASSCODE MICROBIAL KILL SWITCHES

(71) Applicant: TRUSTEES OF BOSTON UNIVERSITY, Boston, MA (US)

(72) Inventors: Tsz Yan Clement Chan, Quincy, MA (US); James J. Collins, Newton, MA (US); Jeong Wook Lee, Brighton, MA (US); Douglas Ewen Cameron, Brookline, MA (US)

(73) Assignee: TRUSTEES OF BOSTON UNIVERSITY, Boston, MA (US)

(*) Notice: Subject to any disclaimer, the term of this patent is extended or adjusted under 35 U.S.C. 154(b) by 441 days.

(21) Appl. No.: 15/764,752

(22) PCT Filed: Sep. 30, 2016

(86) PCT No.: PCT/US2016/054767
§ 371 (c)(1),
(2) Date: Mar. 29, 2018

(87) PCT Pub. No.: WO2017/059245
PCT Pub. Date: Apr. 6, 2017

(65) Prior Publication Data
US 2019/0040398 A1 Feb. 7, 2019

Related U.S. Application Data

(60) Provisional application No. 62/235,186, filed on Sep. 30, 2015.

(51) Int. Cl.
C12N 5/00 (2006.01)
C12N 15/70 (2006.01)
C12N 15/63 (2006.01)
G06N 3/12 (2006.01)

(52) U.S. Cl.
CPC .......... *C12N 15/70* (2013.01); *C12N 15/635* (2013.01); *G06N 3/123* (2013.01)

(58) Field of Classification Search
CPC ....... C12N 15/70; C12N 15/635; G06N 3/123
See application file for complete search history.

(56) References Cited

U.S. PATENT DOCUMENTS

| 8,653,007 | B2 | 2/2014 | Zheng et al. |
| 8,679,745 | B2 | 3/2014 | Ballhause et al. |
| 8,822,146 | B2 | 9/2014 | Klimasauskas et al. |
| 8,889,352 | B2 | 11/2014 | Klimasauskas et al. |
| 8,951,736 | B2 | 2/2015 | Schmidt |
| 8,962,246 | B2 | 2/2015 | Ballhause et al. |
| 8,969,061 | B2 | 3/2015 | Zhu et al. |
| 9,029,087 | B2 | 5/2015 | Zheng et al. |
| 9,034,597 | B2 | 5/2015 | Bitinaite et al. |
| 9,040,239 | B2 | 5/2015 | Zheng et al. |
| 9,121,061 | B2 | 9/2015 | Vaisvila et al. |
| 9,145,580 | B2 | 9/2015 | Feehery et al. |
| 9,150,918 | B2 | 10/2015 | Turner et al. |
| 9,175,338 | B2 | 11/2015 | Flusberg et al. |
| 9,175,341 | B2 | 11/2015 | Flusberg et al. |
| 9,200,260 | B2 | 12/2015 | Correa et al. |
| 9,200,316 | B2 | 12/2015 | Zheng et al. |
| 9,238,836 | B2 | 1/2016 | Korlach et al. |
| 9,243,233 | B2 | 1/2016 | Rim et al. |
| 9,267,117 | B2 | 2/2016 | Guan et al. |
| 9,464,277 | B2 | 10/2016 | Zheng et al. |
| 9,347,093 | B2 | 11/2016 | Klimasauskas et al. |
| 9,505,797 | B2 | 11/2016 | Klimasauskas et al. |
| 9,546,400 | B2 | 1/2017 | Turner et al. |
| 9,567,633 | B2 | 2/2017 | Gao et al. |
| 9,611,510 | B2 | 4/2017 | He et al. |
| 9,650,675 | B2 | 5/2017 | Rimseliene et al. |
| 9,677,128 | B2 | 6/2017 | Robertson et al. |
| 9,879,315 | B2 | 1/2018 | Summerer et al. |
| 9,915,655 | B2 | 3/2018 | Bensimon et al. |
| 9,988,673 | B2 | 6/2018 | Klimasauskas et al. |
| 10,081,827 | B2 | 9/2018 | Guan et al. |

(Continued)

FOREIGN PATENT DOCUMENTS

| EP | 1568786 A2 | 8/2005 |
| EP | 2376632 A1 | 10/2011 |

(Continued)

OTHER PUBLICATIONS

Chan et al. "Deadman" and "Passcode microbial kill switches for bacterial containment" (Nat Chem Biol. Feb. 2016; vol. 12, No. 2: pp. 82-86). (Year: 2016).*
Office Action issued during the proseuction of U.S. Appl. No. 15/725,917; dated May 14, 2019.
Notice of Corrected Allowability during the prosecution of U.S. Appl. No. 15/440,815; dated May 15, 2019.
Requirement for Restriction issued during the prosecution of U.S. Appl. No. 15/483,297.
Chun-Xiao Song et al., "The hunt for 5-hydroxymethylcytosine: the sixth base", Epigenomics, vo. 3, No. 5, 521-523, Oct. 2011.
European Search Report dated Oct. 10, 2018 for EP Application No. 18174572.

(Continued)

Primary Examiner — Catherine S Hibbert
(74) Attorney, Agent, or Firm — Nixon Peabody LLP; Ronald I. Eisenstein; Mark J. Fitzgerald

(57) ABSTRACT

Provided herein are systems, methods and compositions for rendering cells or the expression of an effector protein sensitive to a predetermined condition. In one aspect, cells can be rendered dependent upon the presence of an environmental agent, e.g., an exogenous agent, without which the cell will default to expression of a death protein and be killed. In another aspect, cells can be rendered sensitive to the presence of a set of predetermined conditions such that cells will only grow when two or more necessary exogenous agents are supplied, and without either of which, the cells are killed. In this aspect, hybrid transcription factors provide a vast array of possible predetermined conditions.

2 Claims, 46 Drawing Sheets
Specification includes a Sequence Listing.

(56) References Cited

U.S. PATENT DOCUMENTS

| | | |
|---|---|---|
| 10,155,939 B1 | 12/2018 | Vaisvila et al. |
| 2004/0048279 A1 | 3/2004 | Olek et al. |
| 2004/0175826 A1 | 9/2004 | Maor |
| 2006/0257905 A1 | 11/2006 | Freije et al. |
| 2007/0026393 A1 | 2/2007 | Berlin et al. |
| 2007/0269824 A1 | 11/2007 | Albrecht et al. |
| 2010/0167942 A1 | 7/2010 | Zheng et al. |
| 2010/0175141 A1* | 7/2010 | Collins .................. A61P 43/00 800/13 |
| 2010/0197510 A1 | 8/2010 | Spain et al. |
| 2011/0059432 A1 | 3/2011 | Ballhause et al. |
| 2011/0172826 A1 | 7/2011 | Amodei et al. |
| 2012/0064521 A1 | 3/2012 | Yen et al. |
| 2013/0009799 A1 | 1/2013 | Collins et al. |
| 2013/0109568 A1 | 5/2013 | Hyde et al. |
| 2013/0230856 A1 | 9/2013 | Schneider et al. |
| 2014/0178873 A1 | 6/2014 | Brachmann et al. |
| 2014/0179564 A1 | 6/2014 | Korlach et al. |
| 2014/0272970 A1 | 9/2014 | Zegzouti et al. |
| 2015/0004596 A1 | 1/2015 | Zhu et al. |
| 2015/0011403 A1 | 1/2015 | Lo et al. |
| 2015/0240310 A1 | 8/2015 | Bitinaite et al. |
| 2015/0285807 A1 | 10/2015 | Shi et al. |
| 2015/0307542 A1 | 10/2015 | Roy et al. |
| 2016/0046981 A1 | 2/2016 | Correa et al. |
| 2016/0115525 A1 | 4/2016 | Ebenstein et al. |
| 2016/0194696 A1 | 7/2016 | Guan et al. |
| 2016/0304552 A1 | 10/2016 | Roy et al. |
| 2017/0051354 A1 | 2/2017 | Davis et al. |
| 2017/0067093 A1 | 3/2017 | Klimasauskas et al. |
| 2017/0175129 A1 | 6/2017 | Roy et al. |
| 2017/0198344 A1 | 7/2017 | Vaisvila et al. |
| 2017/0253924 A1 | 9/2017 | Lu et al. |
| 2017/0283863 A1 | 10/2017 | Robertson et al. |
| 2017/0283870 A1 | 10/2017 | Ost et al. |
| 2017/0298422 A1 | 10/2017 | Song et al. |
| 2018/0105884 A1 | 4/2018 | Lo et al. |
| 2018/0112206 A1 | 4/2018 | Forsyth et al. |
| 2018/0171397 A1 | 6/2018 | Vaisvila et al. |
| 2018/0201993 A1 | 7/2018 | Turner et al. |
| 2018/0223332 A1 | 8/2018 | Ost et al. |
| 2018/0237839 A1 | 8/2018 | Rao et al. |
| 2018/0245128 A1 | 8/2018 | He et al. |
| 2018/0251815 A1 | 9/2018 | Okamoto et al. |
| 2018/0258149 A1 | 9/2018 | Motz et al. |
| 2018/0258474 A1 | 9/2018 | Jain et al. |
| 2018/0312914 A1 | 11/2018 | Vaisvila et al. |
| 2018/0327855 A1 | 11/2018 | Ebenstein et al. |
| 2019/0017109 A1 | 1/2019 | Song et al. |

FOREIGN PATENT DOCUMENTS

| | | |
|---|---|---|
| EP | 2414527 A1 | 2/2012 |
| EP | 2414528 A1 | 2/2012 |
| EP | 2470675 A1 | 7/2012 |
| EP | 2630257 A1 | 8/2013 |
| EP | 2694686 A2 | 2/2014 |
| EP | 2776575 A1 | 9/2014 |
| EP | 2825645 A2 | 1/2015 |
| EP | 2945774 A1 | 2/2015 |
| EP | 3013979 A1 | 5/2016 |
| EP | 3053585 A1 | 8/2016 |
| EP | 3124605 A1 | 2/2017 |
| EP | 3214183 A1 | 6/2017 |
| WO | 2006109300 A1 | 10/2006 |
| WO | 2008150853 A1 | 12/2008 |
| WO | 2009092035 A2 | 7/2009 |
| WO | 2010075441 A1 | 7/2010 |
| WO | 2011066541 A2 | 6/2011 |
| WO | 2011066541 A3 | 10/2011 |
| WO | 2012170436 A1 | 12/2012 |
| WO | 2014027351 A1 | 2/2014 |
| WO | 2014093852 A1 | 6/2014 |
| WO | 2018129120 A1 | 7/2018 |
| WO | 2018165459 A1 | 9/2018 |

OTHER PUBLICATIONS

Saori Takahashi et al., "A novel method to analyze 5-hydroxymethylcytosine in CpG sequences using maintenance DNA methyltransferase, DNMT1", FEBS Open Bio, vol. 5, No. 1, 741-747, Jan. 1, 2015.

Office Action issued during the prosecution of U.S. Appl. No. 15/722,202; dated May 2, 2019.

Jusiak et al. "Synthetic Gene Circuits," Reviews in Cell Biology and Molecular Medicine, Oct. 20, 2014 (Oct. 20, 2014), pp. 1-56.

KOBAYASHI et al. "Programmable Cells: Interfacing Natural and Engineered Gene Networks," Proceedings of the National Academy of Sciences of the United States of America, Jun. 1, 2004 (Jun. 1, 2004), vol. 101, pp. 8414-8419.

Marchisio et al. "Synthetic Biosensing Systems," The International Journal of /Biochemistry & Cell Biology, Mar. 31, 2011 (Mar. 31, 2011), vol. 43, pp. 310-319.

Hasty et al., "Engineered gene circuits" Nature 420: 224-230 (2002).

Lee et al., "Creating Single-Copy Genetic Circuits", Molecular Cell 63, 329-336 (2016).

Brophy et al., "Principles of genetic circuit design", Nature Methods 11(5) 508-520 (2014).

Chan et al., "'Deadman' and 'Passcode' microbial kill switches for bacterial containment", Nature Chemical Biology 12: 82-86 (2016).

Stanton et al., "Genomic mining of prokaryotic repressors for orthogonal logic gates", Nature Chemical Biology 10 99-105 (2014).

* cited by examiner

| Toggle | RBS | LacI | TetR | TetR / LacI |
| --- | --- | --- | --- | --- |
| 1 | L2-T1 | 42.84 ± 0.76 | 4.60 ± 0.10 | 0.11 |
| 2 | L2-T2 | 42.84 ± 0.76 | 145.04 ± 4.53 | 3.38 |
| 3 | L3-T3 | 68.9 ± 2.67 | 268.82 ± 4.76 | 3.90 |
| 4 | L2-T3 | 42.84 ± 0.76 | 268.82 ± 4.76 | 6.27 |
| 5 | L1-T3 | 5.96 ± 0.44 | 268.82 ± 4.76 | 45.10 |

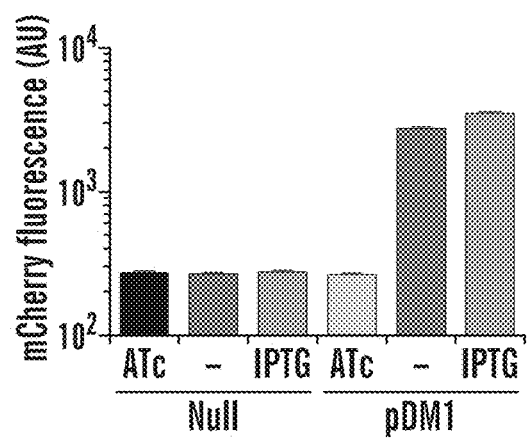
FIG. 8A
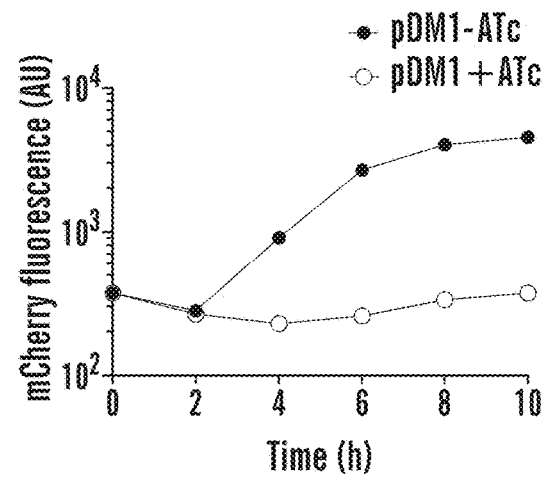
FIG. 8B
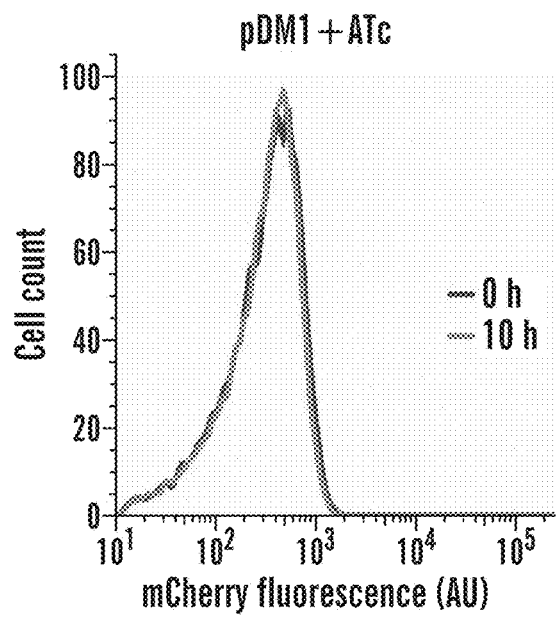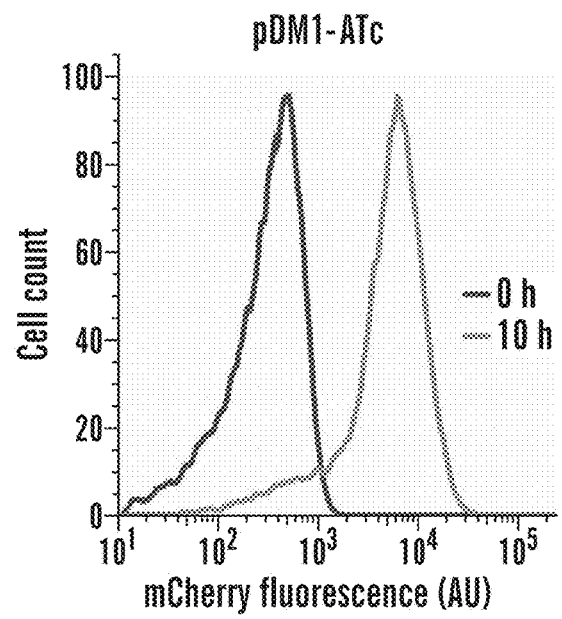
FIG. 8C

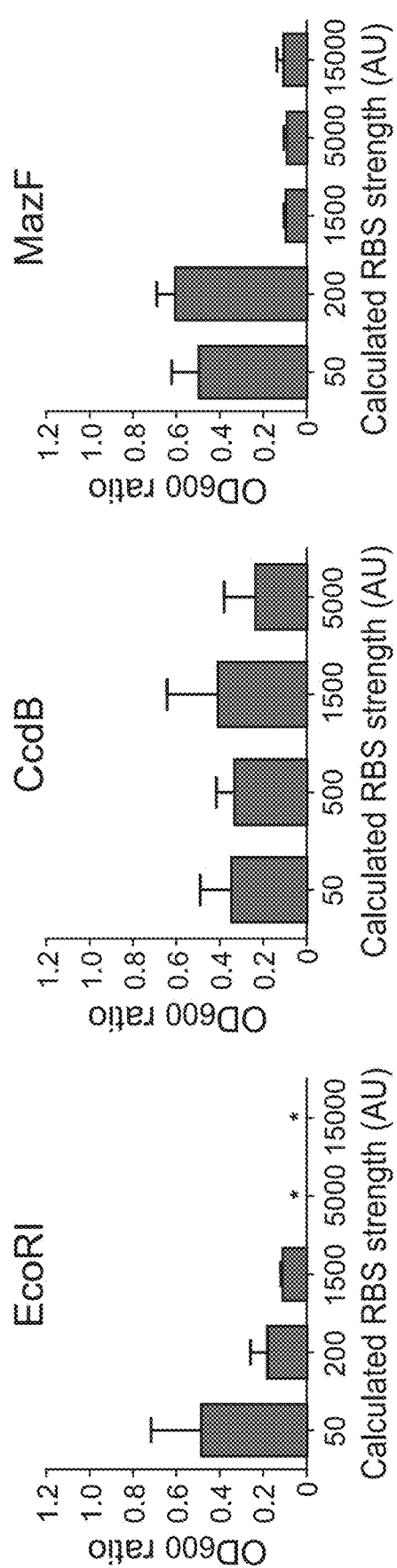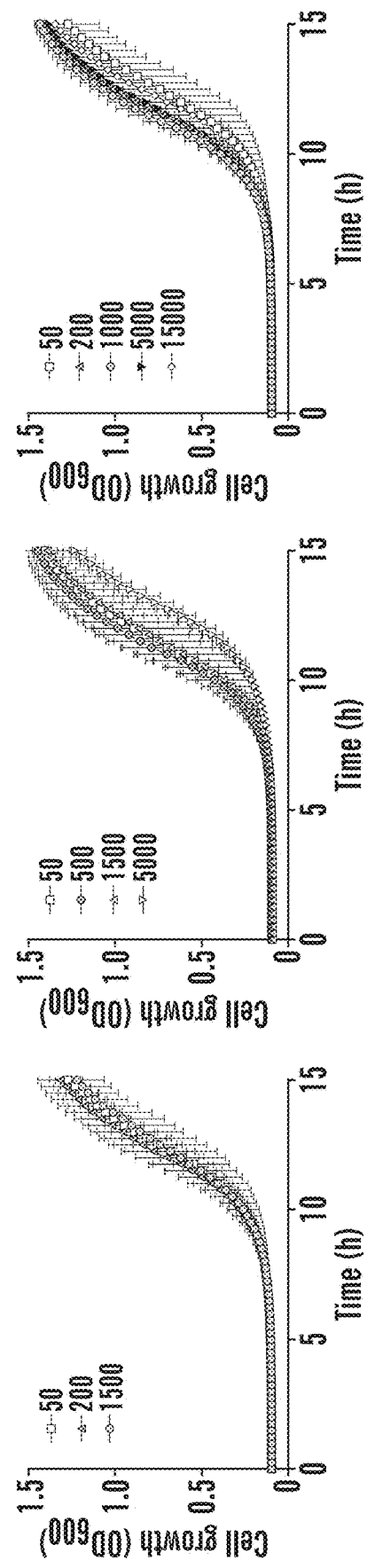
FIG. 11A
FIG. 11B

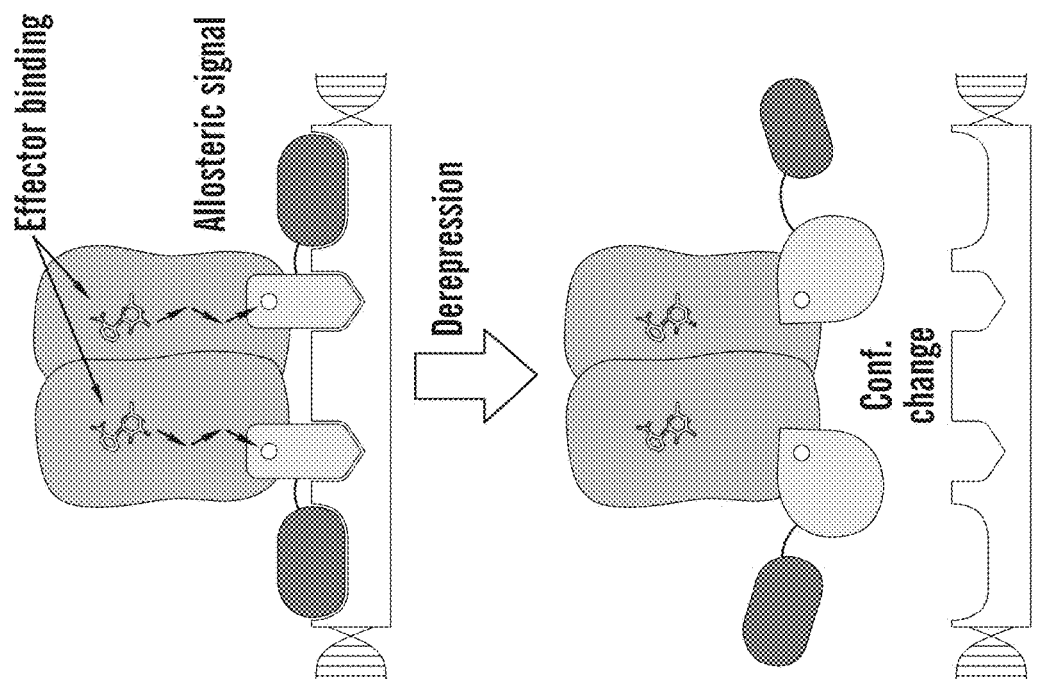
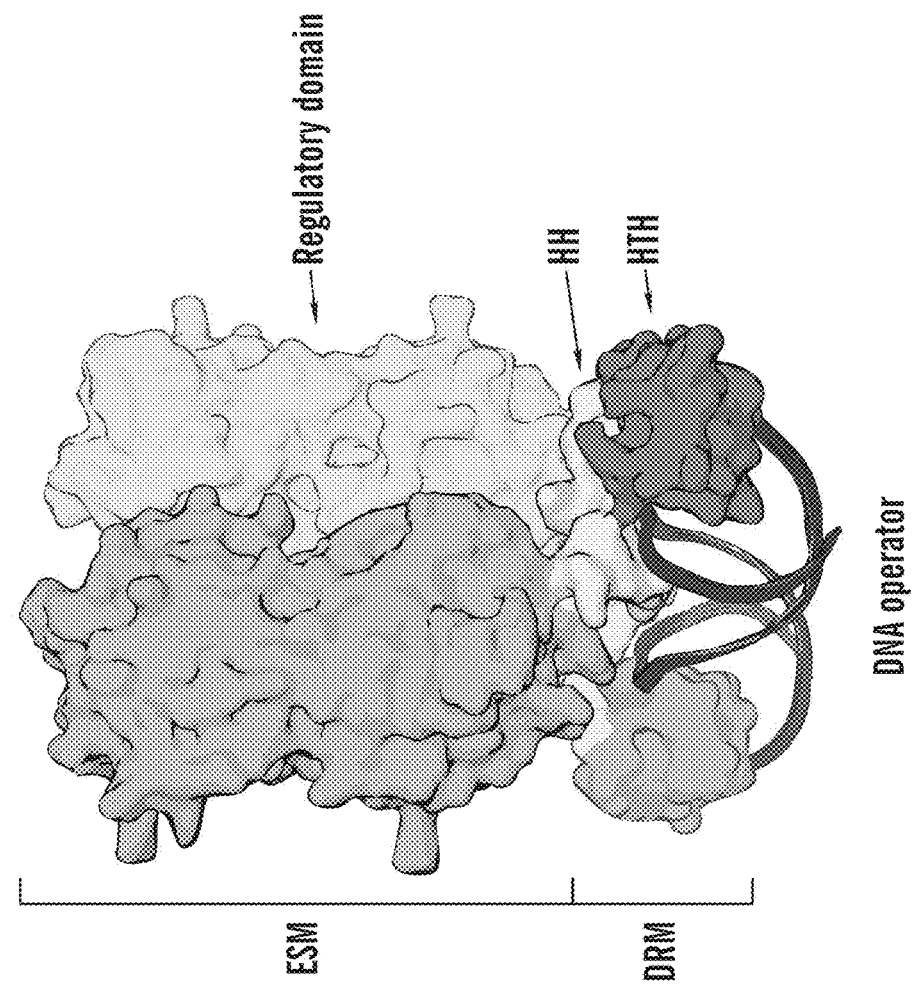
FIG. 12

FIG. 13

|  | HTH (LacI 1-45) | HH (LacI 46-60) | Regulatory domain (LacI 61-360) |
|---|---|---|---|
| LacI    | ---MKPVTLYDVAEYAGVSYQTVSRVVNQAS---- | -HVSAKTREKVEAAMAELNYIPNRVAQLAGKQSLLIGVATSS... |
| GalR    | -------MATIKDVARLAGVSVATVSRVINNSP--- | ----KASEASRLAVHSAMESLSYHPNANARALAQQTTETVGLVVGD... |
| PurR    | -------MATIKDVAKRANVSTTTVSHVINKTR--- | ----FVAEETRNAVWAAIKELHYSPSAVARSLKVNHTKSIGLLATS... |
| ScrR-K  | -MKTKRVTIKDIAELAGVSKATASLVLNGRGKELRVAQETRERVLAIAREQHYQPSIHARSLRDNRSHTIGLVVPE... |
| CelR    | MERRRRPTLEMVAALAGVGRGTVSRVINGSD----QVSPATREAVKRAIKELGYVPNRAARTLVTRRTDTVALVVSE... |
| GalS    | --------MITIRDVARQAGVSVATVSRVLNNST----LVSADTREAVMKAVSELDYRPNANAQALATQVSDTIGVVVMD... |
| AscG    | ------MMTTMLEVAKRAGVSKATVSRVLSGNG----YVSQETKDRVFQAVEESGYRPNLLARNLSAKSTQTLGLVVTN... |
| RbsR    | -------MATMKDVARLAGVSTSTVSHVINKDR----FVSEAITAKVEAALIKELNYAPSALARSLKLNQTHTIGMLITA... |
| ScrR-V  | -------MASLHDVARLAGVSKSTVSRVINDEY----GVKEATKQKVRQAVAECGYVPNQVAKDLIKSQKTNLVGIVIPR... |
| GntR    | --MKKKRPVLQDVADRVGVTKMTVSRFLRNPE----QVSVALRGKIAAALDELGYIPNRAPDILSNATSRAIGVLLPS... |
| MalI    | MATAKKITIHDVALAAGVSVSTTVSLVLSGKG----RISTATGERVNAATEELGFVRNRQASALRGGQSGVIGLIVRD... |

DRM (LacI 1-41) ▲ Module boundary ESM (LacI 42-360)

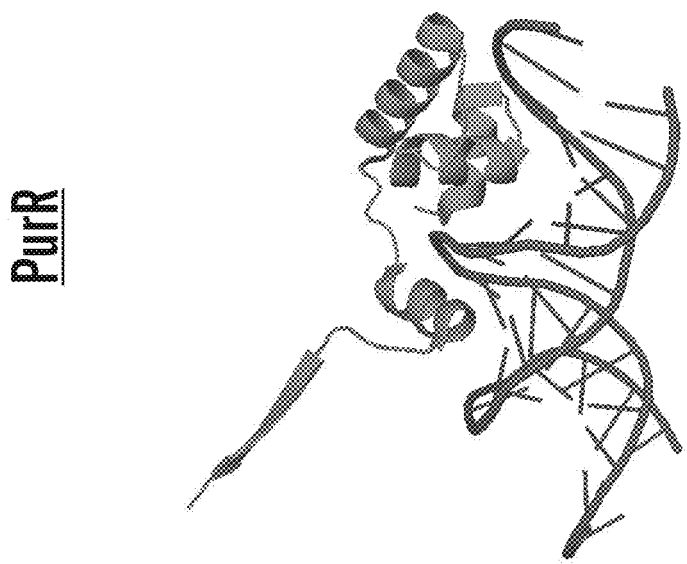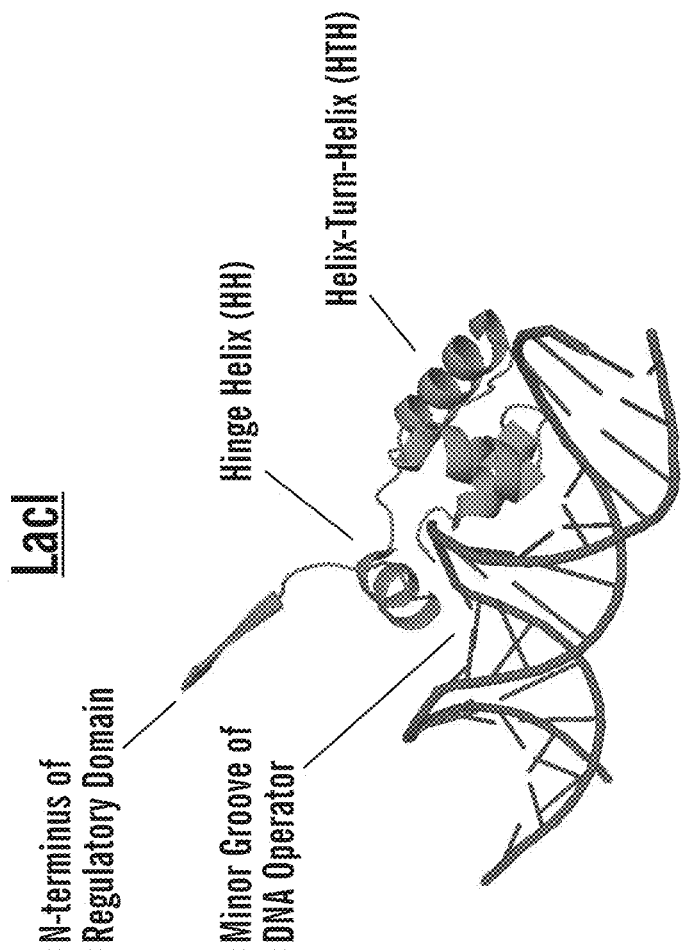
FIG. 14

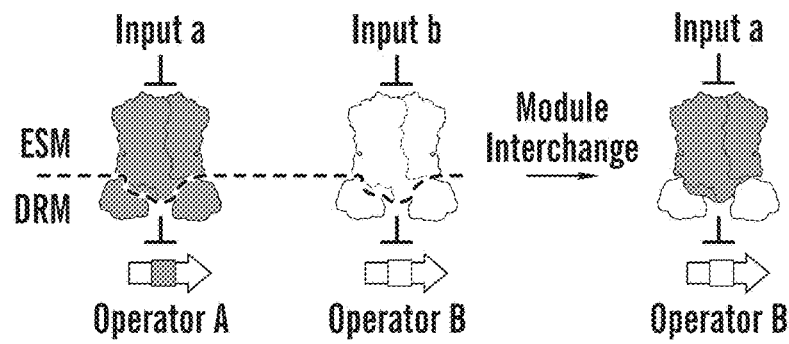
FIG. 16A
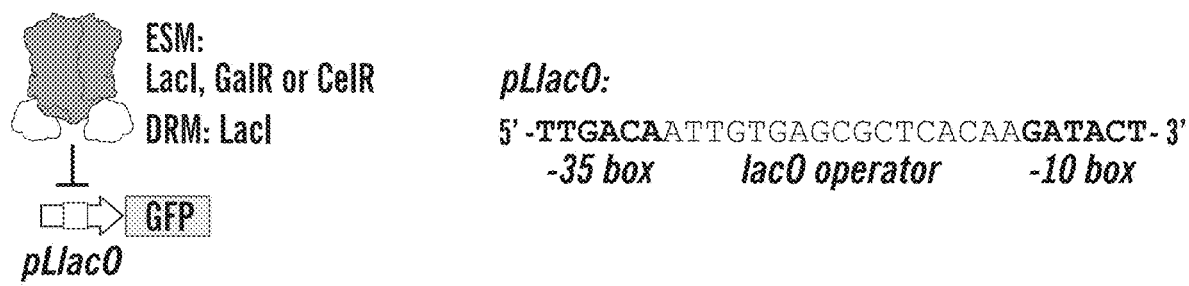
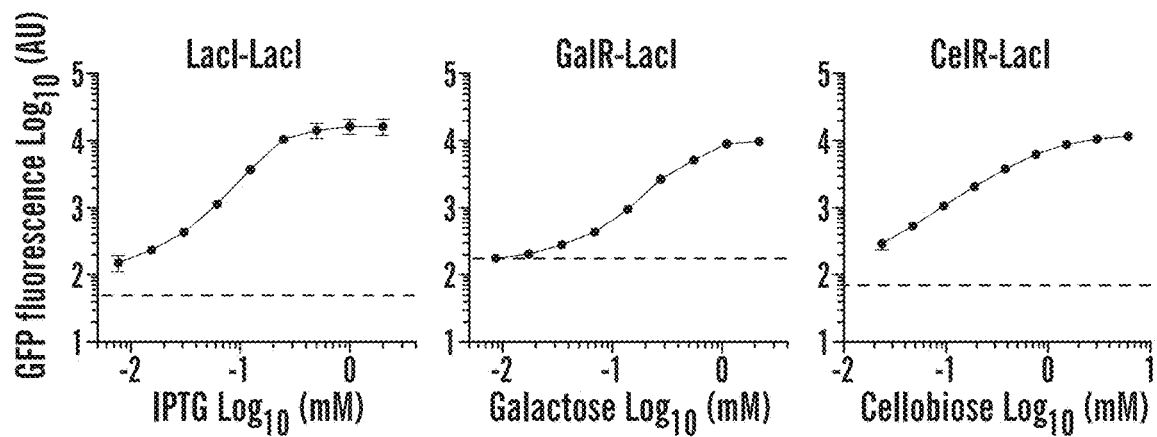
FIG. 16B

DEADMAN AND PASSCODE MICROBIAL KILL SWITCHES

CROSS-REFERENCE TO RELATED APPLICATIONS

This application is a 35 U.S.C. § 371 National Phase Entry Application of International Application No. PCT/US2016/054767 filed Sep. 30, 2016, which designated the U.S., and which claims benefit under 35 U.S.C. § 119(e) of U.S. Provisional Application Ser. No. 62/235,186 filed on Sep. 30, 2015, the contents of which are herein incorporated by reference in their entireties.

GOVERNMENT SUPPORT

This invention was made with Government Support under Contract No. HDTRA1-14-1-0006, awarded by the Defense Threat Reduction Agency; Contract No. N000141110725, awarded by the Office of Naval Research; and Contract No. FA9550-14-1-0060 awarded by the Air Force Office of Scientific Research. The Government has certain rights in the invention.

SEQUENCE LISTING

The instant application contains a Sequence Listing which has been submitted electronically in ASCII format and is hereby incorporated by reference in its entirety. Said ASCII copy, created on Jun. 6, 2018, is named 701586-085761US-PX_SL.txt and is 35,050 bytes in size.

FIELD OF THE INVENTION

This invention relates to genetically engineered biological circuits and their uses.

BACKGROUND

With the advent of synthetic biology, genetically modified microorganisms have been increasingly used for biomedical, industrial and environmental applications[1-6]. Deployment of these engineered microbes in large scales and open environments calls for the development of safe and secure means to restrain their proliferation. Pioneering biocontainment systems used metabolic auxotrophy in which target cells could only grow in the presence of an exogenously supplied metabolite[7,8], and the recent creation of an E. coli strain with an altered genetic code enabled production of synthetic auxotrophy strains in which an exogenous supply of non-natural amino acids is required for cell survival[9,10]. Traditional metabolic auxotrophy strains are hampered by the potential for inadvertent complementation by crossfeeding or by the presence of the metabolite in heterogenous environments, and synthetic auxotrophy systems rely on extensive genome-wide engineering that can be impractical for many industrial production and biotherapeutic microbes. Furthermore, they are intrinsically difficult to reprogram for different environmental conditions, limiting their application.

SUMMARY OF THE INVENTION

Described herein, in part, are programmable biocontainment circuits. In some embodiments, a switch termed herein as a "Deadman kill switch" that uses, in part, a transcription-based monostable toggle design to provide rapid and robust target cell killing in the absence of an input survival signal or condition is used, and, in some embodiments, a circuit termed herein a "Passcode circuit" or "Passcide kill switch" that uses hybrid transcription factors (TFs) to construct complex environmental requirements for cell survival is provided. As described herein, a tripartite strategy of (i) TF protein engineering to detect diverse input signals, (ii) robust circuit design to provide signal processing, and (iii) redundant toxin-induced and protease-mediated cell killing mechanisms was used. The resulting biocontainment systems described herein are modular, flexible and extensible, and are useful across many industrial and biotherapeutic applications.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Other than in the operating examples, or where otherwise indicated, all numbers expressing quantities of ingredients or reaction conditions used herein should be understood as modified in all instances by the term "about." The term "about" when used in connection with percentages can mean±1%.

The term "statistically significant" or "significantly" refers to statistical significance and generally means a two standard deviation (2SD) difference, above or below a reference value. Additional definitions are provided in the text of individual sections below.

BRIEF DESCRIPTION OF THE FIGURES

The patent or application file contains at least one drawing executed in color. Copies of this patent or patent application publication with color drawing(s) will be provided by the Office upon request and payment of the necessary fee.

" FIG. 1A. Deadman circuit control of toxin gene expression. Cell viability was measured by CFU count following removal of the survival signal (anhydrotetracycline, ATc) and is displayed as a ratio of cells without ATc to cells with ATc at each time point. FIG. 1B. Deadman circuit control of targeted essential protein degradation.

Inclusion of the mf-lon specific pdt#1 tag on the specified essential gene causes mf-Lon-mediated degradation of the essential protein upon Deadman circuit activation. FIG. 1C. Combined control of toxin expression and targeted essential protein degradation increases Deadman-induced cell death. In particular, targeted MurC degradation and EcoRI expression reduced cell viability to below the limit of detection (<1×10−7) after 6 hours (indicated by a "0"). All data points represent mean±S.D. of three biological replicates.

FIG. 3A. An environmental sensing module (ESM) from one LacI family TF can be combined with the DNA recognition module (DRM) of a second LacI family TF to create a hybrid TF with the specified sensory and regulatory properties. FIG. 3B. Using this approach, ESMs from LacI, GalR and CelR were combined with the DRM from LacI or ScrR to control GFP expression from a promoter containing lacO or scrO operator sites as indicated. Plots show GFP expression after 3 hours exposure to IPTG, galactose or cellobiose, and results are presented as a ratio to GFP expression in unexposed cells.

" FIG. 4A. Passcode circuit schematic and logic gate behavior. Cell survival requires the continued presence of inputs a and b and the absence of input c. Loss of input a or b or the addition of input c cause the passcode circuit to activate toxin expression, leading to cell death. FIG. 4B. Three embodiments of a passcode kill switch were used to control expression of ecoRI, mf-lon-mediated MurC degradation (mf-lon), or both ecoRI and mf-lon. Cells containing each circuit were placed in each of eight possible combinations of the three input molecules, and cell viability was measured by CFU count after 8 hours. In each condition, cell survival is displayed as a ratio of cells in that condition to cells in the "survival" condition highlighted in green. Cell survival below the limit of detection (<1×10$^{-7}$) is indicated by a "0". All data points represent mean±S.D. of three biological replicates.

FIGS. 5A-5B. Cells with Deadman or Passcode circuits containing one toxin (EcoRI) or two toxins (EcoRI and mf-Lon) were passaged under survival conditions for 4 days, and sub-populations of cells were periodically switched to nonpermissive media (Deadman: no ATc, Passcode: no inducer) for eight hours. The survival ratio is the ratio of cells that survive in the death state to those in the survival state. Data points represent the mean±S.D. of six biological replicates. The passcode circuit was also passaged in E. coli MDS42pdu ΔrecA (MDS strain), which lacks recombinogenic and mobile genomic elements11. Deadman and Passcode circuits that do not contain toxin modules displayed increased stability throughout the 4 day experiment. FIG. 5C. Cells containing Deadman and Passcode circuits that survived exposure to their respective death states were isolated, and the entire circuit and toxin(s) were sequenced to identify the inactivating mutations. Toxin gene disruption by genome-encoded insertion-sequence (IS) elements and large deletions were the predominant cause of circuit inactivation. In the two-toxin Deadman circuit, inactivating TetR mutations allowed continued LacI expression and repression of toxin genes in non-biocontainment conditions.

FIG. 7A. Toggle circuits with a range of predicted LacI and TetR RBS strengths (L1-L3 and T1-T3, respectively) were tested for relative expression levels. mCherry fusions to the C-terminus of LacI and TetR was used to measure LacI and TetR expression levels under full induction. mCherry spectrometry measurements were normalized to cell growth (OD600), and RBS sequences are listed in Table 1. FIG. 7B. Circuit monostability was measured by observing the speed of the shift from the LacI+ state to the TetR+ state in the absence of inducers. Cells containing each toggle circuit were grown in the presence of ATc, transferred to media without inducer, and measured by flow cytometry after 6 hours. Toggle 5, which showed the fastest change in mCherry fluorescence, was chosen for use in the Deadman circuit. "Null" indicates cells without mCherry. Data points represent the mean±S.D. of three biological replicates.

FIGS. 8A-8C show exemplary Deadman switch dynamics. FIG. 8A. Cells containing the Deadman circuit pDM1 were grown in the presence of ATc, transferred to media containing ATc, IPTG, or no input (−), and then measured by flow cytometry after six hours. Cells remained in the LacI+/mCherry-state in the presence of ATc but shifted to the TetR+/mCherry+ state in the absence of ATc or in the presence of IPTG. "Null" indicates cells that do not contain mCherry. FIG. 8B. Deadman switch dynamics following ATc removal as described in FIG. 8A. Upon removal of ATc, mCherry expression increased within 4 hours. FIG. 8C. Representative flow cytometry analysis of Deadman switch dynamics in the presence (left) or absence (right) of ATc. Data points in FIG. 8A and FIG. 8B represent the mean±S.D. of three biological replicates. Where the S.D. is small, error bars are present but inside the data symbol.

FIG. 9A. Schematic representation of the improved Deadman circuit. Three palindromic lacO operator sites were included to reduce leaky expression from the pTrc promoter, and a transcriptional terminator was added to reduce readthrough transcription from the upstream promoter. FIG. 9B. Following growth in media containing ATc, strains harboring pDM1 or pDM2 were measured for mCherry expression in the presence or absence of ATc. FIG. 9C. In the presence of ATc, cells harboring pDM2 showed reduced mCherry expression levels that are indistinguishable from cells that contain no mCherry (Null), implying that the added terminator and promoter improved regulatory control over the reporter gene. Data points represent the mean±S.D. of three biological replicates. Where the S.D. is small, error bars are present but inside the data symbol.

FIG. 10A. A schematic of Deadman circuits pDM2 and pDM3. Unbalanced reciprocal repression by LacI and TetR causes strong mCherry expression in the absence of ATc (pDM2). Targeted degradation of LacI by mf-Lon protease speeds the transition to toxin expression upon loss of ATc (pDM3). FIG. 10B. Introduction of mf-Lon-mediated degradation of LacI improved the switching dynamics of the Deadman switch. Cells containing pDM2 or pDM3 were grown in the presence of ATc, transferred to media with and without ATc, and then measured by flow cytometry at the indicated time. Data points represent the mean±S.D. of three biological replicates. Where the S.D. is small, error bars are present but inside the data symbol. FIG. 10C. Representative flow cytometry plots for cells containing pDM2 and pDM3 at 0 and 6 hours after removal of ATc as shown in FIG. 10B. Cells show monomodal distributions.

FIGS. 11A-11B show RBS strength optimization for Deadman switch toxins. FIG. 11A. A range of predicted RBS strengths was used to optimize expression of EcoRI, CcdB, and MazF. Cells with Deadman circuits containing each RBS candidate were grown in the presence of ATc (survival state) or IPTG (induced death state), and the ratio of cell growth in the IPTG-treated and ATc-treated cultures was used to measure the relative killing activity. FIG. 11B. Growth rate analysis of ATc-treated cells was used to estimate the cellular burden of leaky toxin expression for each RBS candidate. RBS candidates that showed high killing activity in the induced cell death state and low cellular burden in the survival state were chosen for each toxin; 1500 for EcoRI, 500 for CcdB, and 1000 for MazF. "*" indicates RBS candidates that could not be cloned under survival conditions despite multiple attempts. Data points represent the mean±S.D. of three biological replicates.

FIG. 12 depicts hybrid TF module prediction. LacI family members have conserved structural features that reflect a common mechanism in which effector binding to the regulatory domain induces structural changes in the hinge-helix (HH) motif that alter the orientation of the helix-turn-helix (HTH) motif to weaken DNA operator binding[1,2]. Effector binding-induced conformational changes are largely limited to the regulatory domain and the HH motif[3,5], and while the HH motif makes contact with the DNA operator site, only the HTH motif makes direct, sequence-specific contact with nucleobases in the major groove complex[5-7]. Based on this evidence, the HTH and HH appear to play distinct roles in allosteric regulation—while the HTH mediates operator sequence-specificity, the function of the HH is integrated with the regulatory domain and is involved in receiving and translating the allosteric response. In contrast to work by Meinhardt et al.[8,9] that uses the boundary between the regulatory and HH motifs to generate hybrid TFs, we reasoned that a boundary between the HH and HTH domains would generate distinct environmental sensing and DNA recognition modules.

FIG. 13 depicts protein sequence alignment of relevant LacI/GalR family members. ScrR-V and ScrR-K are ScrR from *Vibrio alginolyticus* and *Klebsiella pneumoniae*, respectively. CelR originates from *Thermobifida fusca*. All other family members are from *E. coli*. Residues 1-70 of LacI and the homologous sequences of the other members are shown. FIG. 13 discloses SEQ ID NOS 55-65, respectively, in order of appearance.

FIG. 14 depicts structures of DNA recognition modules of LacI family members. Crystal structures of the N-terminal region of LacI (left) and PurR (right) are shown, including their helix-turn-helix motif (HTH; purple), hinge helix motif (HH; orange) and part of the regulatory domain connected to the HH motif (green). The HTH binds to the major groove to interact with nucleobases, and the HH motif sits in the minor grooves to interact with the DNA backbone. The PDB IDs of the LacI and PurR crystal structures are 1EFA and 1QPZ, respectively.

FIGS. 16A-16C demonstrate a structure-based strategy to identify protein modules that mediate allosteric response and DNA recognition in LacI/GalR family TFs. FIG. 16A. A module interchange strategy for engineered hybrid TFs. The environmental sensing module (ESM) of one LacI/GalR family TF can be combined with the DNA recognition module (DRM) of a second LacI/GalR family TF to create a hybrid TF with the specified sensory and regulatory properties. FIG. 16B. LacI DRM is combined with ESMs from other LacI/GalR family TFs to create hybrid TFs. Native LacI (LacI-LacI) and the GalR-LacI and CelR-LacI hybrid TFs were expressed in strains containing gfp under control of the pLlacO promoter containing a lacO operator site bound by the LacI DRM. Promoter regions containing the lacO operator and the −35 and −10 elements are shown. Cells containing the TF and reporter constructs were treated with a range of inducer concentrations for 3 hours and assessed for GFP expression by flow cytometry. FIG. 16B discloses SEQ ID NO: 68. FIG. 16C. DRM from ScrR can also be used to engineer hybrid TFs. Hybrid TFs were constructed by replacing the DRMs of LacI, GalR, and CelR with that of ScrR and were then tested with reporter plasmids that use either the pLscrO-1 or pLscrO-2 promoter to control GFP expression. The promoter region containing the scrO operators and the −10 and −35 elements are shown. GFP fluorescence was determined by flow cytometry 3 hours after exposure to the indicated inducer concentrations. The dotted lines represent the basal GFP fluorescence in cells not exposed to the inducer. Data points represent the mean±S.D. of three biological replicates. FIG. 16C discloses SEQ ID NOS 69 and 70, respectively, in order of appearance.

FIG. 20A. Three versions of the Passcode circuit were developed using the indicated circuit architecture. For each Passcode circuit, constitutive expression of hybrid A and hybrid B containing the LacI DRM was used to control expression of hybrid C containing the ScrR DRM which controls gfp expression. FIG. 20B. Cells containing each Passcode circuit were exposed to all eight combinations of the three small molecule inputs as shown, and GFP expression was assessed by flow cytometry after 3 hours. FIG. 20C. Representative flow cytometry plots show cells containing the Passcode circuits in each environmental condition after 3 hours of induction as in FIG. 20B. Data points represent the mean±S.D. of three biological replicates.

FIG. 24A. Cells containing pDM3 with mCherry as the ouput module were passaged in the presence of ATc for 4 days. Sub-populations of these cells were periodically tested for circuit function by transferring the cells to media with and without ATc for 8 hours. Data points were measured by flow cytometry and represent the mean±S.D. of six biological replicates. FIG. 24B. Representative flow cytometry plots for each time point in the presence or absence of ATc. Cells passaged for 4 days displayed monomodal population distributions that were very similar to cells tested in day 1.

DETAILED DESCRIPTION

Figure 1A:
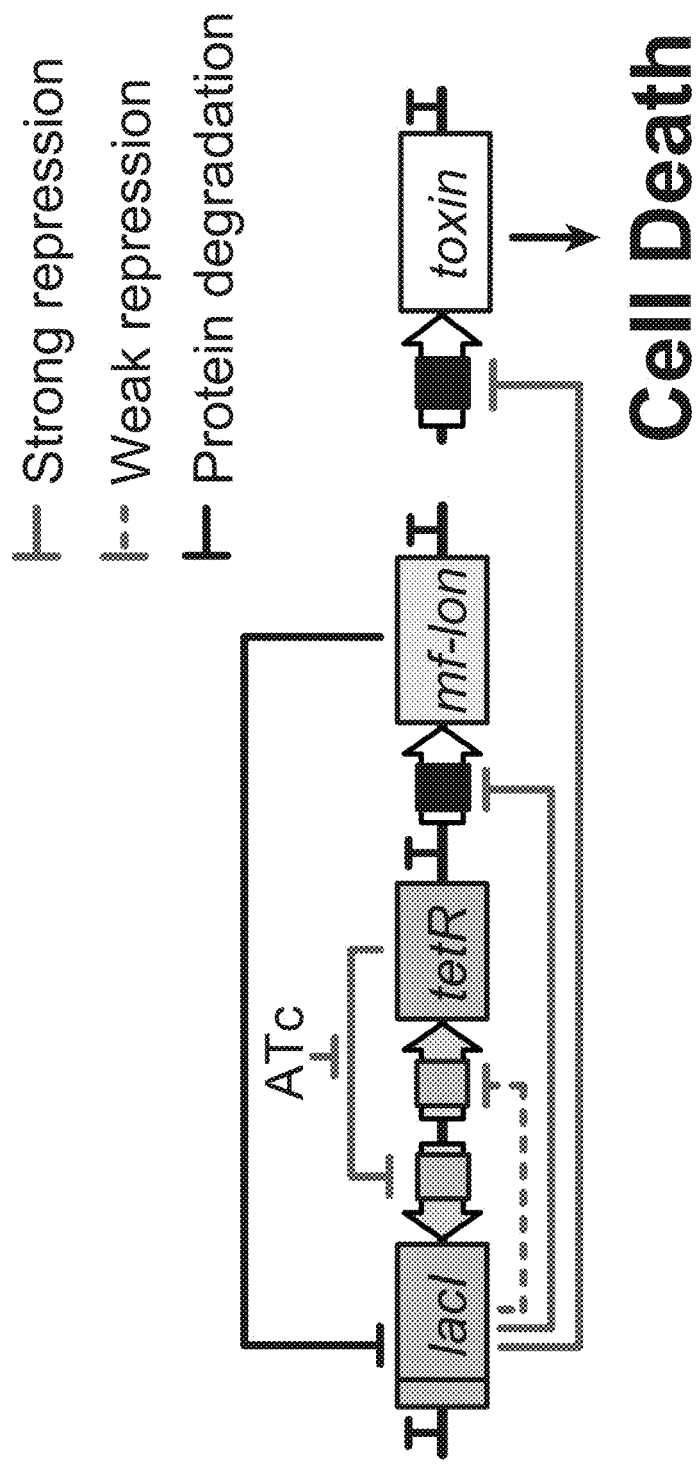
FIGS. 1A-1C depict an exemplary embodiment of a "Deadman kill switch.
Figure 1A:
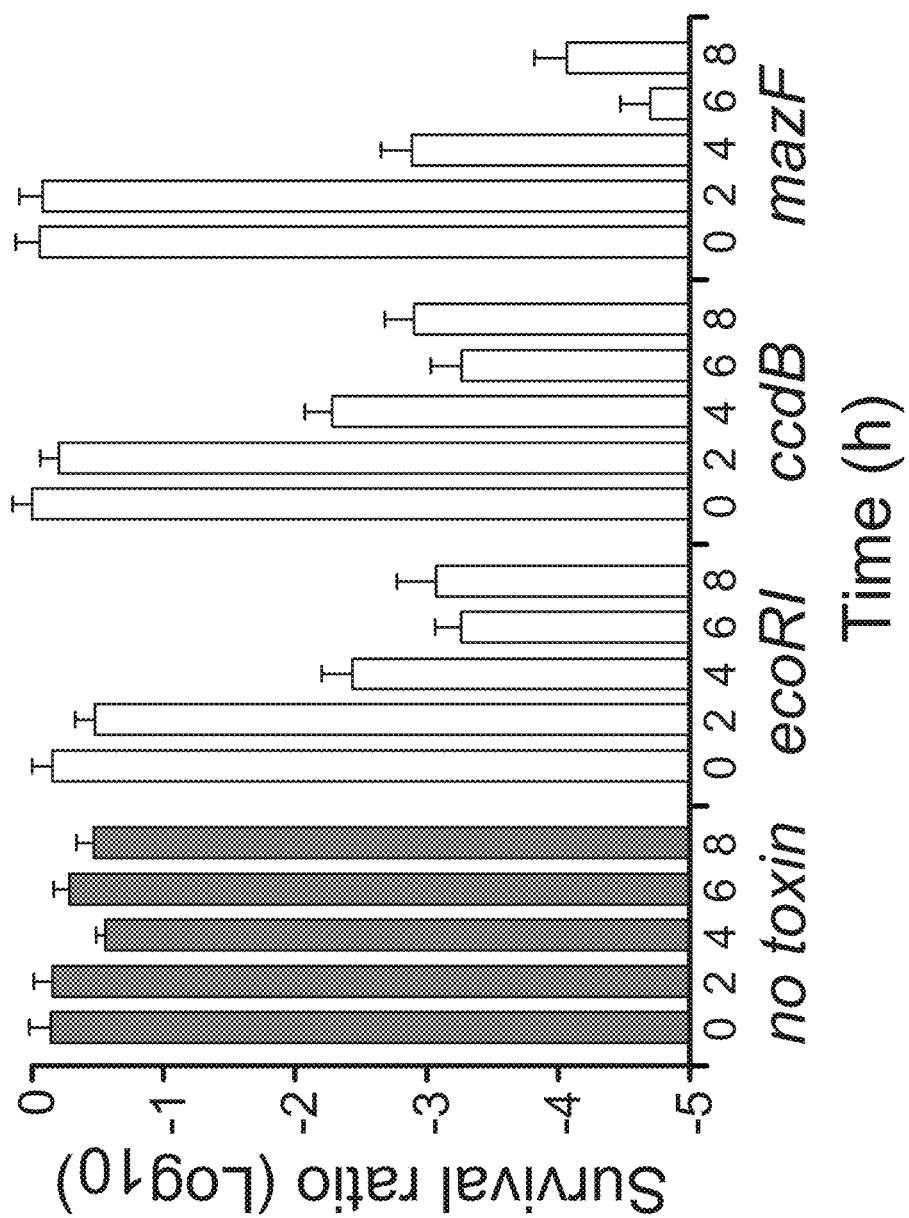

Provided herein are novel, engineered circuit-based microbial "kill switches" that restrict host cell survival to an environment defined by specific input signals. Unlike existing biocontainment systems with fixed survival conditions that are difficult to modify, the Deadman and Passcode kill switches described herein are modular and inherently customizable, both in the environmental conditions that control circuit activation and in the output modules that control cell fate. In addition to its use in biocontainment systems, the Passcode circuit has particular utility as a tool for intellectual property protection, where unauthorized growth of strains without the appropriate "passcode" molecules would induce cell death. With the proper choice of toxins, including, but not limited to an endonuclease, exemplified herein by EcoRI, embodiments of the Passcode circuits described herein can be used to not only kill the host cell but also degrade its genome and accompanying plasmids to deter attempts at reverse-engineering the strain of interest. Use of hybrid TFs that respond to proprietary small molecule inputs can further secure the strain against theft, even if its genome is sequenced, in some embodiments.

The Deadman and Passcode switches described herein provide robust information processing circuits to couple environmental signals with conditional survival of the microbial host. The Deadman kill switch described herein is based, in part, on a monostable circuit that passively activates toxin gene expression in the absence of a small molecule input, such as ATc. Since the small molecule input, such as ATc, is not normally found in nature, engineered cells that escape containment will trigger cell death to prevent the spread of the organism or its genetic content into the surrounding ecosystem. Unlike auxotrophy-based biocontainment where the environmental signal is an intrinsic feature of the system[9,10], the environmental sensing and cell killing systems are decoupled in the Deadman switches described herein. These circuits rely on two main elements for functionality: (1) the orthogonality of the TFs to create a toggle switch, and (2) their relative activity under induced expression. As such, the Deadman circuits described herein are highly modular, and the environmental signal detected by the circuit can be altered, for example, by replacing TetR with a wide range of transcription factors, including more than 80,000 annotated TetR family members,[38] as well as orthogonal LacI/GalR family members, including hybrid TFs as described for the Passcode switches described herein. In addition, the Deadman circuits described herein have an additional fail-safe mechanism that activates toxin production and cell death in the presence of another molecule, such as IPTG, enabling exogenous control over the microbe's survival even as the cell uses the circuit to monitor its environment.

Similar to the Deadman switches, the Passcode circuits described herein are based on a two-layered transcriptional repression design. To build hybrid transcription factors (TFs), the conserved boundaries of the ESMs (environmental sensing modules) and DRMs were identified within the LacI/GalR family members LacI, GalR, CelR and ScrR. The resulting environmental sensing and DNA binding modules provide independent control of the sensory input and regulatory output of each hybrid TF. Work by Meinhardt et al.[27,28] used the boundary between the conserved regulatory domain and HH motif to create hybrid TFs, but some of these hybrids required additional protein engineering and mutagenesis to become functional. Herein, a novel and discrete boundary between the conserved HH and HTH motifs was identified and can be used to create independent environmental sensory and DNA binding domains that can be efficiently combined without further protein engineering. The modularity provided by these hybrid TFs dramatically expands the number and range of environmental signals that can be used to control biocontainment systems such as the Deadman and Passcode circuits described here, as the ESM and DRM boundaries defined in this study can be used to incorporate sensing modules from many of the ~29,000 LacI/GalR family members[39] that detect diverse environmental signals.

The hybrid TFs described herein can also be used to functionalize other synthetic circuits, including the Deadman switch, to respond to different environmental signals. Moreover, the regular use of LacI and TetR in other bacteria[40,41] indicates that these circuits can be readily transferred to other microbes, including industrial production strains. Replacement of the antibiotic resistance cassettes in these plasmids with well characterized selection systems that use toxin-antitoxin modules or auxotrophy complementation also enables their use in biotherapeutic applications[4,42].

Deadman Kill Switches

Provided herein, in some aspects, are engineered biological circuits comprising modular components for use as and with passively activated biocontainment systems for engineered microbes termed "Deadman kill switches." "Deadman kill switches" or "Deadman kill circuits," as these terms are used herein, refer to an engineered, addressable cellular memory module that can be constructed from repressible sequences arranged in a mutually inhibitory network and which exhibits robust monstable behavior. For example, reciprocal repression can be mediated by transcription factors, such as the LacI and TetR transcription factors, which form transcription states that are maintained by the circuit's linked feedback loops (see, for example, FIG. 6).

The monostable behavior of the Deadman kill switches, as described herein, arises from a mutually inhibitory arrangement of at least two repressible sequences, such that a small molecule-binding transcription factor is used to produce a 'survival' state in which repression of toxin production is linked to the presence of a specific environmental signal. Upon loss of the environmental signal, the circuit switches permanently to the 'death' state in which the now &repressed toxin production kills the cell in which the Deadman kill switch is present.

In one aspect, then, a deadman kill switch is a biological circuit or system rendering a cellular response sensitive to a predetermined condition, such as the lack of an agent in the cell growth environment, e.g., an exogenous agent. Such a circuit or system can comprise a nucleic acid construct comprising expression modules that form a deadman regulatory circuit sensitive to the predetermined condition, the construct comprising expression modules that form a regulatory circuit, the construct including:

i) a first repressor protein expression module, wherein the first repressor protein binds a first repressor protein nucleic acid binding element and represses transcription from a coding sequence comprising the first repressor protein binding element, and wherein repression activity of the first repressor protein is sensitive to inhibition by a first exogenous agent, the presence or absence of the first exogenous agent establishing a predetermined condition;

ii) a second repressor protein expression module, wherein the second repressor protein binds a second repressor protein nucleic acid binding element and represses transcription from a coding sequence comprising the second repressor protein binding element, wherein the second repressor protein is different from the first repressor protein; and iii) an effector expression module, comprising a nucleic acid sequence encoding an effector protein, operably linked to a genetic element comprising a binding element for the second repressor protein, such that expression of the second repressor protein causes repression of effector expression from the effector expression module, wherein the second expression module comprises a first repressor protein nucleic acid binding element that permits repression of transcription of the second repressor protein when the element is bound by the first repressor protein, the respective modules forming a regulatory circuit such that in the absence of the first exogenous agent, the first repressor protein is produced from the first repressor protein expression module and represses transcription from the second repressor protein expression module, such that repression of effector expression by the second repressor protein is relieved, resulting in expression of the effector protein, but in the presence of the first exogenous agent, the activity of the first repressor protein is inhibited, permitting expression of the second repressor protein, which maintains expression of effector protein expression in the "off" state, such that the first exogenous agent is required by the circuit to maintain effector protein expression in the "off" state, and removal or absence of the first exogenous agent defaults to expression of the effector protein.

In one embodiment, the effector is a toxin or a protein that induces a cell death program. Any protein that is toxic to the host cell can be used. In some embodiments the toxin only kills those cells in which it is expressed. In other embodiments, the toxin kills other cells of the same host organism.

In the examples described herein, the first repressor protein is the tet repressor, tetR, and the second repressor protein is the lac repressor, LacI, but essentially any pair of different repressor proteins for which the repressor binding element is known can be used. Indeed, where both LacI and TetR are known to be members of large families of related proteins expressed in different species of organism, any of the related members, with their cognate repressor binding elements can be used to construct a deadman kill switch circuit as described herein. A number of repressor proteins and the elements to which they bind are known in the art, and are described, for example in Terpe, Appl. Microbiol. Biotechnol. 72: 211-222 (2006), and in U.S. patent application publication No. 20130034907, which are incorporated herein by reference in their entireties.

The deadman kill switch circuit can further include an expression module for a targeted protease or a targeted nuclease that degrades the first repressor protein or its message to thereby amplify the effect of the down-regulation of first repressor protein expression. The targeted protease or nuclease can be under the negative control of the second repressor protein, such that loss of the exogenous agent results in degradation of the first repressor protein or its message as well as derepression of expression of the first repressor protein.

By introducing a construct encoding the respective modules into a host cell, e.g., a host cell that produces a desired agent, a method is provided in which the host cell is rendered sensitive to the presence of the exogenous agent such that when the host cell either escapes containment or is no longer needed, or desired e.g., in a therapeutic use, the removal or absence of the exogenous agent kills the host cell.

In one embodiment, a bistable "toggle switch" circuit, such as those described in U.S. patent application publication No. 20130034907, which is incorporated herein by reference in its entirety, can be converted into a deadman kill switch by manipulating the stength of expression or stability of one of the mutually-regulated repressor proteins. Reducing the efficiency of expression or activity of one of the repressors in a toggle switch circuit can bias the system towards expression or activity of one repressor that results in cell death when that repressor is active. In the toggle switch system, the product of each repressor sequence, i.e., the repressor, can inhibit, at a transcriptional level, a translational level, or a combination thereof, the expression of a product encoded by the other repressor sequence. Thus, in the absence of an appropriate input or inducing agent, such as a transcriptional activating agent, two stable states are possible: a first state in which a first repressor is expressed and inhibits expression of a second repressor sequence, and a second state in which the second repressor is expressed and inhibits expression of the first repressor sequence. This is a bistable system. In some aspects of a bistable system, repressors act at the transcriptional level, whereby a first promoter sequence drives expression of a first repressor sequence that encodes for a repressor specific for a second promoter sequence. The second promoter sequence, in turn, drives expression of a second repressor sequence that encodes for a repressor specific for a second promoter sequence. In such an aspect, switching between the two states (i.e., expression of the first or second repressor) is mediated by the presence of an exogenous or endogenous input agent, such as an agent that prevents repressor binding to the currently inactive promoter. In such an embodiment, the agent permits the opposing repressor to be maximally transcribed until it stably represses the originally active promoter. In other embodiments, repressors in a genetic toggle switch can act at the translational level, whereby a first repressor encodes a product, such as an inhibitory RNA molecule, that inhibits or prevents translation of the second repressor, or causes degaration of the second repressor mRNA. In other embodiments of the aspects described herein, different repressors in a genetic toggle switch can use different mechanisms of repression, i.e., transcriptional, translational, or combinations thereof.

Figures 7A, 7B:
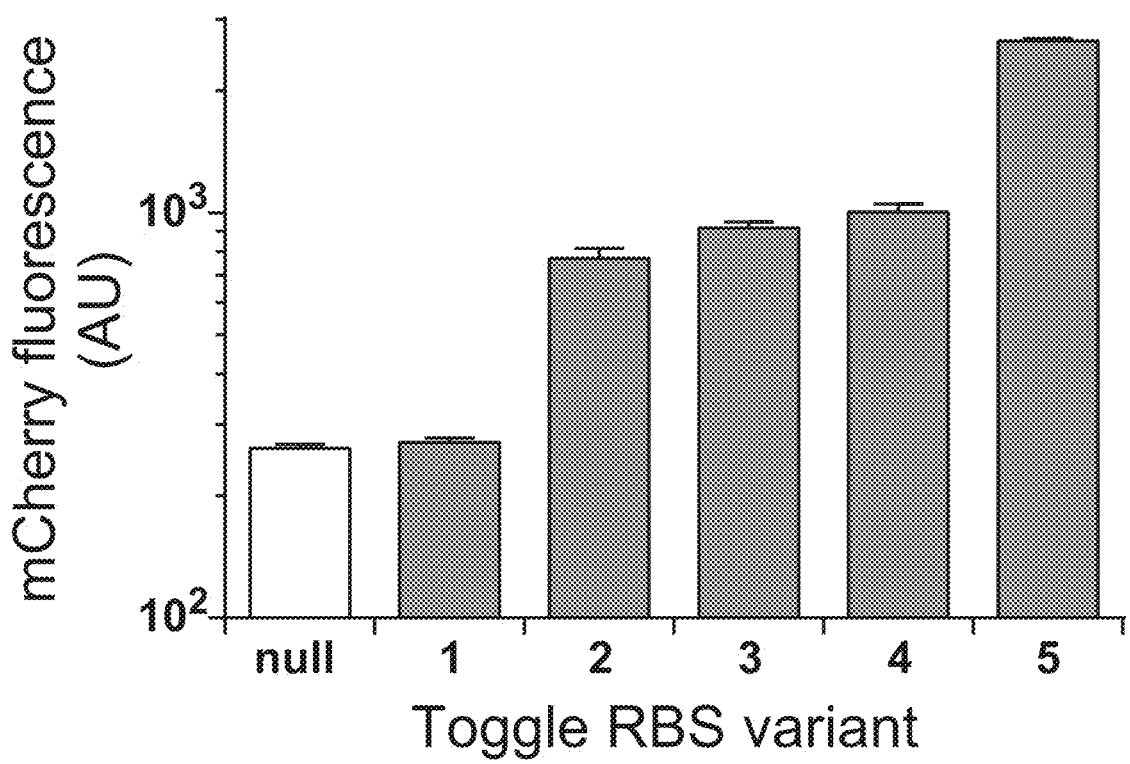
FIGS. 7A-7B show LacI and TetR RBS strength analysis.

To create a circuit in which the 'death' state is dominant in the absence of the survival signal, i.e., to convert a bistable toggle switch to a monostable deadman kill switch, the expression of one repressor can be manipulated to bias the system either towards or away from expression of that repressor. In the non-limiting examples descrigbed herein, the ribosome binding site (RBS) strengths of LacI and TetR were manipulated to favor TetR expression in a single-copy plasmid (FIGS. 7A-7B and Supplementary Methods). In the resulting monostable circuit, the presence of the TetR inhibitor anhydrotetracycline (ATc) is required to maintain the circuit in the subordinate LacI+ 'survival' state (FIGS. 8A-8C). Incorporation of toxin genes into the TetR+state creates a kill switch where the presence of ATc is required to block toxin expression and cell death.

Figure 9A:
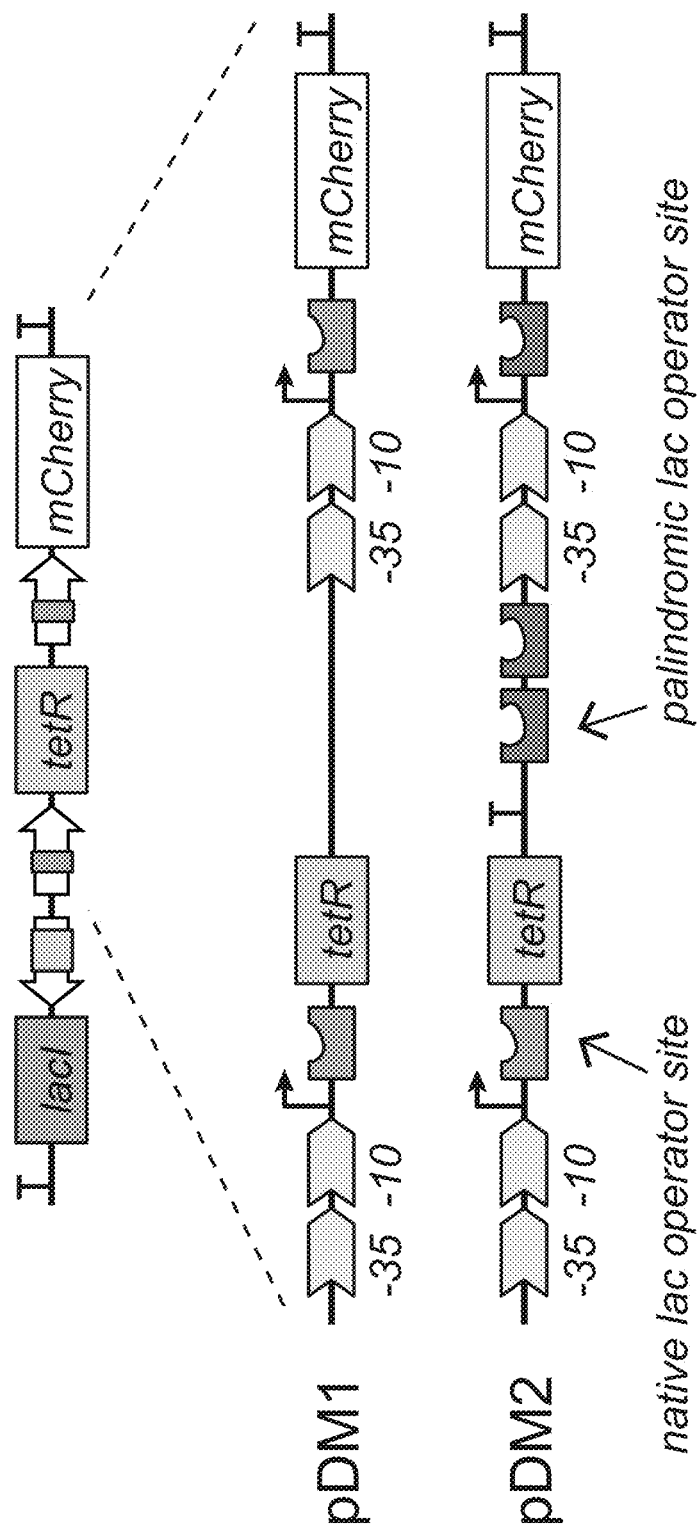
FIGS. 9A-9C show an exemplary Deadman circuit refinement to achieve tight control over mCherry expression.
Figure 9C:
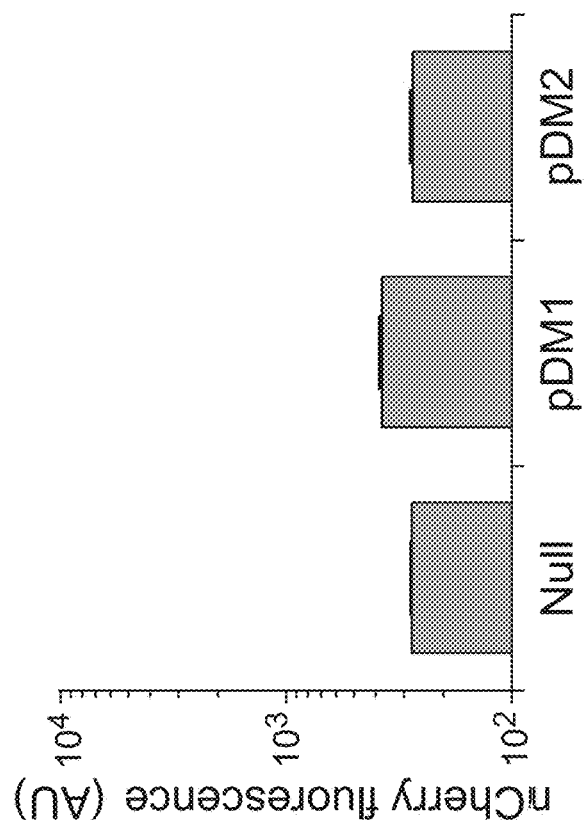
Figure 9B:
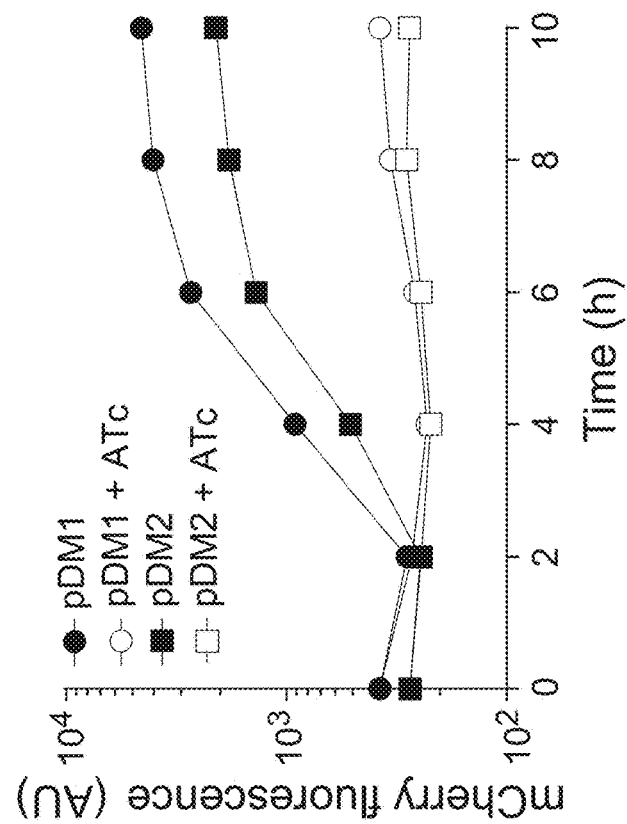
Figure 10A:
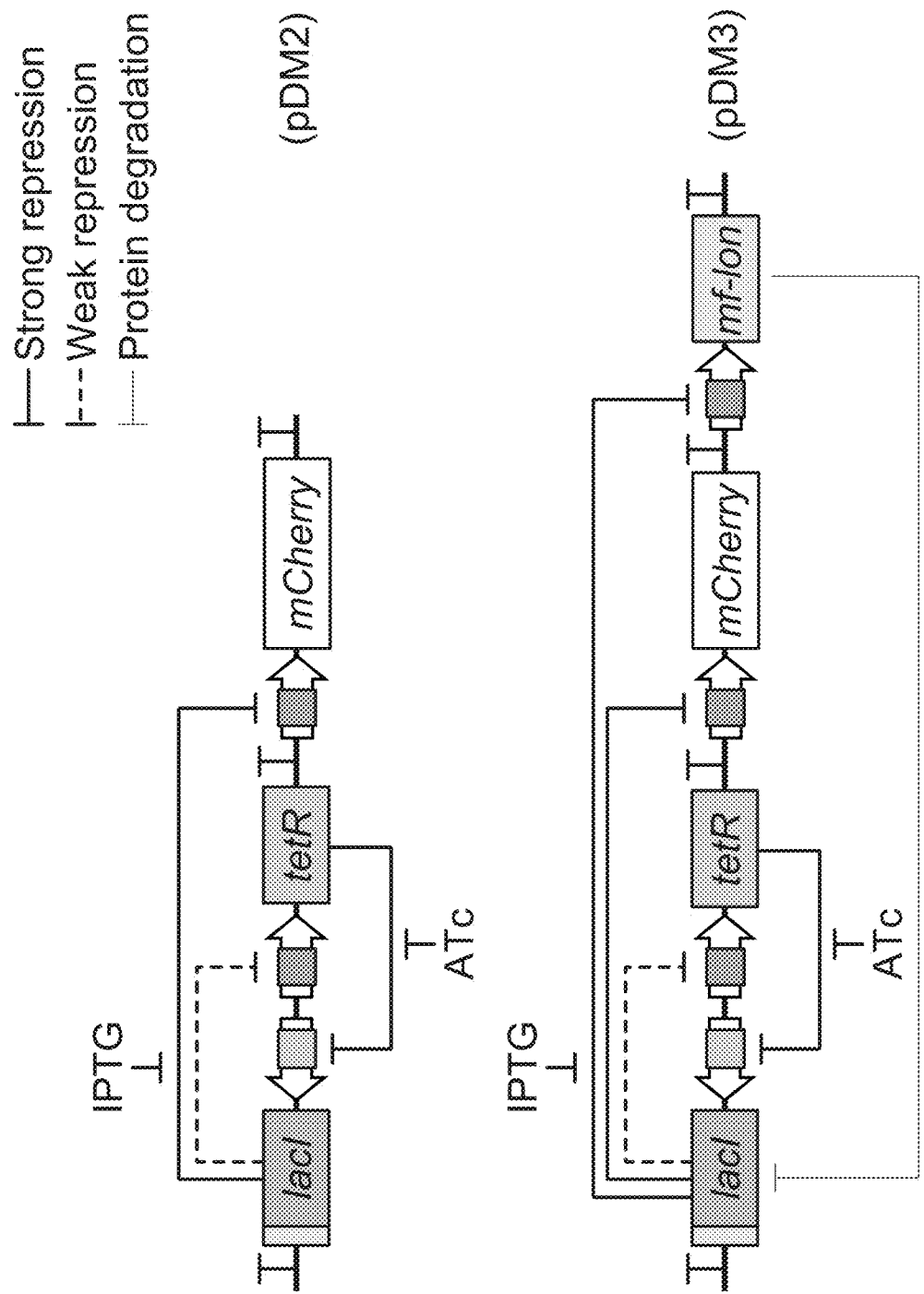
FIGS. 10A-10C show an exemplary construction of Deadman circuit.
Figure 10B:
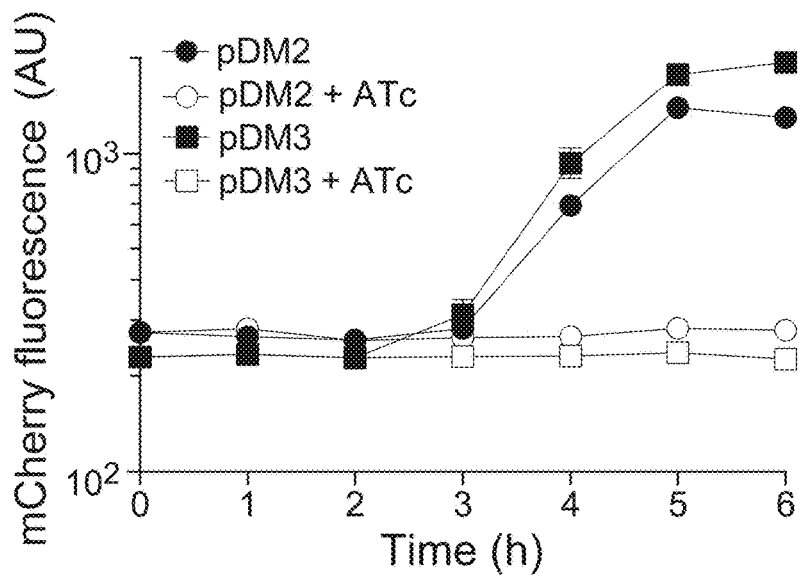
Figure 10C:
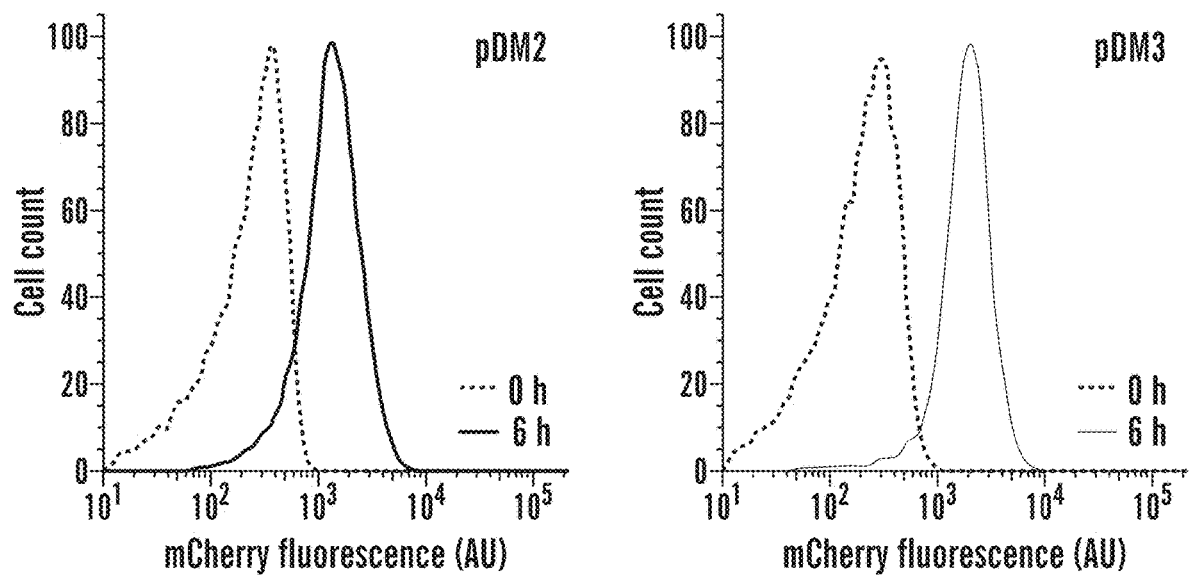

Additional repressor binding sites can be included to minimize leaky toxin expression, or other steps can be taken to ensure toxin expression occurs only when desired. In the Examples described herein, palindromic LacI operator sites were included in the toxin gene promoter for this purpose[19] and a transcriptional terminator was included upstream of the promoter to insulate the gene from spurious transcription (FIGS. 9A-9C). To accelerate the circuit's switching dynamics, a degradation tag can be placed on a repressor protein. In the Examples, a tag was fused to the C-terminus of LacI that is specifically recognized by mf-Lon[20], a heterologous protease under control of a LacI-dependent promoter (FIGS. 10A-10C). Upon removal of ATc, TetR repression of lacI allows expression of mf-Lon, which targets LacI for degradation to create a positive feedback loop that accelerates the switch to the TetR+ state (FIG. 10B). Other proteases can be targeted in a similar manner, or the message encoding the repressor can also be targeted. Importantly, single-cell analysis of these circuits by flow cytometry showed a monomodal distribution of cells in the LacI+ and TetR+ state, demonstrating stable circuit expression across the cell population (see 0 and 6 hour data in FIG. 10C).

Figure 1B:
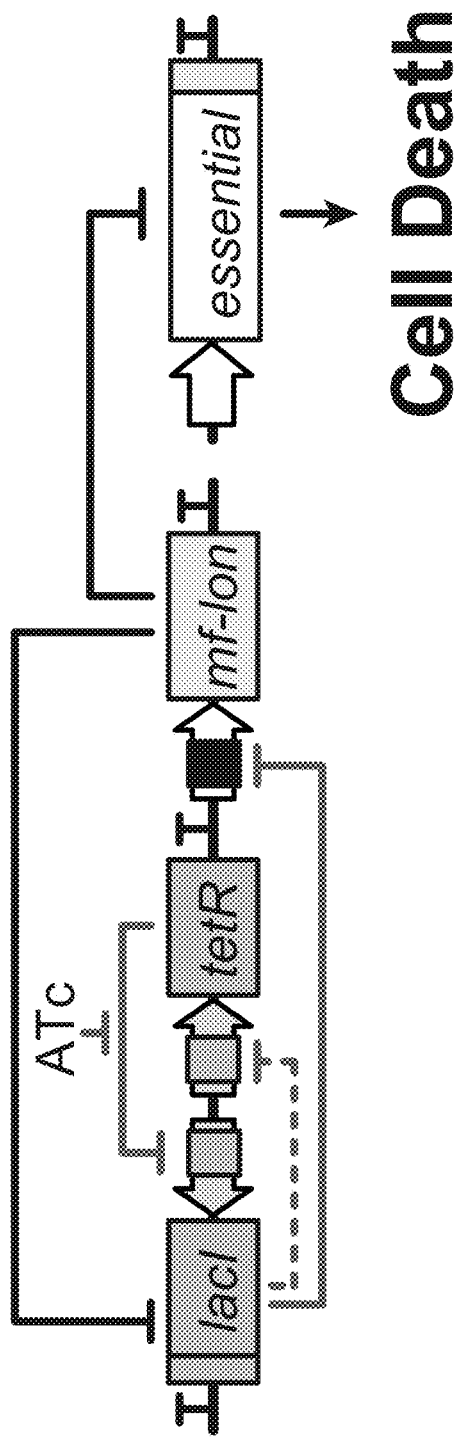
Figure 1B:
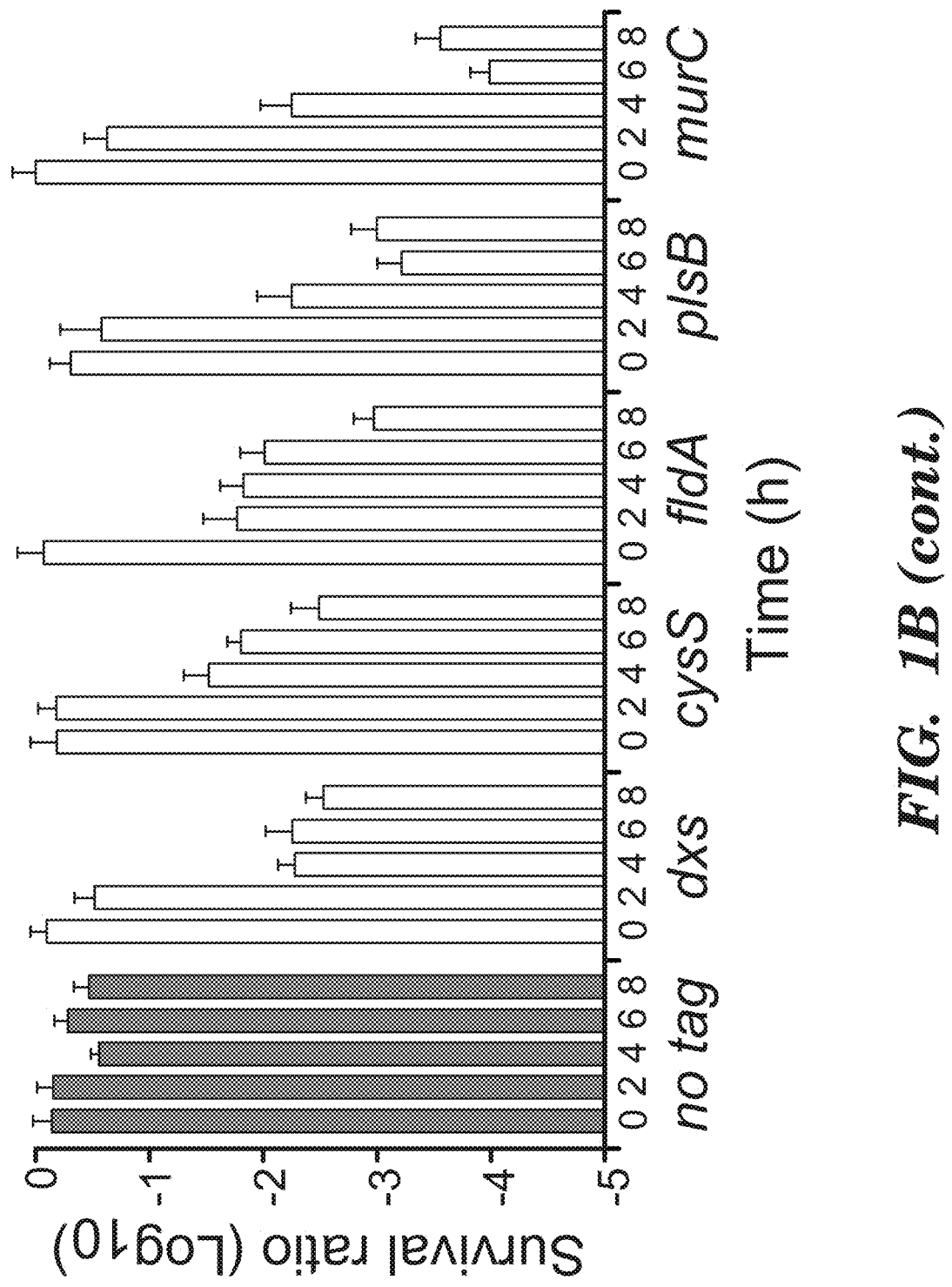

As noted above, any of a large number of products that will lead to cell death can be employed in a deadman kill switch. Agents that inhibit DNA replication, protein translation or other processes or, e,g., that degrade the host cell's nucleic acid are of particular usefulness. To identify an efficient mechanism to kill the host cells upon circuit activation, several toxin genes were tested that directly damage the host cell's DNA or RNA. The endonuclease ecoRI[21], the DNA gyrase inhibitor ccdB[22] and the ribonuclease-type toxin mazF[23] were tested because they are well-characterized, are native to $E.$ $coli$, and provide a range of killing mechanisms. The toxin genes were independently incorporated into the Deadman circuit, and a range of RBS strengths were tested for each toxin to optimize cell death upon circuit activation[24] (FIGS. 11A-11B). Upon removal of ATc, the toxins produced 3-5 logs of killing within 6 hours as measured by colony forming units (CFUs) (FIG. 1A). To increase the robustness of the circuit and provide an independent method of circuit-dependent cell death, the system can be further adapted to express, e.g., a targeted protease or nuclease that further interferes with the repressor that maintains the death gene in the "off" state. Upon loss or withdrawal of the survival signal, death gene repression is even more efficiently removed by, e.g., active degradation of the repressor protein or its message. As non-limiting examples, mf-Lon protease was used to not only degrade LacI but also target essential proteins for degradation (FIG. 1B). The mf-Lon degradation tag pdt#1 was attached to the 3' end of five essential genes whose protein products are particularly sensitive to mf-Lon degradation[20], and cell viability was measured following removal of ATc (FIG. 1B). Among the tested essential gene targets, the peptidoglycan biosynthesis gene murC provided the strongest and fastest cell death phenotype (survival ratio $<1\times10^{-4}$ within 6 hours).

Figure 1C:
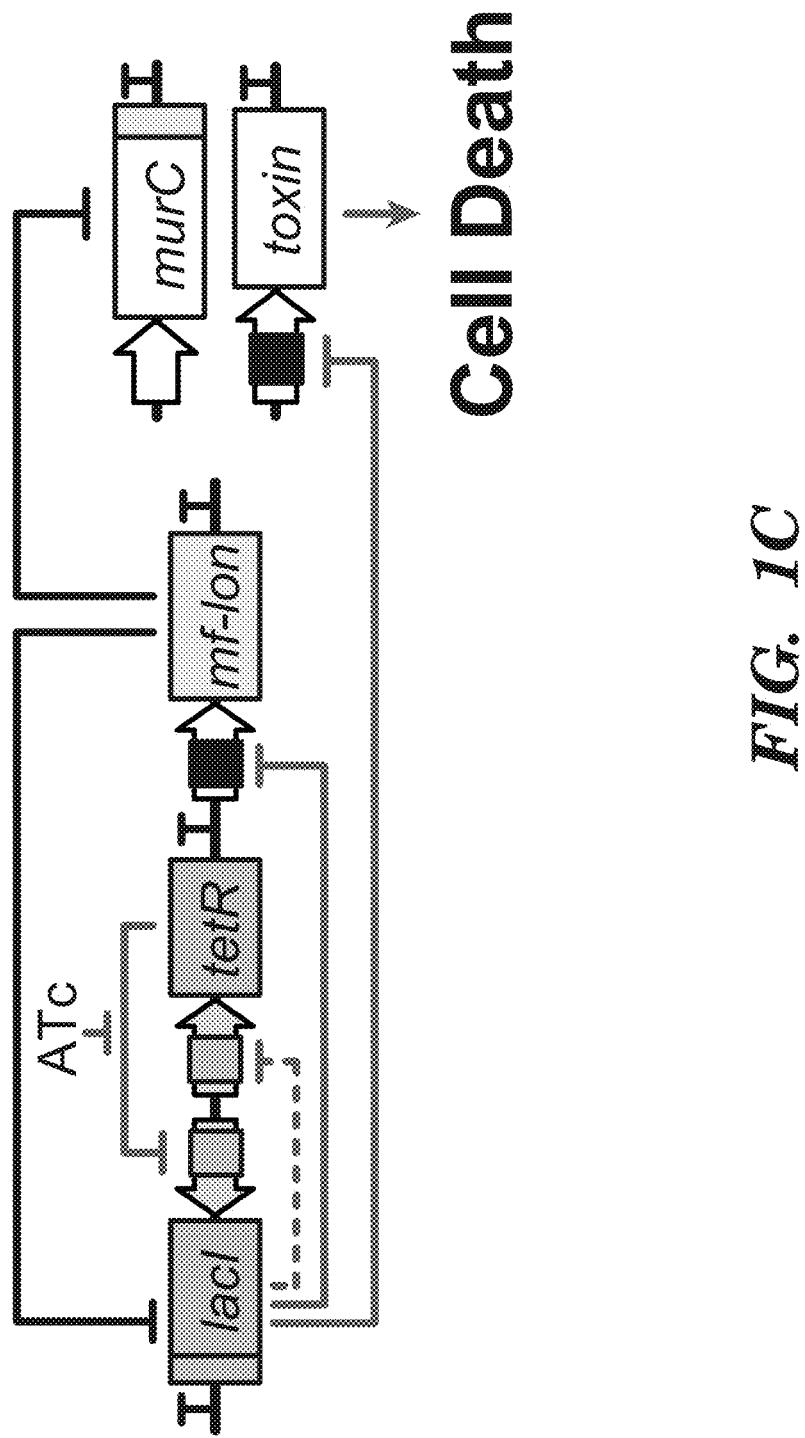
Figure 1C:
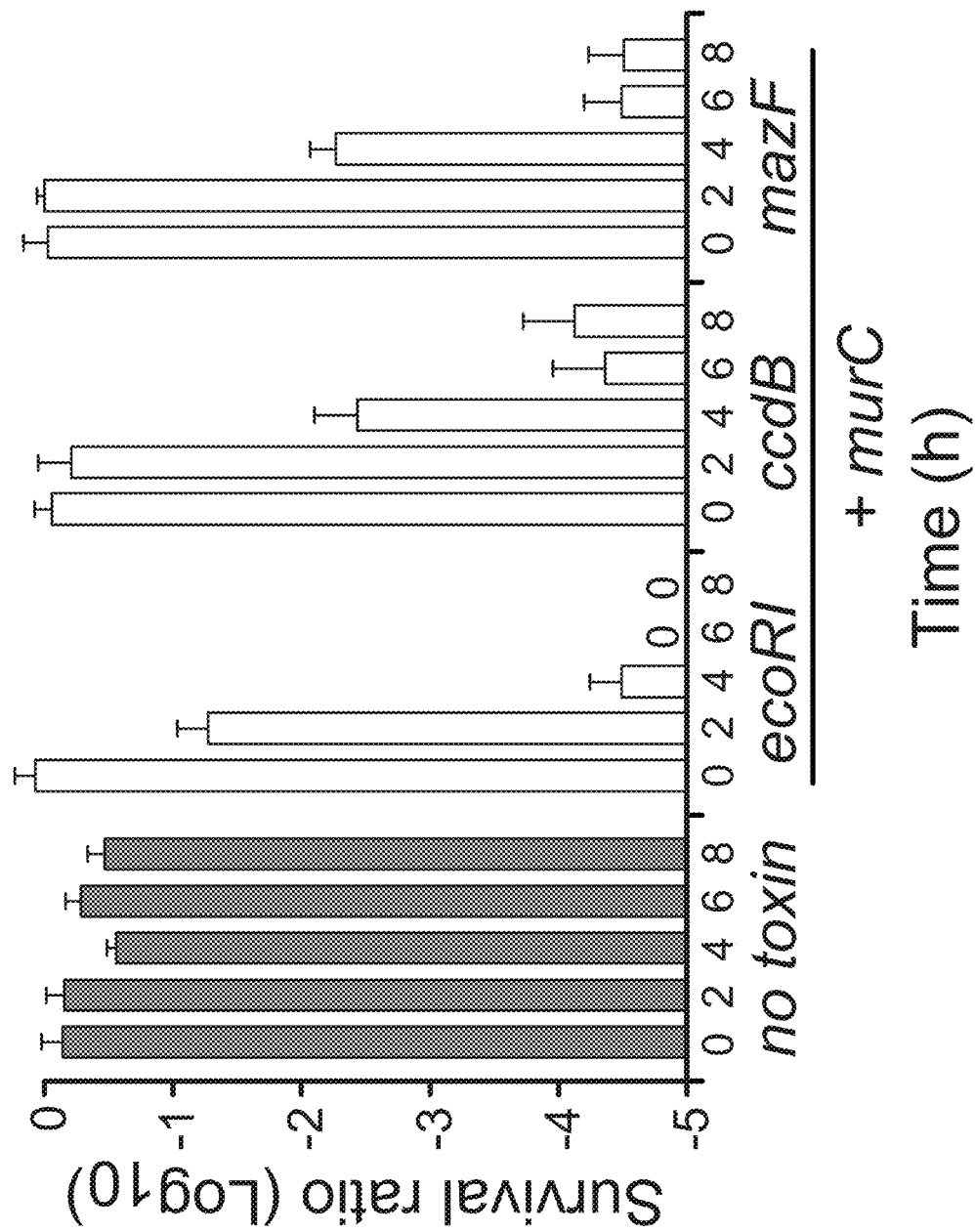
Figure 2:
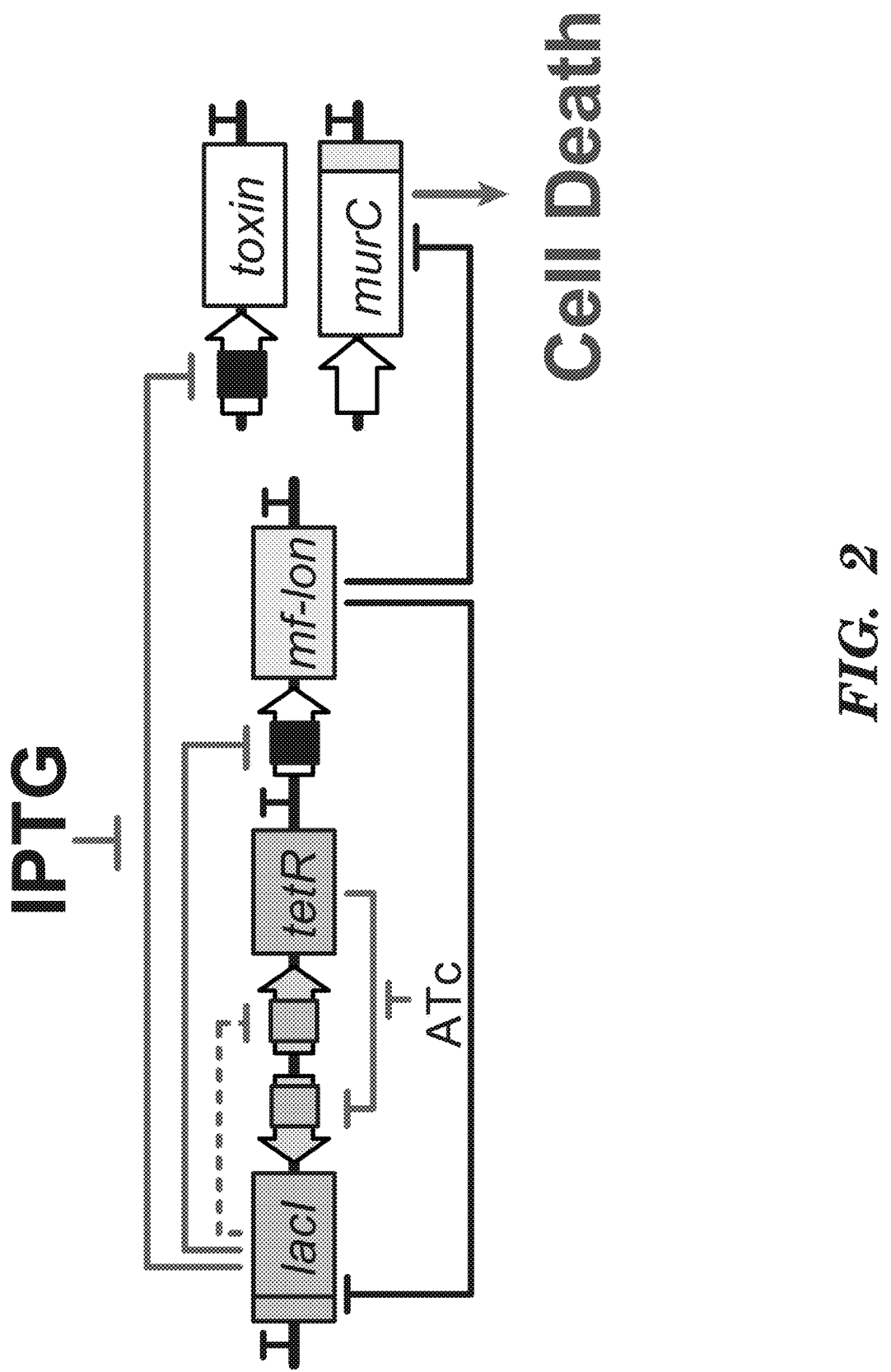
FIG. 2 depicts a fail-safe mechanism for Deadman circuit activation. To demonstrate active control over host cell viability, cells grown under survival conditions (with ATc) were exposed to 1 mM IPTG to directly induce EcoRI and mf-Lon expression. Cell viability was measured by CFU count and is displayed as a ratio of cell survival with and without IPTG.
Figure 2:
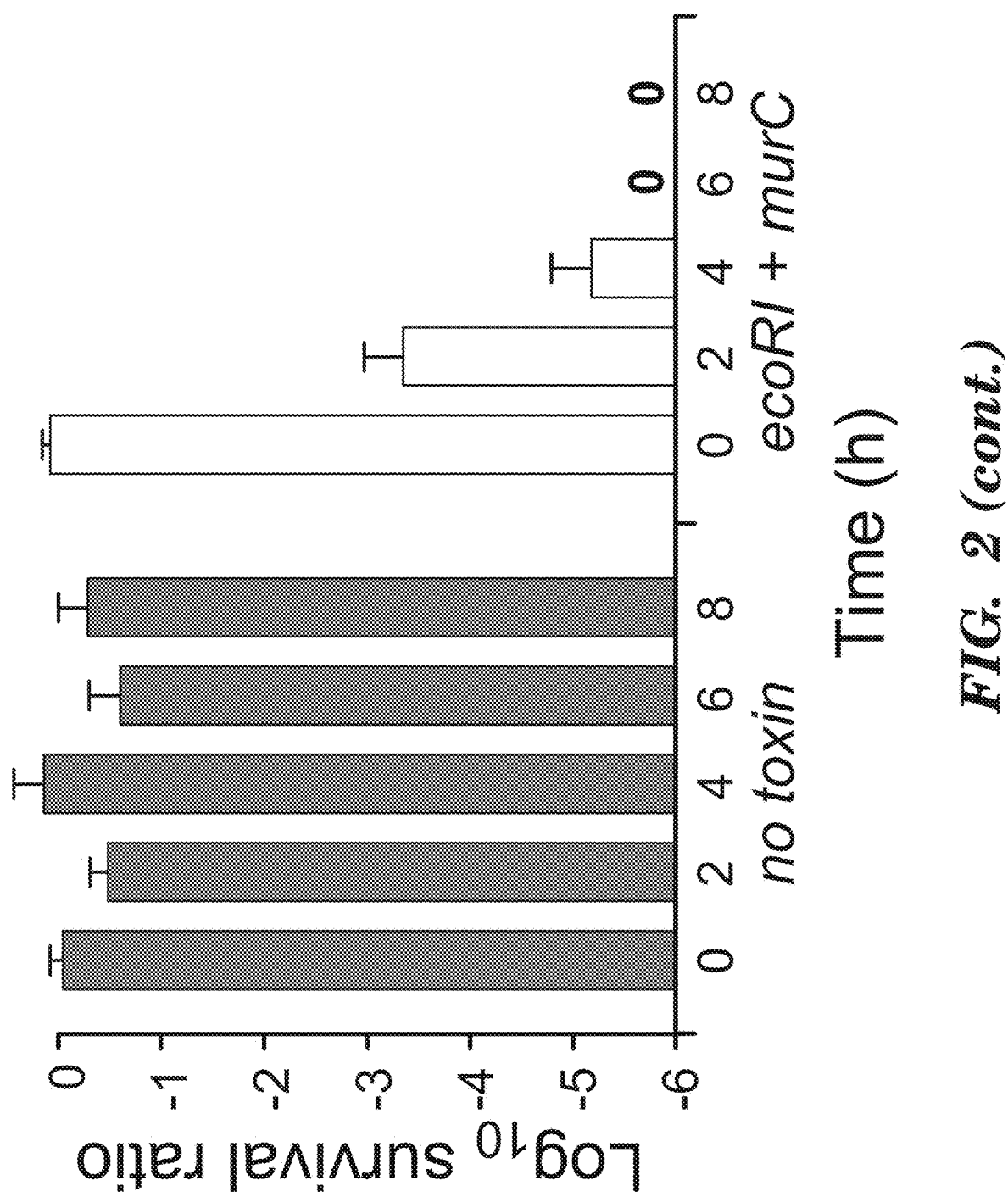

To determine if the toxin- and mf-Lon-mediated killing mechanisms produce synergistic effects, Deadman circuits were created containing each of the toxins in combination with the mf-Lon-MurC targeting module (FIG. 1C). In each instance, the combinatorial approach provided more effective biocontainment, and in particular, coordinated EcoRI expression and mf-Lon-mediated MurC degradation resulted in cell killing below the limit of detection (survival ratio <1×10$^{-7}$) 6 hours after removal of ATc (FIG. 1C). Furthermore, the Deadman circuit's design provides an additional fail-safe mechanism which bypasses the circuit's sensor system to directly activate toxin expression to cause cell death. Direct derepression of the subordinate TF, in this case derepression of LacI with isopropyl β-D-1-thiogalactopyranoside (IPTG), activates toxin production and cell death irrespective of the presence of the programmed survival signal (FIG. 2).

Passcode Kill Switches
Hybrid Transcription Factor Design

To extend the versatility and modularity of this system, a second circuit, called the Passcode circuit, was built which uses hybrid TFs to expand the range and complexity of environmental signals used to define biocontainment conditions. This survival "passcode" can be easily reprogrammed to restrict cell growth to a new environment or to limit knowledge of the growth conditions to authorized personnel.

In one aspect, a "passcode" system that renders cell growth restricted to the presence of a predetermined set of at least two selected agents, includes one or more nucleic acid constructs encoding expression modules comprising: i) a toxin expression module that encodes a toxin that is toxic to a host cell, wherein sequence encoding the toxin is operably linked to a promoter P1 that is repressed by the binding of a first hybrid repressor protein hRP1; ii) a first hybrid repressor protein expression module that encodes the first hybrid repressor protein hRP1, wherein expression of hRP1 is controlled by an AND gate formed by two hybrid transcription factors hTF1 and hTF2, the binding or activity of which is responsive to agents A1 and A2, respectively, such that both agents A1 and A2 are required for expression of hRP1, wherein in the absence of either A1 or A2, hRP1 expression is insufficient to repress toxin promoter module P1 and toxin production, such that the host cell is killed. In this system, hybrid factors hTF1, hTF2 and hRP1 each comprise an environmental sensing module from one transcription factor and a DNA recognition module from a different transcription factor that renders the binding of the respective DRM sensitive to the presence of an environmental agent, A1, or A2, that is different from that which the respective DRM binds in nature.

The passcode approach was tested using hybrid TFs designed from members of the LacI/GalR families. To build hybrid LacI family TFs, the boundaries of the environmental sensing modules (ESMs) and DNA recognition modules (DRMs) found in LacI family members were first identified. (FIG. 3A and FIGS. 12-15). Hybrid TFs were generated that use the small molecule input defined by the hybrid's ESM to regulate the promoter defined by the hybrid's DRM [25,26] (FIG. 3A and FIGS. 16A-16C).

Figures 3A, 3B:
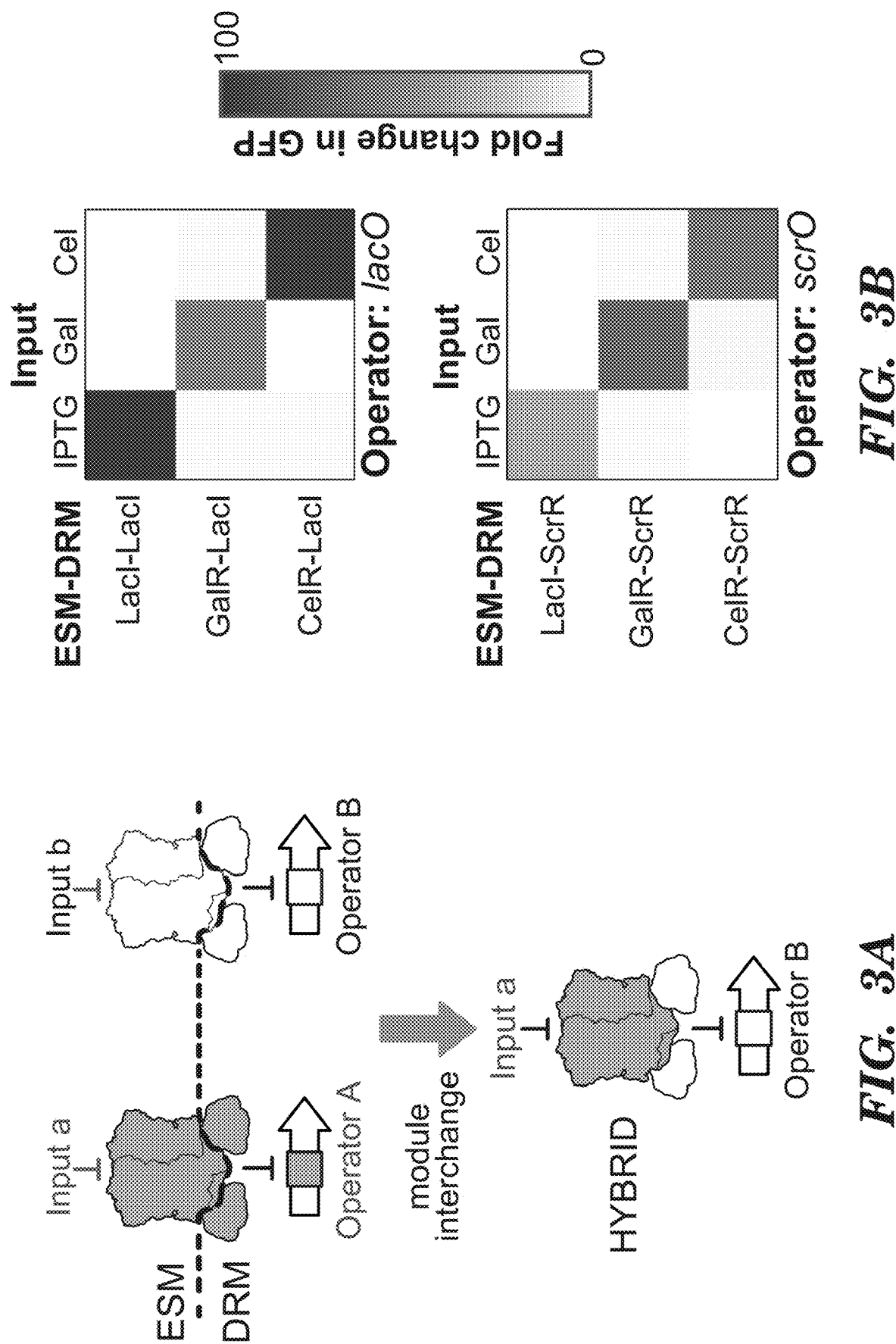
FIGS. 3A-3B demonstrate hybrid transcription factor (TF) construction and characterization.
Figure 16C:
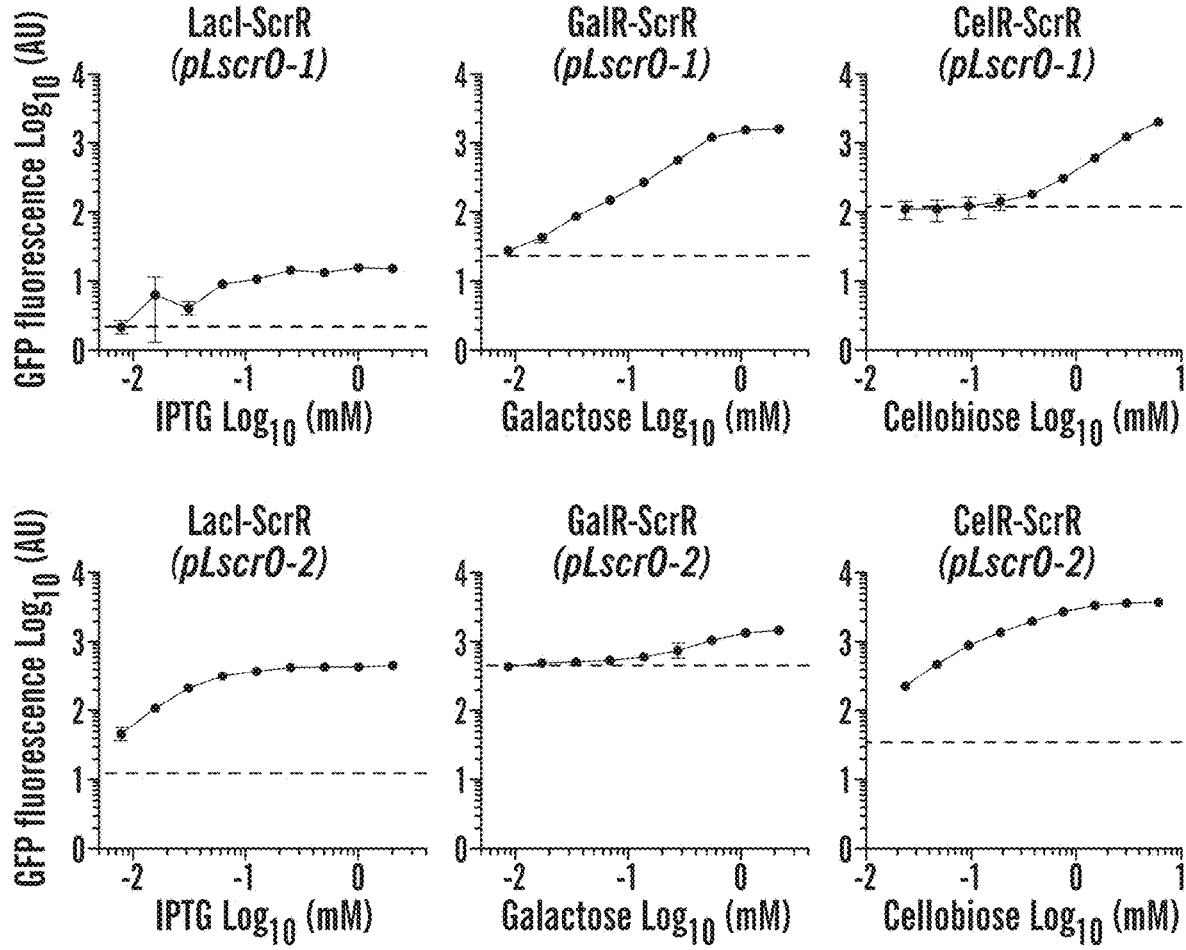
Figure 17:
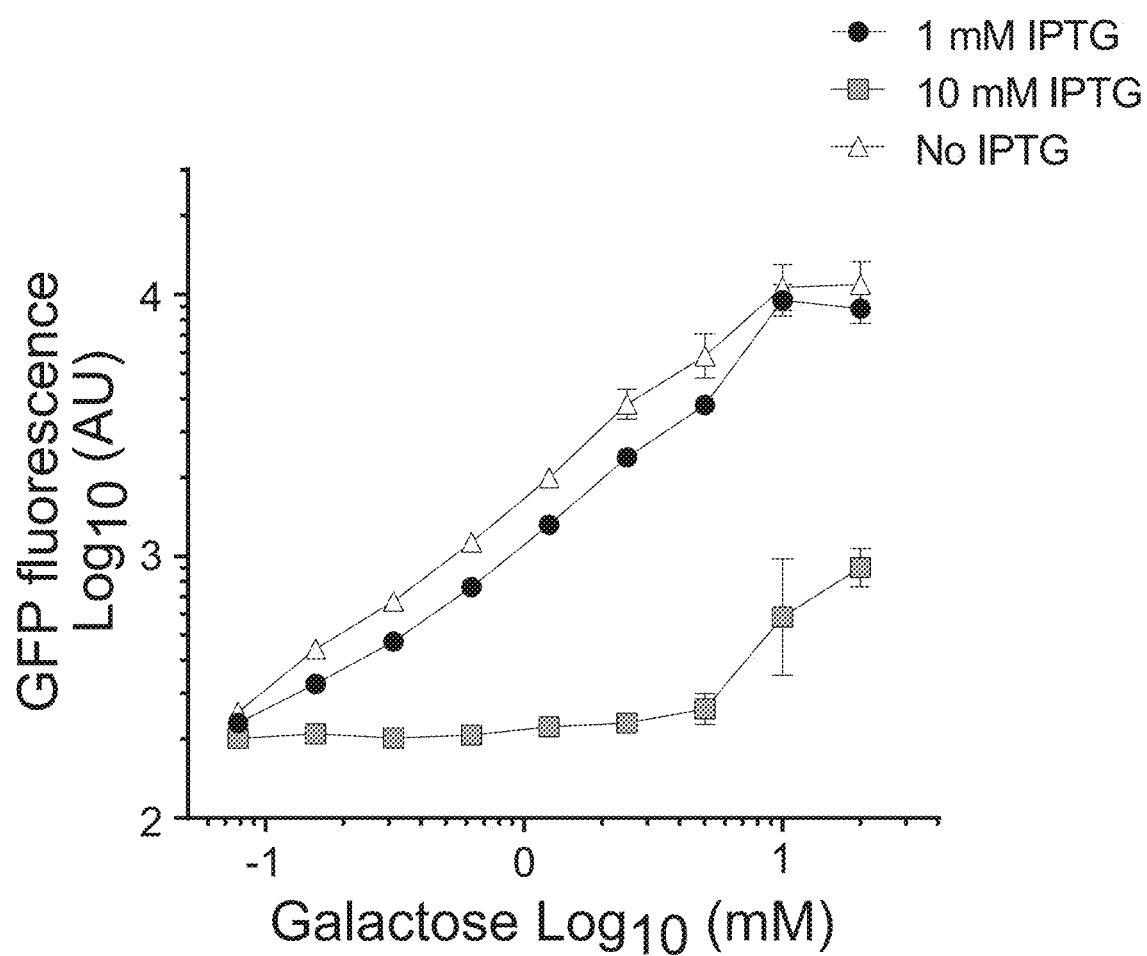
FIG. 17 depicts GalR-LacI activity in the presence of IPTG. Cells containing GalR-LacI and pLlacO-driven gfp gene were exposed to a range of galactose concentrations in the presence of 0, 1, or 10 mM IPTG. GFP levels in these cells were assessed by flow cytometry after 8 hours. Data points represent the mean±S.D. of three biological replicates.
Figure 18:
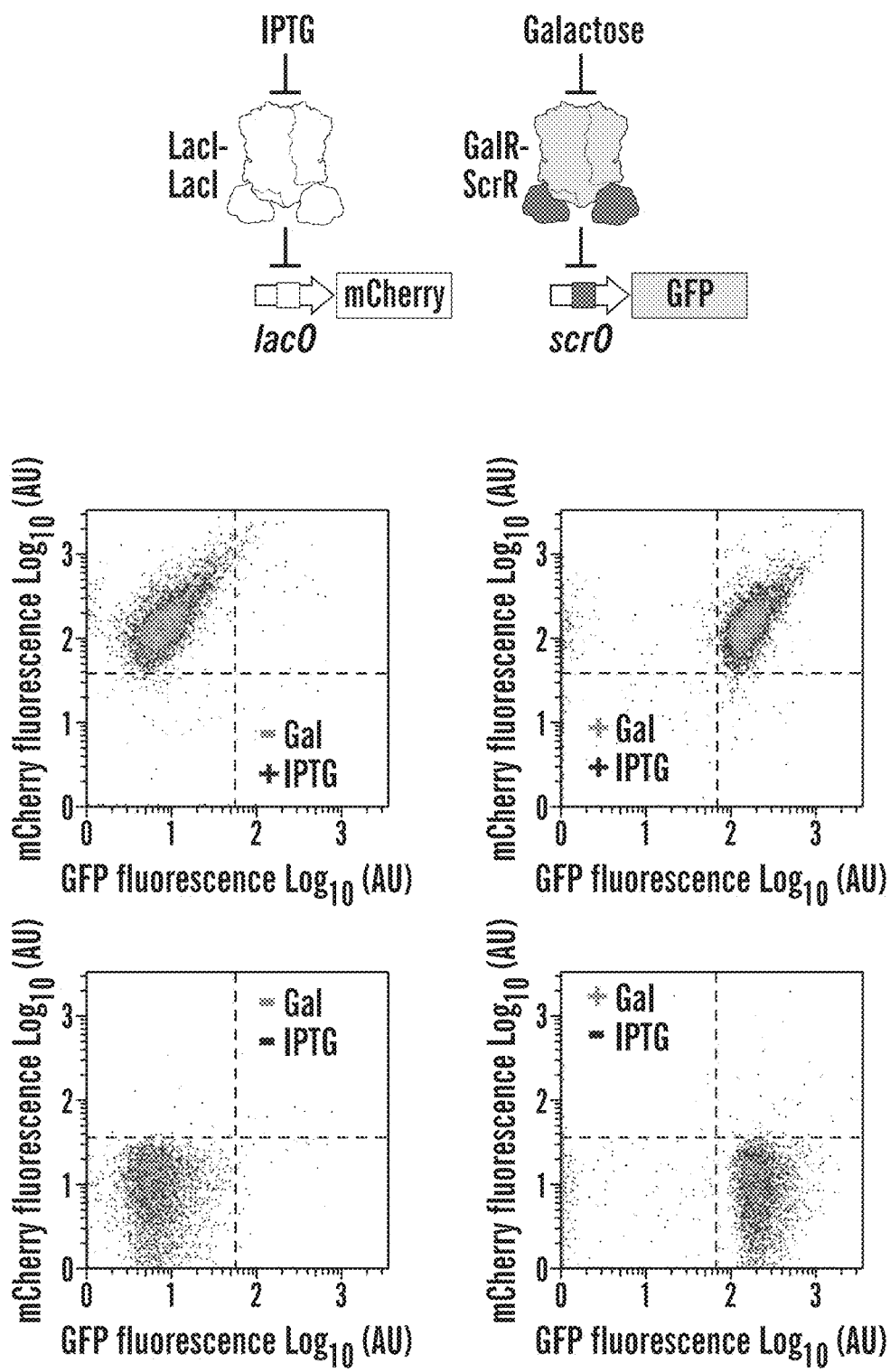
FIG. 18 demonstrates GalR-ScrR hybrid regulation is interoperable with LacI regulation. LacI-LacI and GalR-ScrR were expressed in cells containing pLlacO-1-mcherry and pLscrO-1-gfp reporters. Cells were exposed to IPTG (1 mM) and/or galactose (20 mM) for 1 hour and assayed for GFP and mCherry expression by flow cytometry.
Figure 19:
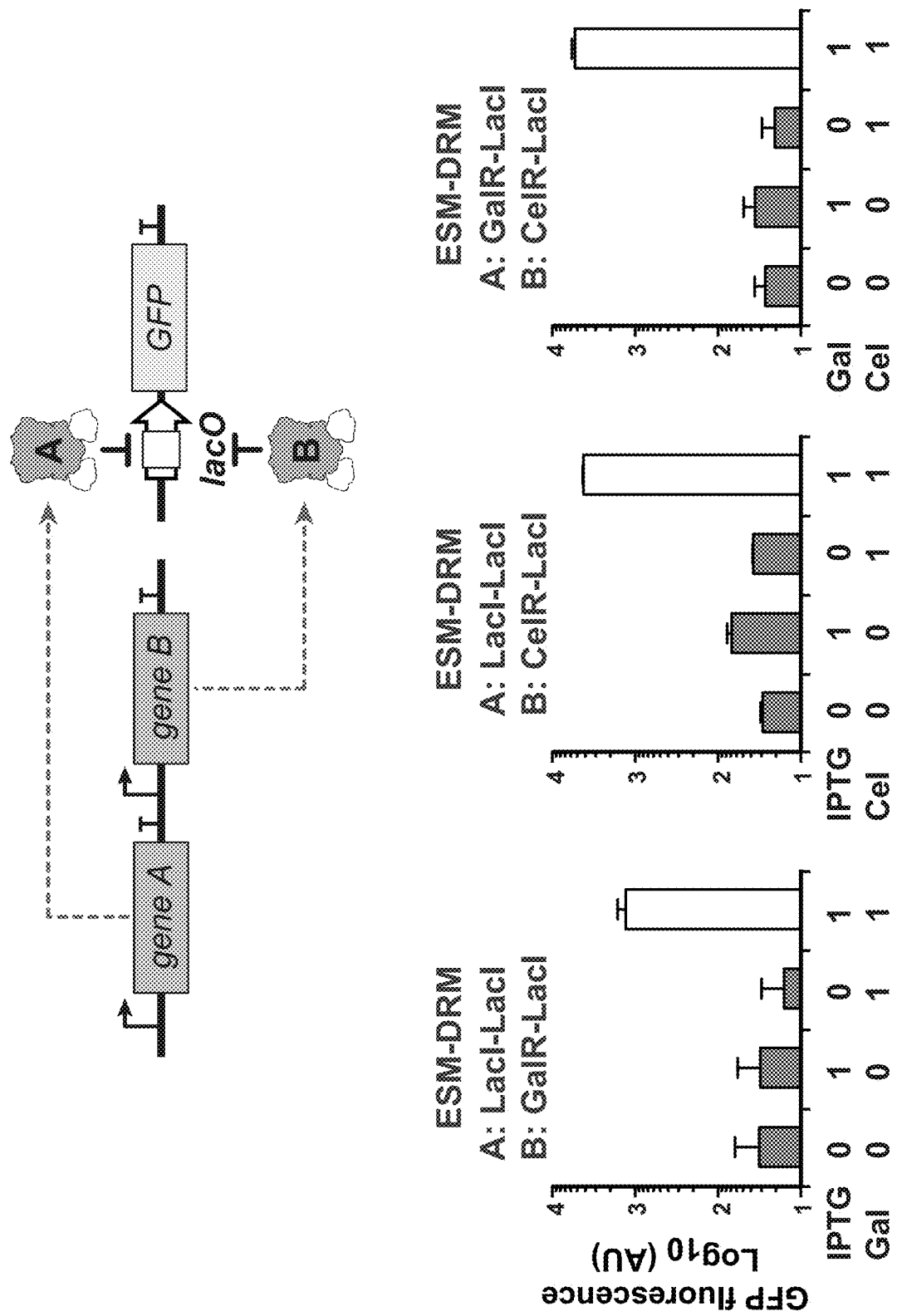
FIG. 19 demonstrates generation of AND logic gates using hybrid TFs. For each AND logic gate, two TFs were expressed in cells harboring the pLlacO-gfp reporter. Cells were treated with the indicated inducers for 3 hours before GFP fluorescence was measured by flow cytometry. Data points represent the mean±S.D. of three biological replicates.

To construct the hybrid TFs, we used the cellobiose-responsive TF CelR from *Thermobifida fusca* and the galactose-responsive TF GalR and IPTG-responsive LacI from *E. coli*. We fused the ESMs from CelR and GalR to the DRM of LacI to generate the hybrid TFs CelR-LacI and GalR-LacI. To test their functionality, these hybrid TFs or native LacI were used to control GFP expression from a promoter containing lacO operator sites recognized by the LacI DRM. The hybrid TFs allowed strong GFP expression upon exposure to the small molecule input defined by their ESM and showed almost no response to the other inputs (FIG. 3A and FIG. 16B). We fused the LacI, GalR and CelR ESMs to the DRM of ScrR from *Klebsiella pneumoniae* and used the resulting hybrid TFs to regulate a promoter containing scr0 operator sites. As predicted from their design, these hybrid TFs only respond to the input defined by their ESM (FIG. 3B and FIG. 16C), although it is interesting to note that the GalR ESM shows distinct inhibition by high levels of IPTG as seen by Shis et al.[27] (FIG. 17). Importantly, the DRMs used in these hybrid TFs provided similar specificity, as they regulated promoters containing their cognate operator sites but not other LacI family operator sites (FIG. 18). Similar to work by Shis et al.[27], we found that co-expression of hybrid TFs containing the same DRM could be used to regulate a single promoter, creating an AND logic gate function (FIG. 19).

Development of the Passcode Kill Switches

Figure 20A:
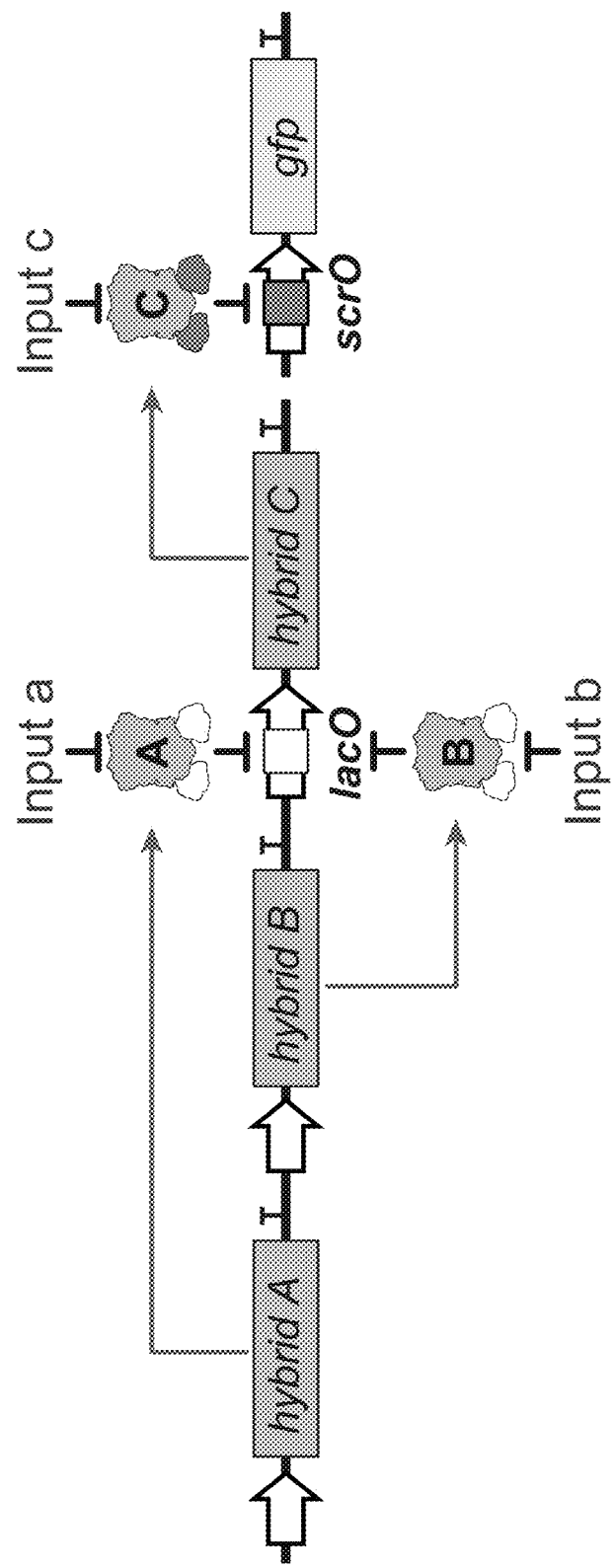
FIGS. 20A-20C demonstrate exemplary passcode circuit control of GFP expression.
Figure 20B:
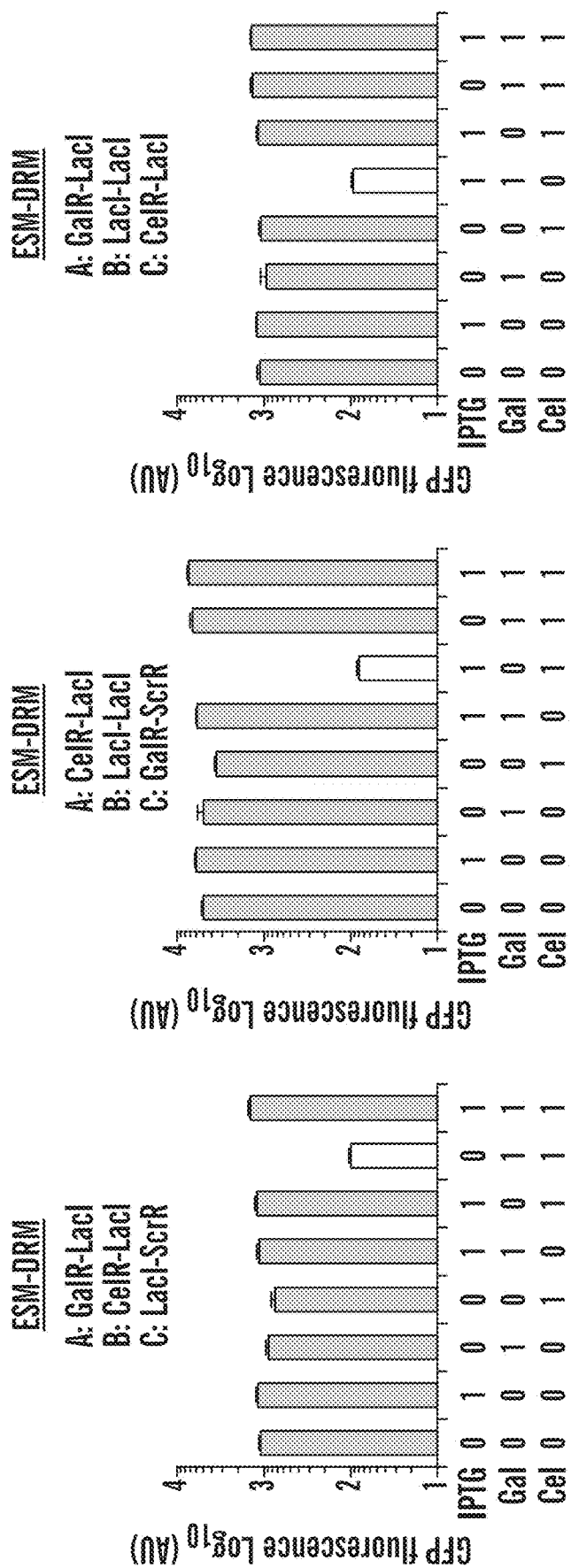
Figure 20C:
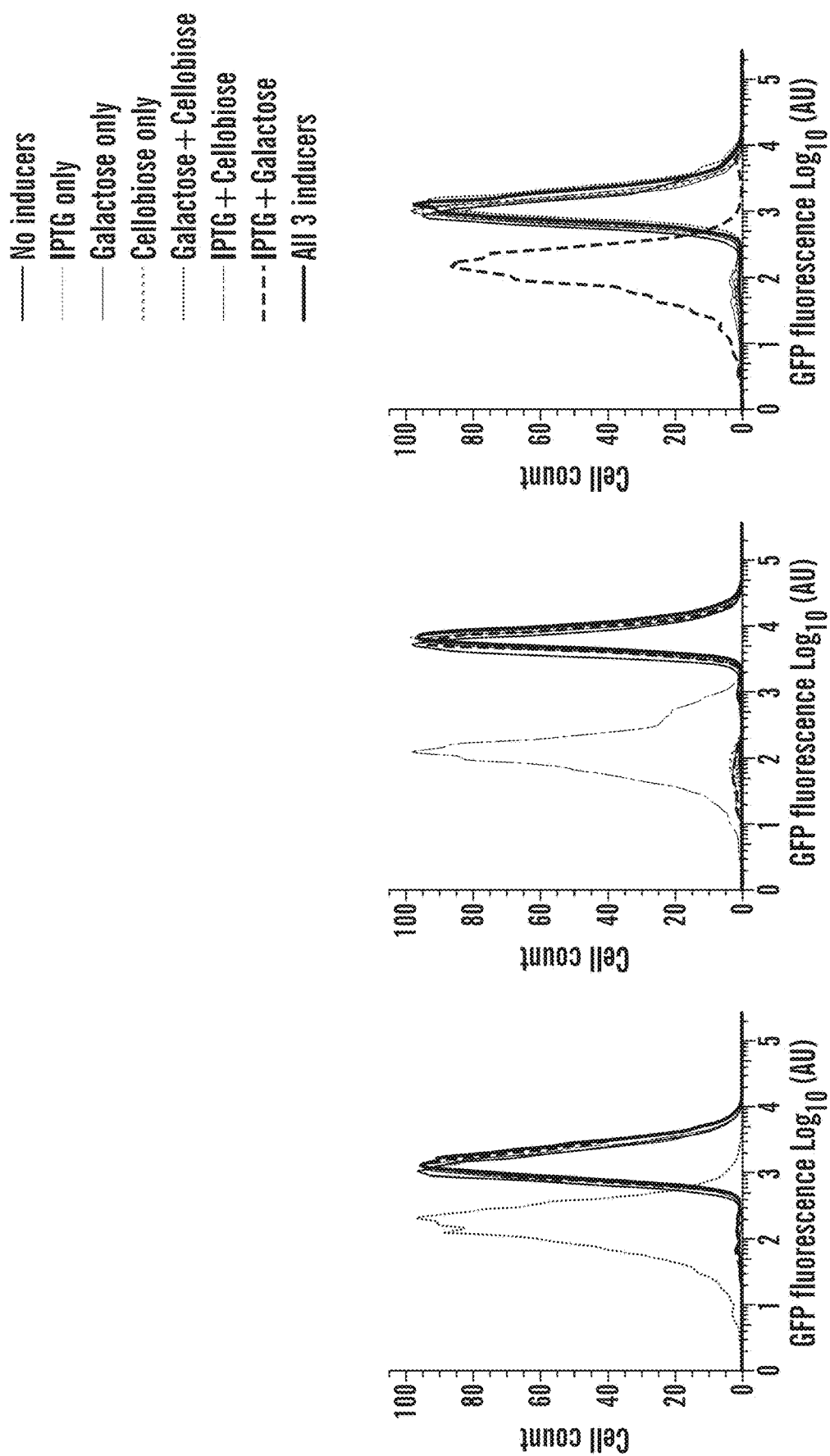

We used these hybrid TFs to create a series of Passcode circuits that contain a single transcriptional architecture but respond to distinct combinations of environmental inputs to control gene expression and cell survival. As shown in FIGS. 20A-20C, the Passcode circuits contain the output module (in this case, gfp) under control of a TF (hybrid C) whose expression is controlled by an AND gate formed by two TFs (hybrid A and hybrid B). This serial arrangement, made possible by the orthogonality of the hybrid DRMs and ESMs, creates the condition that both of the inducers recognized by hybrid A and hybrid B (inputs a and b, respectively) must be present to allow expression of hybrid C to repress gfp expression. Loss of input a or input b or the presence of input c allows gfp expression, causing cell death if gfp is replaced by a toxin gene.

Figure 4A:
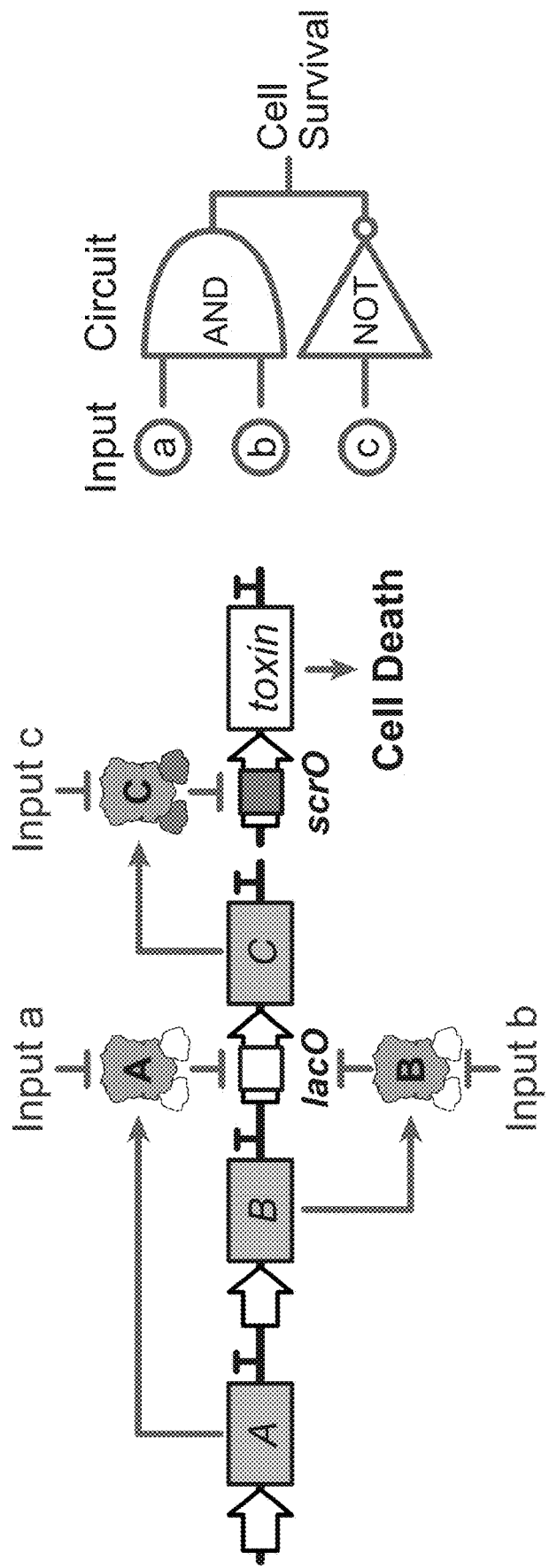
FIGS. 4A-4B depict an exemplary embodiment of a "Passcode kill switch.

To test the functionality and modularity of this circuit architecture, we created three exemplary embodiments of the Passcode circuit that respond to different combinations of input signals to control output expression (FIG. 4A). For example, in one Passcode circuit (FIG. 4B, left column), we used GalR-LacI (A) and CelR-LacI (B) to control expression of LacI-ScrR (C), which in turn represses toxin expression. In this circuit, loss of galactose (input a) or cellobiose (input b) allows GalR-LacI or CelR-LacI to bind the lacO operator, blocking LacI-ScrR expression, thereby enabling toxin expression and causing cell death. Any exposure to IPTG (input c) releases LacI-ScrR repression of toxin expression, thereby killing the cell as well. Importantly, the passcode combinations for cell survival and cell death can be reprogrammed by rearranging the ESMs of the three TFs to rewire the connections between the environmental sensing and transcriptional regulation, in different embodiments.

Figure 4B:
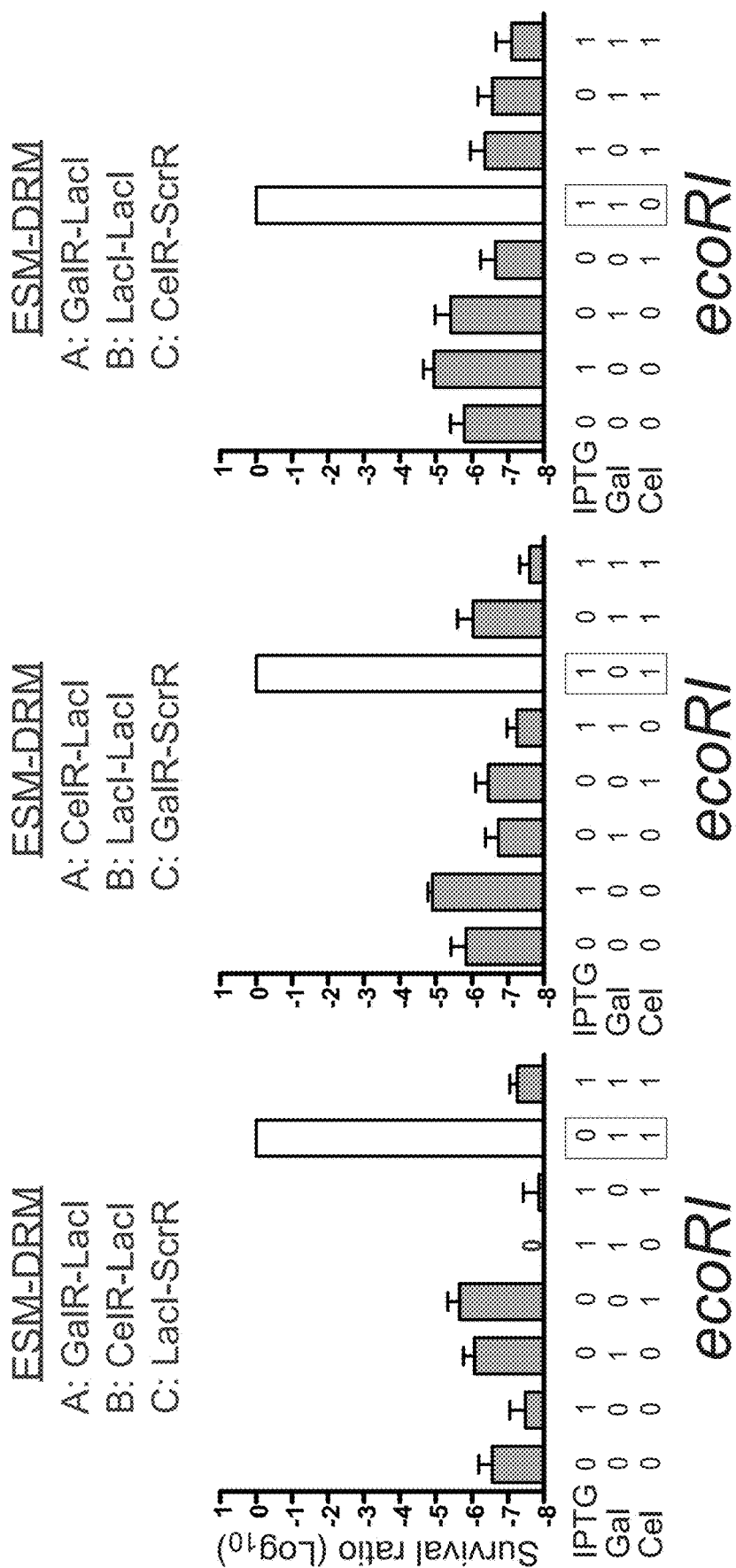
Figure 4B:
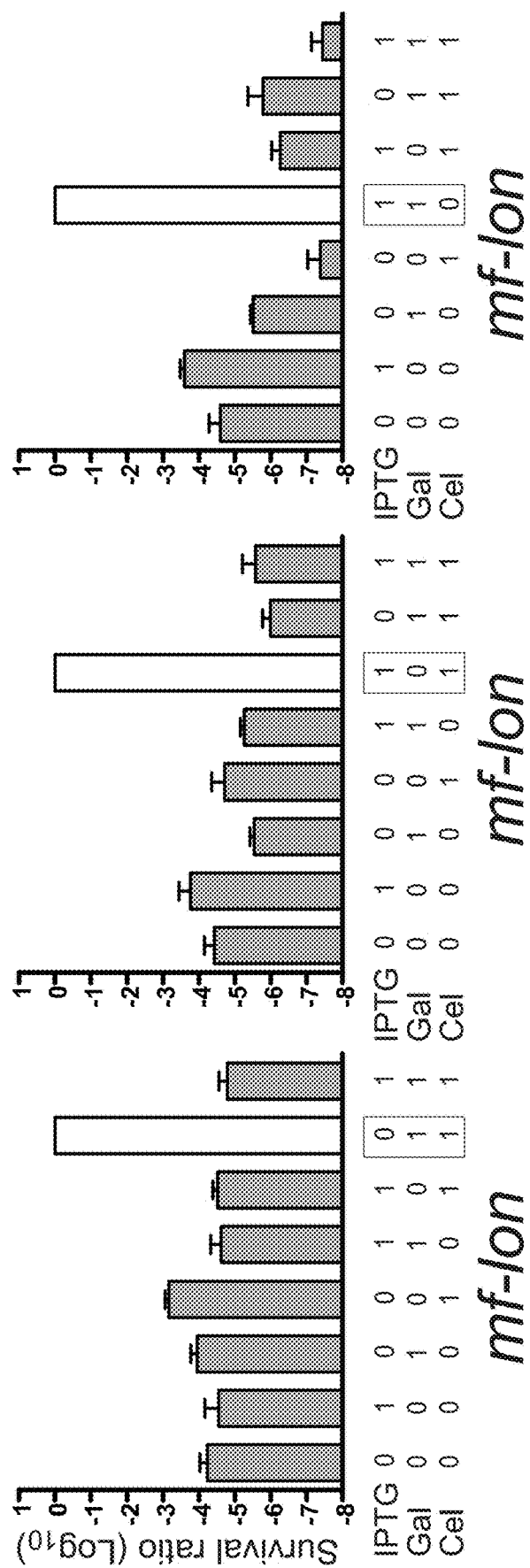
Figure 4B:
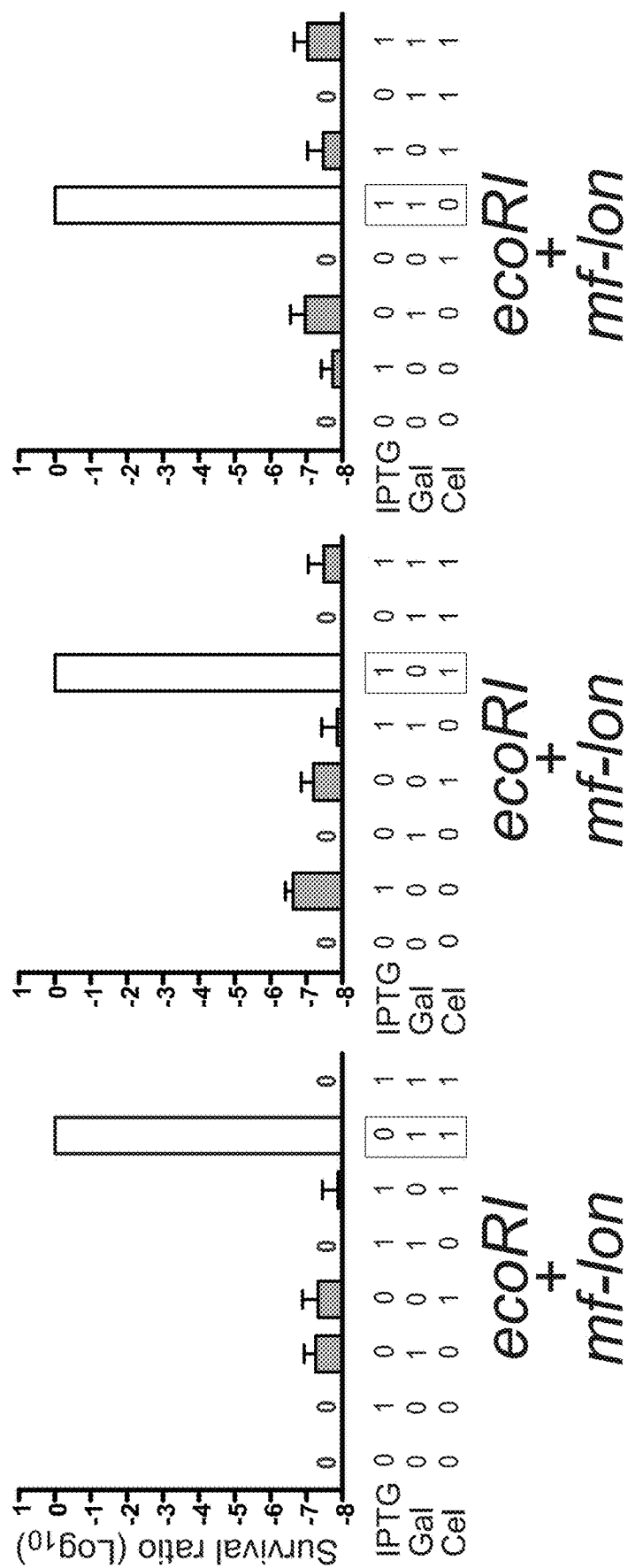
Figure 21:
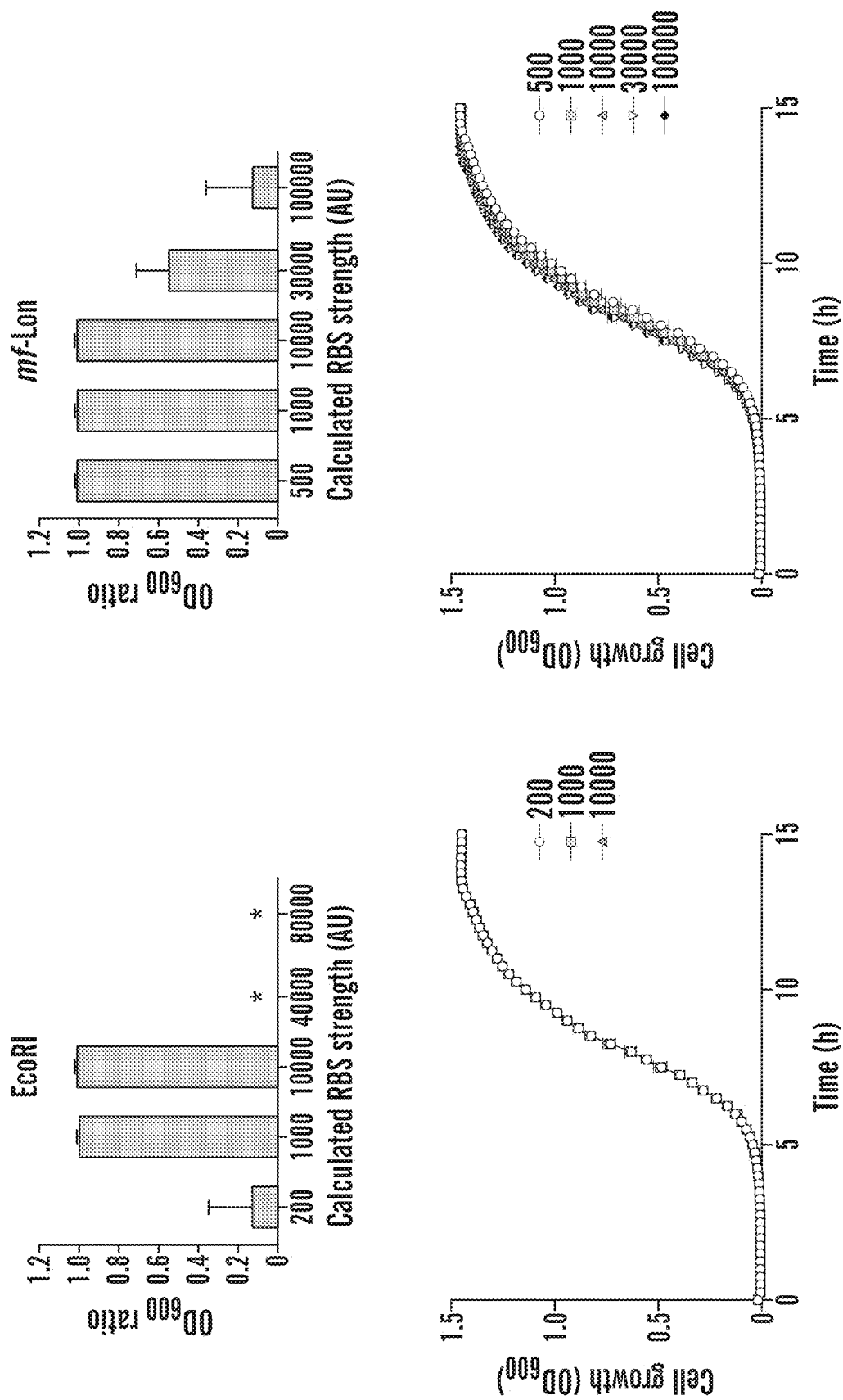
FIG. 21 depicts representative RBS strength analysis for Passcode toxin optimization. For CelR-ScrR dependent toxin expression, RBS sequences with a range of calculated translation initiation rates were used to control EcoRI and mf-Lon expression. Cells containing each RBS candidate were grown in the presence or absence of cellobiose (the death state and survival state, respectively), and the ratio of cell growth in these states was used to measure killing activity (OD600 ratio, top charts). Cell growth rate in the survival state (Cell growth, bottom charts) showed no distinct difference among the RBS candidates, and therefore RBS sequences that showed high killing activity were chosen for each toxin; 200 for EcoRI and 100000 for mf-Lon. "*" indicates RBSs that could not be cloned under survival conditions despite multiple attempts. Data points represent the mean±S.D. of three biological replicates.
Figure 22:
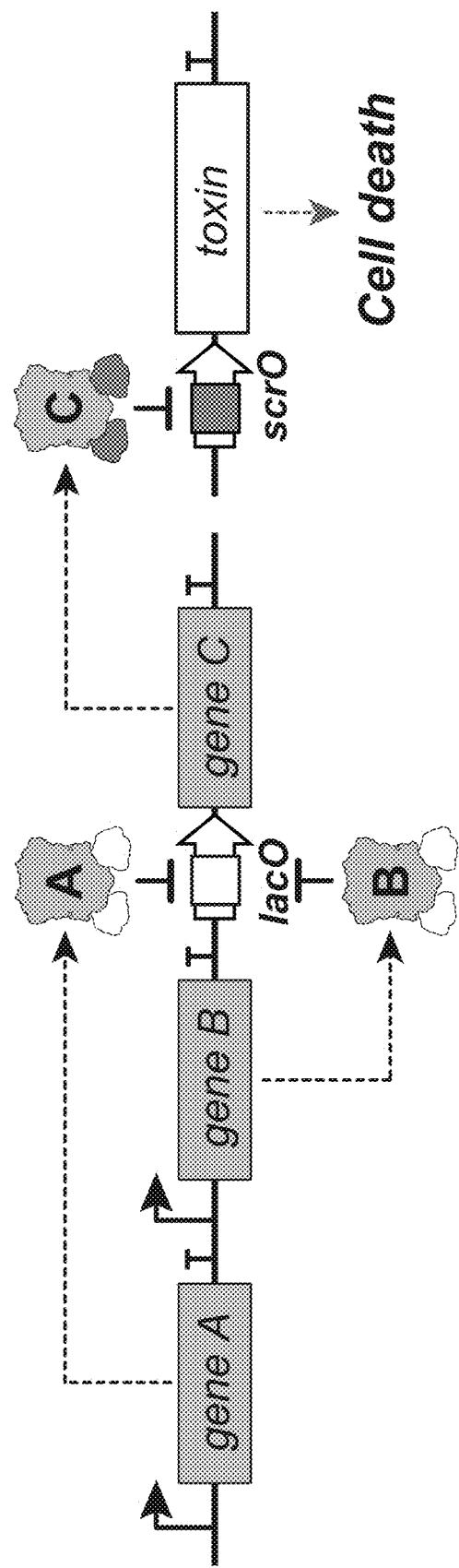
FIG. 22 depicts time-dependent cell killing by the Passcode kill switch. Cells containing the indicated version of the Passcode circuit were exposed to each of the eight combinations of the three small molecule inputs (IPTG, galactose, and cellobiose). Cell viability was measured by CFU count at the indicated times after exposure, and results are presented as the ratio of CFUs in each input condition to that in the survival condition that is unique for each Passcode circuit. Data points represent the mean±S.D. of three biological replicates.
Figure 22:
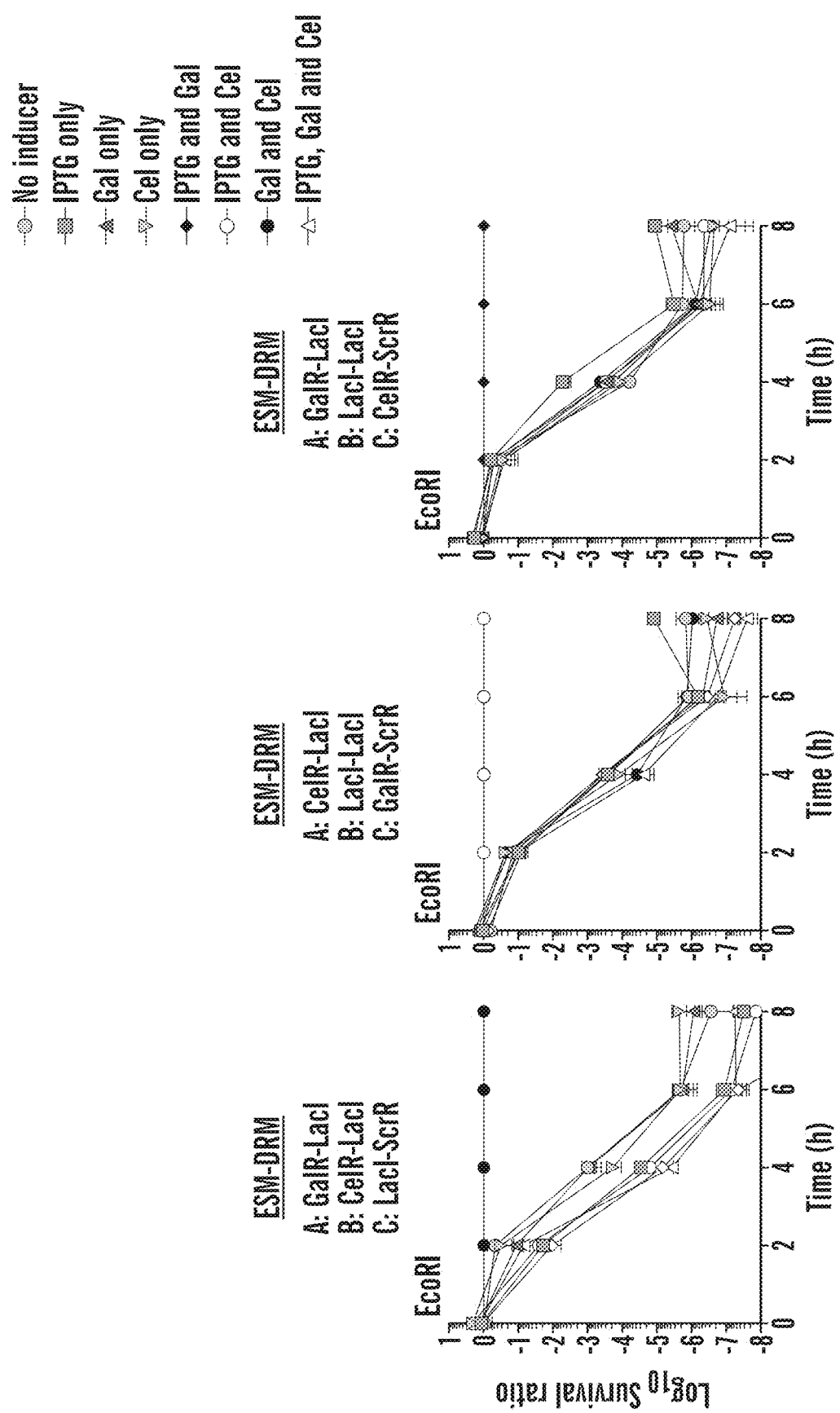
Figure 22:
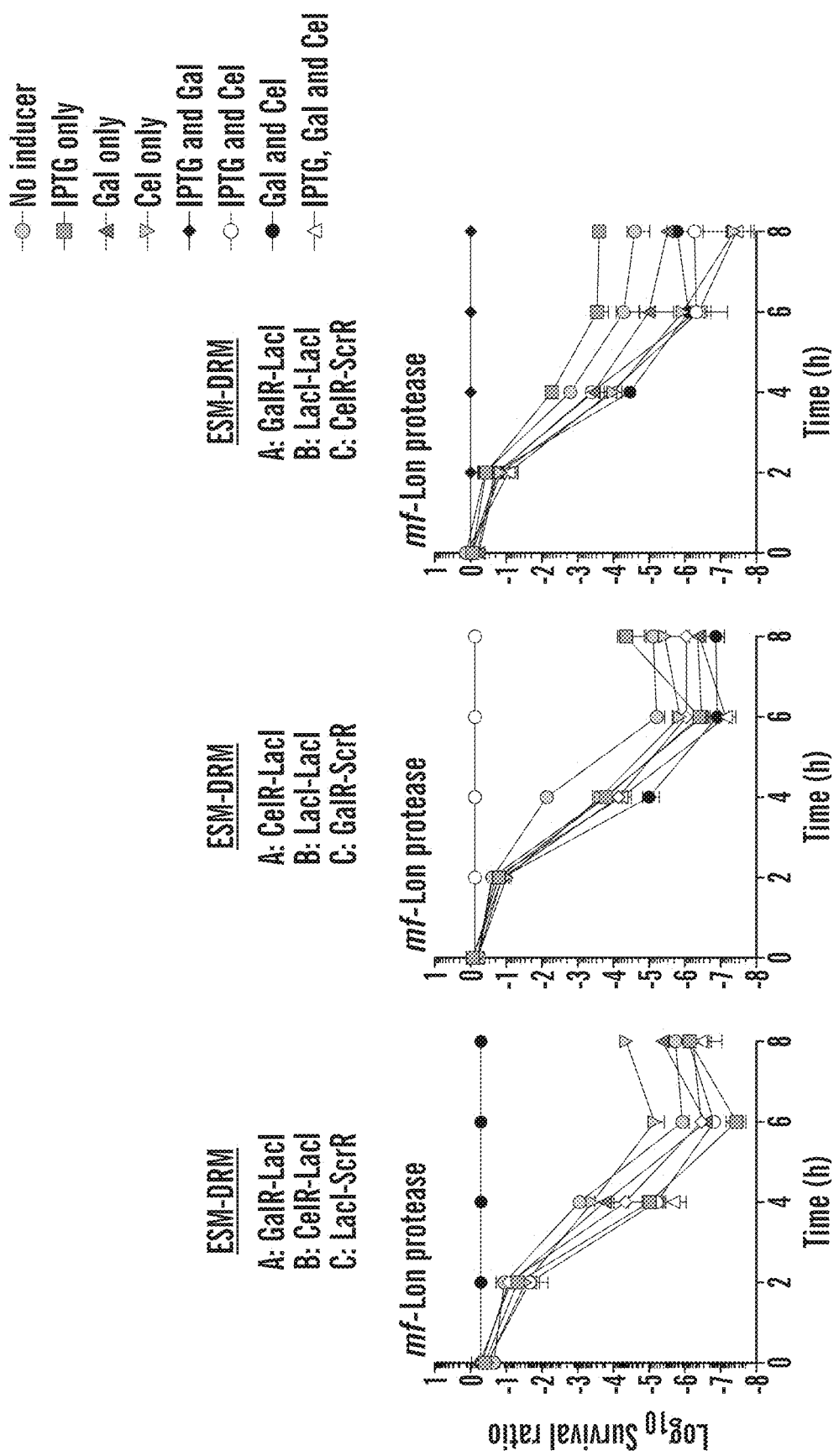
Figure 22:
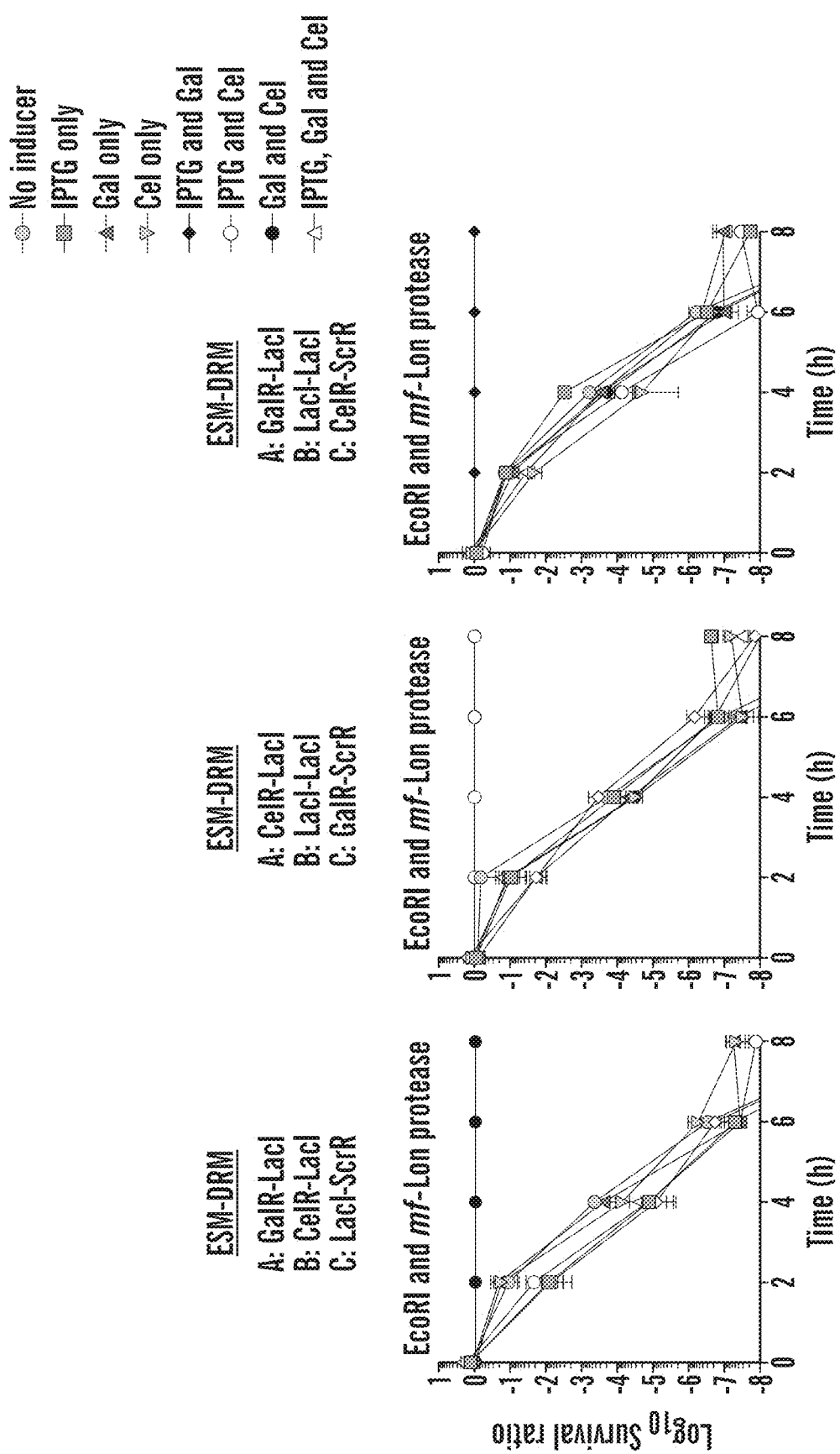

These Passcode circuits were first evaluated with GFP as the output module in all eight combinations of the three environmental inputs. All three circuits allowed high level GFP expression in all conditions except that designated by the desired three input combination (FIG. 20B), and single-cell fluorescence showed a monomodal population distribution under all conditions (FIG. 20C). GFP was then replaced with the ecoRI and mf-Lon-MurC toxin modules described for the Deadman switch above (FIG. 4A), and toxin expression levels were optimized by testing a range of calculated RBS strengths[24] (FIG. 21). Hybrid C, which directly controls toxin expression in the circuit, was also engineered in the same manner to optimize circuit performance (see Supplementary Methods). Each kill switch circuit was tested in *E. coli* using eight combinations of input signals, and cell survival was measured by CFU count at multiple time points (FIG. 22). As seen in FIG. 4B, only circuits that received the proper survival code allowed the host cells to survive (each survival condition is highlighted in green). Furthermore, inclusion of both the ecoRI and mf-Lon toxin modules in the Passcode circuit caused the cell survival ratio to drop below 1×10$^{-6}$ for all non-passcode conditions.

Circuit Stability

Figure 5A:
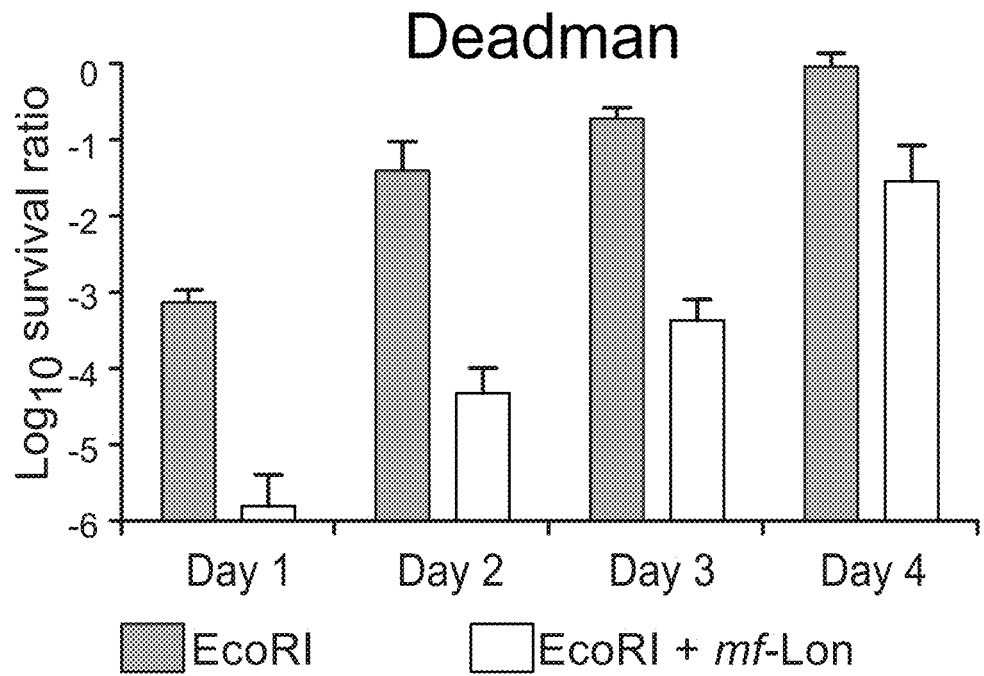
FIGS. 5A-5C demonstrate long-term circuit stability.
Figure 5B:
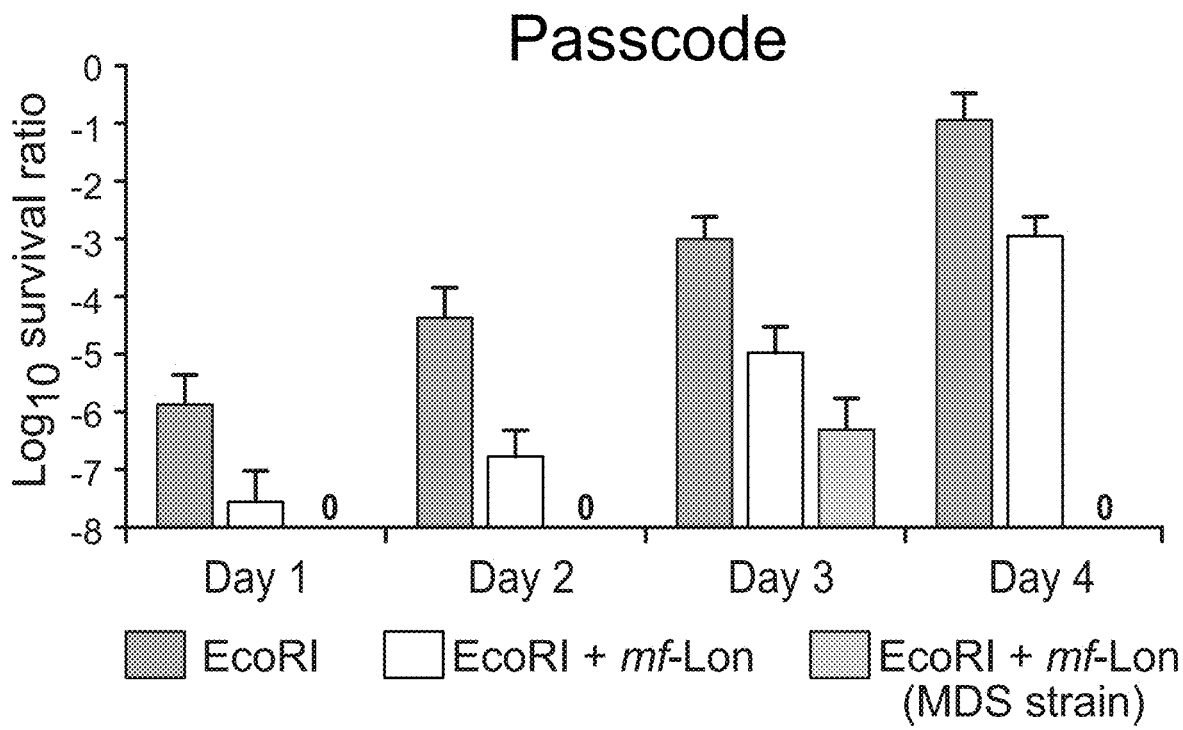
Figure 5C:
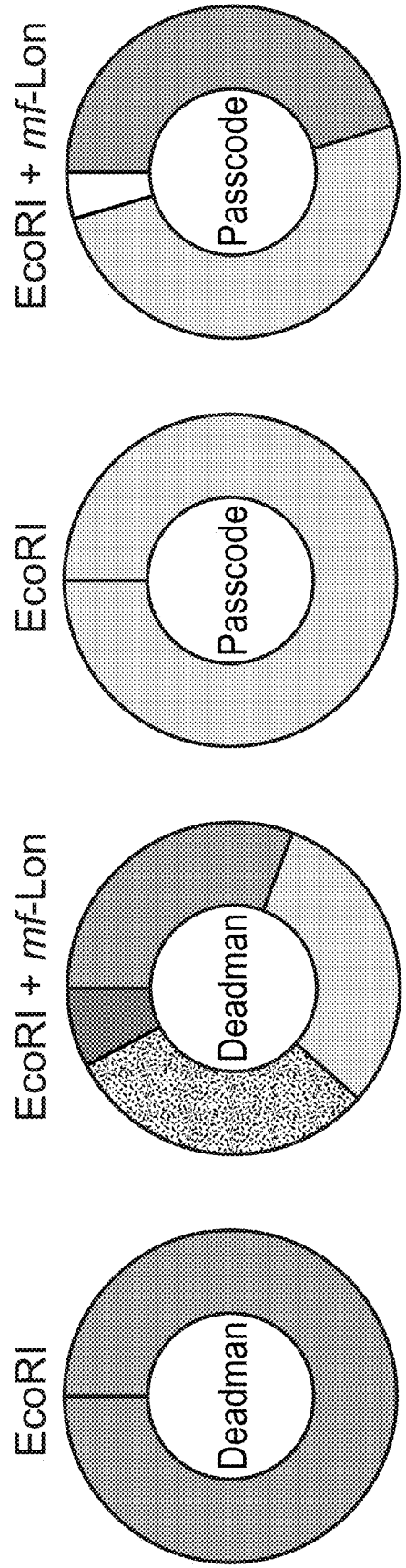
Figure 23:
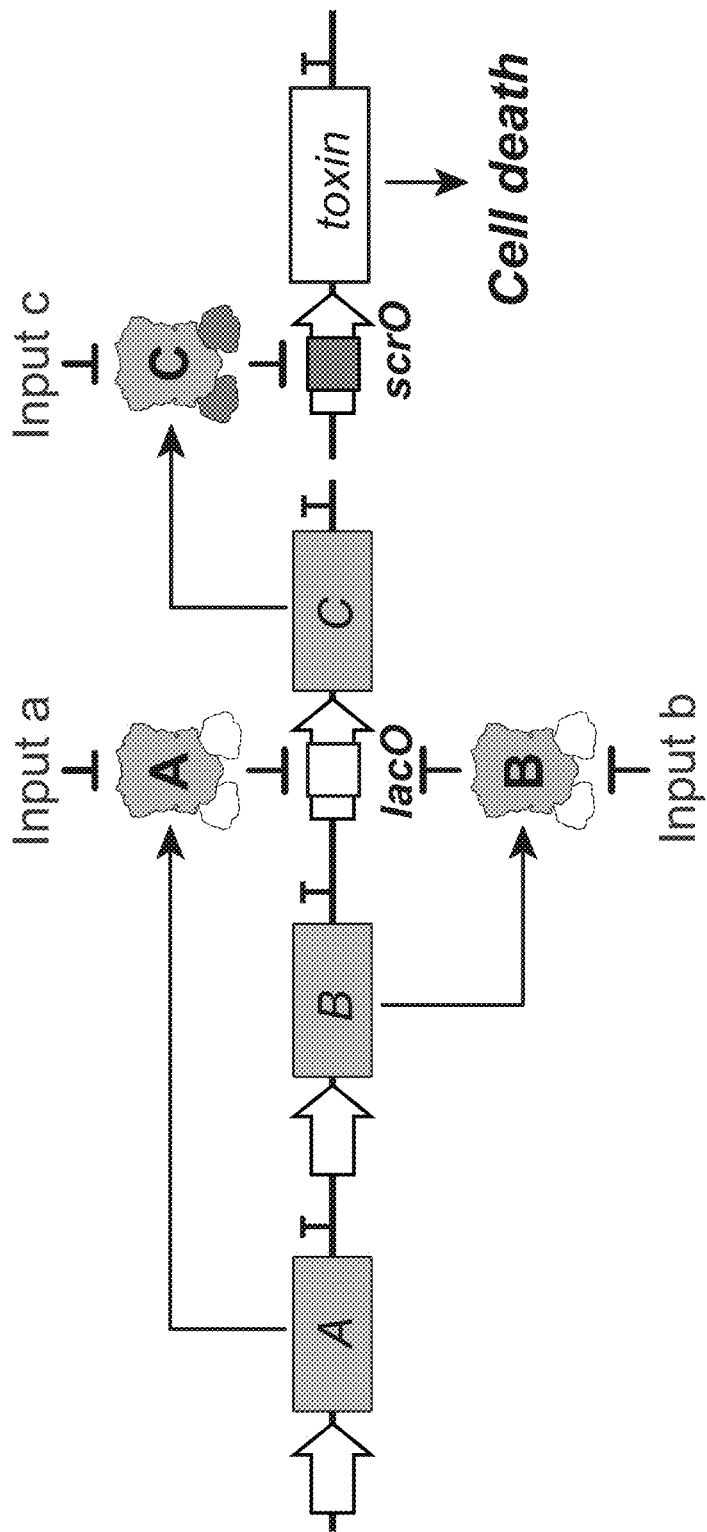
FIG. 23 depicts effect of long-term growth on the Passcode kill switches. Cells with Passcode kill switches containing one toxin (EcoRI) or two toxins (EcoRI and mf-Lon) were passaged in the survival condition unique to each Passcode circuit, and sub-populations of these cells were periodically switched to the death state by exposure to media with no inducers. Introduction of the two toxin Passcode circuits into E. coli strain MDS42pduΔrecA (MDS strain), which lacks recombinogenic and mobile genomic elements11, yielded a 3-5 log reduction in escapee frequency after 4 days. Cell viability was measured by CFU count after 8 hours of exposure to the death state and is presented as a ratio of surviving cells in the death state to those in the survival state at each time point. All strains also contain a deletion in lacI (ΔlacI) and a genomic murC-pdt#1 tag. Data points represent the mean±S.D. of six biological replicates.
Figure 23:
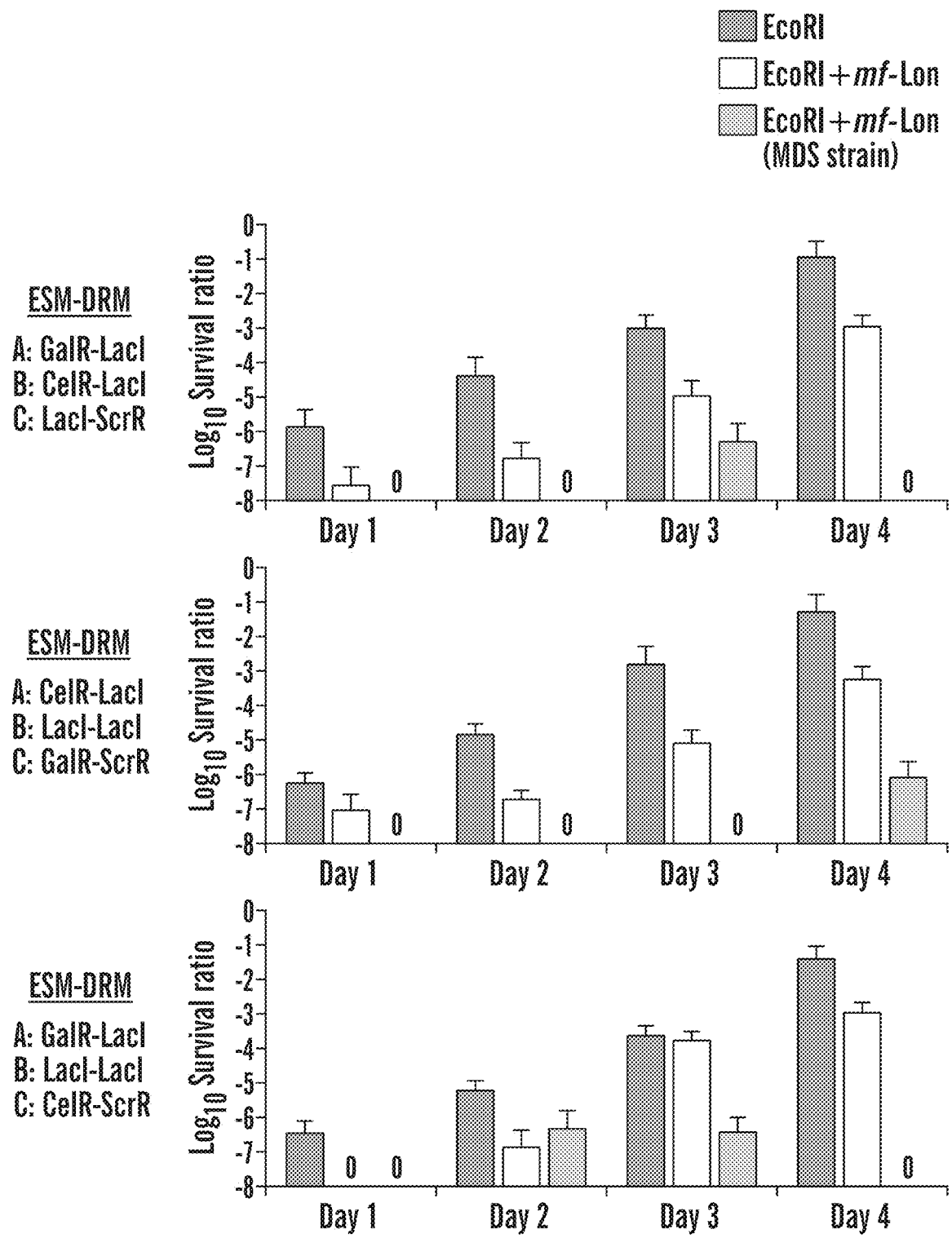
Figure 24A:
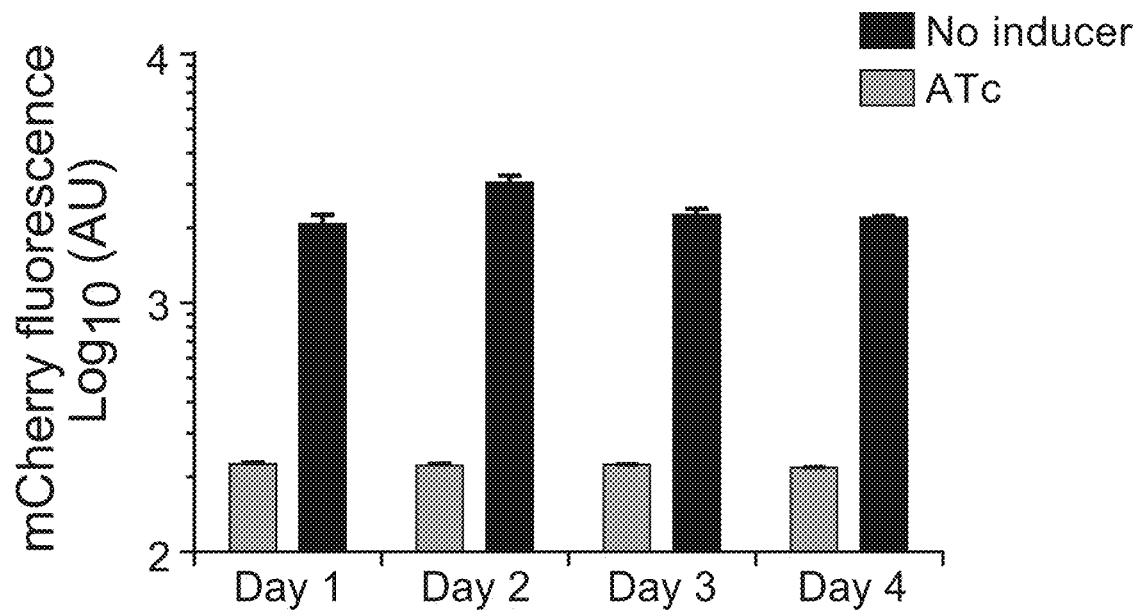
FIGS. 24A-24B demonstrate effects of long-term growth on the Deadman kill switches without toxin modules.
Figure 24B:
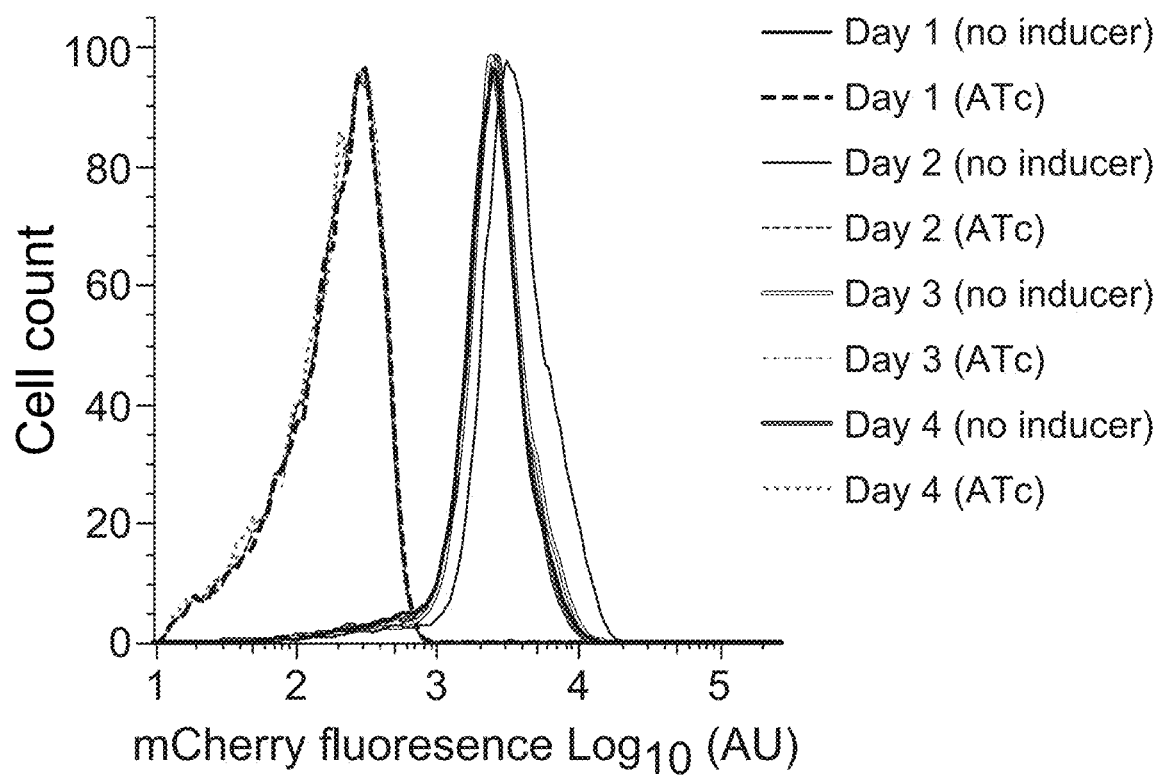
Figure 25:
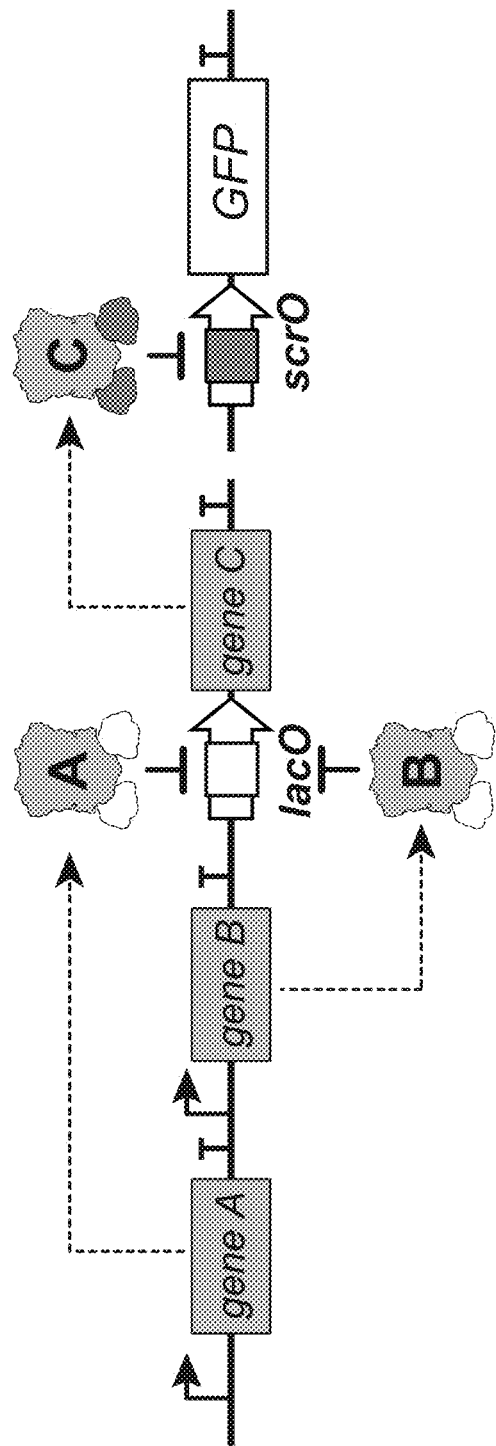
FIG. 25 demonstrates effects of long-term growth on the Passcode kill switches without toxin modules. Cells containing each version of the Passcode circuit were used to control gfp expression. These cells were passaged for 4 days under survival conditions unique to each Passcode circuit and periodically tested for circuit function by passage in media with no inducers. GFP expression was assessed with flow cytometry after 8 hours. Representative flow cytometry plots showed a monomodal distribution of cells in both the no inducer and survival conditions for 4 days. Data points represent the mean±S.D. of three biological replicates.
Figure 25:
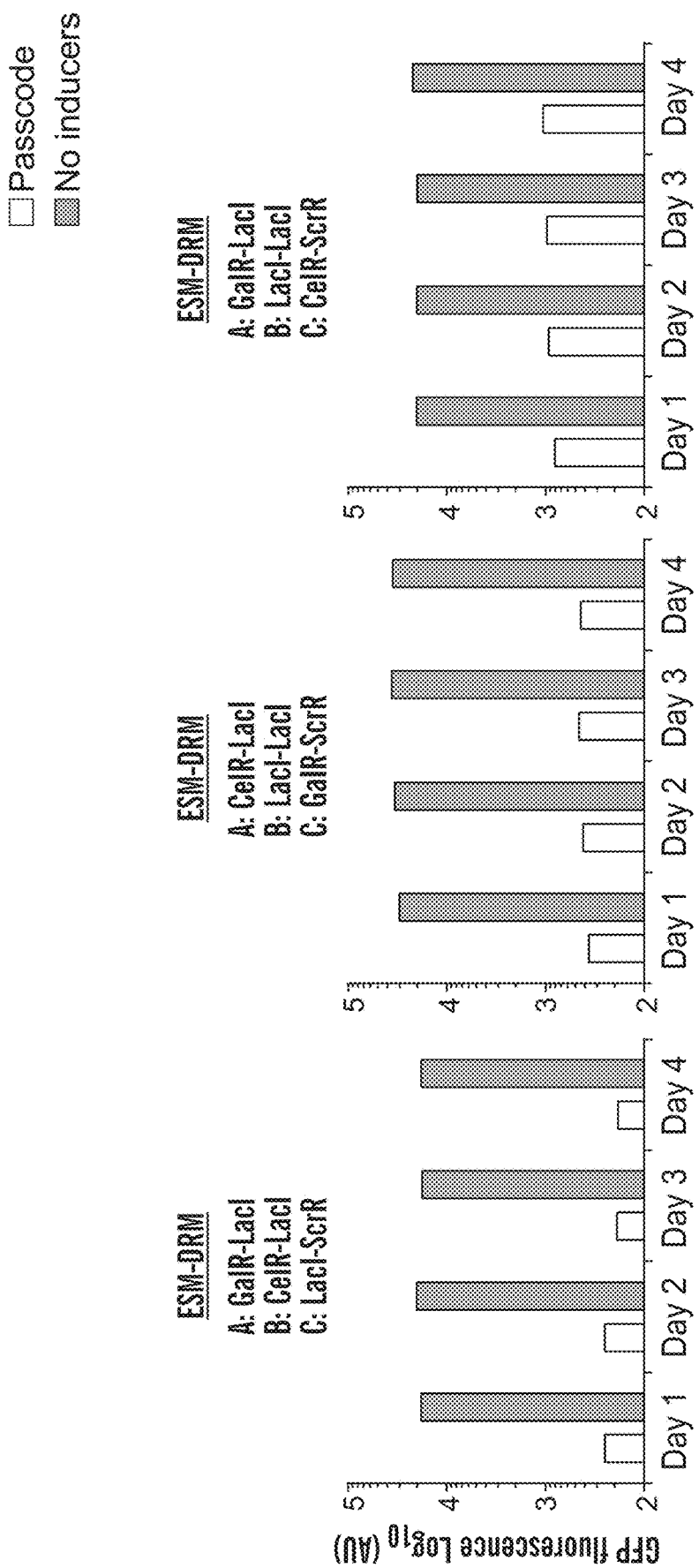
Figure 25:
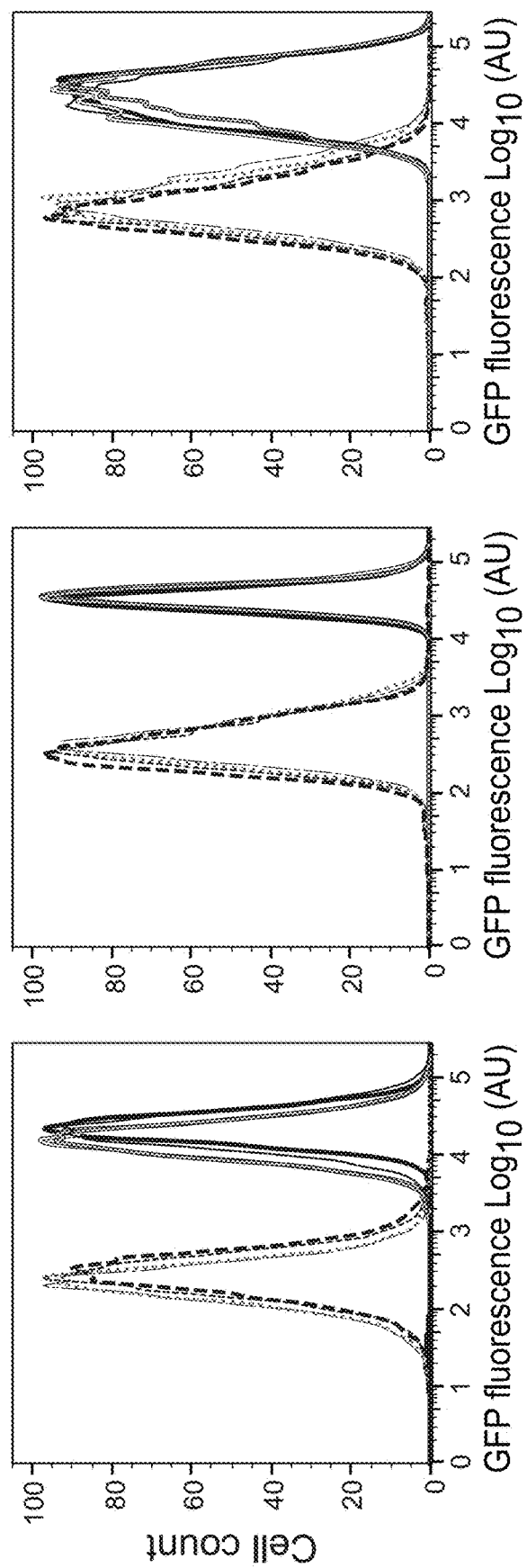

To measure the long-term stability and robustness of the Passcode and Deadman kill switches, we passaged cells containing the circuits for four days under survival conditions and periodically tested subsets of cells for circuit function under non-permissive conditions. Both the Deadman and Passcode circuits showed reduced killing efficiency over time, and sequence analysis of cells that escaped biocontainment predominantly showed inactivating mutations in the toxin genes (FIGS. 5A-5C and FIG. 23). The noted exception was independent TetR mutations in the two-toxin Deadman circuit where TetR inactivation repressed toxin expression even in the absence of the ATc survival signal. It is important to note, however, that these 'escapees' are still sensitive to IPTG-mediated fail-safe circuit activation as described above (FIG. 2). Genome-encoded insertion-sequence (IS) elements[37], particularly IS1 and IS5, caused a large percentage of inactivating mutations in the one-toxin and two-toxin Passcode circuits. Deletion of these IS elements and other genome repair mechanisms in E. coli reduced the Passcode 'escapee' rate by 3-5 logs after four days, demonstrating that increased stability of the host genome will augment the functionality of these biocontainment systems (FIG. 5B and FIG. 23). As the toxin genes were the main target for circuit inactivation, inclusion of additional redundant killing systems into each circuit should further reduce the escapee rate.

Described herein are two safe-guard systems, demonstrated in *Escherichia coli*, but generalizable across host cells in part due to the modularity of they systems' constituent parts. The systems include a "Deadman" kill switch that requires a specific input signal to block cell death and a "Passcode" circuit that uses hybrid transcription factors to detect multiple environmental inputs. These circuits efficiently kill *E. coli* and can be reprogrammed to change the input signal, regulatory architecture and killing mechanism.

The systems, compositions and methods described provide a biocontainment system for engineered bacteria. Examples include engineered probiotic bacteria in the human intestine, engineered bacteria or eukaryotes used in production facilities for fuels, chemicals and materials, and engineered bacteria or eukaryotes used in environmental applications, among others. The circuits are designed to kill any cells that are released from the intended environment.

The described systems also provide a tool for intellectual property protection. Unauthorized growth of a protected strain without the appropriate "passcode" molecules will induce cell death, and with the proper choice of toxins, such as endonucleases like EcoRI described here, the Passcode circuit can be used to not only kill the host cell but degrade its genome and accompanying plasmids to deter attempts at reverse-engineering. The use of hybrid TFs that respond to proprietary small molecule inputs will further secure the strain against theft even if its genome is sequenced.

The described systems also provide a tool to control the proliferation of pathogen used in research facilities. Unauthorized growth of the strain without a specific molecule or appropriate "passcode" molecules will activate a killing mechanism.

Existing biocontainment systems have used metabolic auxotrophy and the induction of toxin proteins to control cell survival, and recent strategies include the introduction of synthetic auxotrophy, enzyme redesign, orthogonal control of essential gene functions, and engineered addiction modules and riboregulated auxotrophy. However, many of these systems are intrinsically difficult to reprogram for different environmental conditions, potentially limiting their application.

Described herein is a circuit-based approach to develop versatile biocontainment systems that incorporate modularity into both the circuit designs and the environmental sensors that control them. Additionally, the high degree of modularity in both the Deadman and Passcode circuits dramatically expands the number and range of environmental signals that the circuits can detect. The ARM and DRM boundaries defined in the studies described herein can be used incorporate the sensing modules from many of the ~29,000 LacI family members into the hybrid TFs to detect other environmental signals, thereby increasing the specificity and complexity of the programmed "passcode". These hybrid TFs may also be used to "functionalize" existing synthetic circuits to respond to different environmental signals without having to modify the transcription regulatory architecture.

Biocontainment systems that couple environmental sensing with circuit-based control of cell viability can prevent escape of engineered microbes into the environment.

Described herein is the use of a monostable toggle design to control an output module. This design allows passive activation of the genetic circuit in the absence of the input molecule, and upon circuit activation, it provides a positive feedback loop that increases the speed of expression of the output module.

In the case of the deadman switch, this output module uses toxin genes to control cell survival, but the output module could be used to control any cell process.

Also described is the development of hybrid transcription factors that use the boundary region homologous to the *Escherischia coli* LacI protein region from aa36 to aa46 to create hybrid TFs containing the N-terminal DNA-binding domain and the C terminal sensor domain that are defined by that boundary. The resulting hybrid TFs recognize the small molecule defined by the C-terminal sensor domain and respond by binding or releasing the DNA region defined by the hybrid TF's N-terminal DNA binding domain.

Also described is the use of hybrid transcription factors to create biosensors in which the C-terminal sensor domains from diverse LacIfamily members are fused to the N-terminal DNA-binding domain from well-characterized transcription factors such as *E. coli* LacI to allow transcriptional activation from a well-characterized promoter upon detection of the small molecule by the C-terminal sensor domain.

Also described is the use of hybrid transcription factors to create a 'Passcode' circuit that requires the presence and/or absence of specific small molecules to activate the output module. By placing the genes that encode for cellular toxins in the output module, this circuit may be used to create a kill switch mechanism in which the circuit kills the cell if the cell leaves the specific environment defined by the sensor domains. The modularity of the hybrid TFs, the circuit architecture, and the output module allows the circuit to be reconfigured to sense other environmental signals, to react to the environmental signals in other ways, and to control other functions in the cell in addition to induced cell death.

The deadman switch can use alternative transcription factors to create the positive feedback loop or can use alternative methods including transcriptional, post-transcriptional, translational, or post-translational systems.

The output module can be reconfigured to use different cellular toxins to kill the cell or may be used to cause an alternative outputs such as degrading specific genetic components with or without killing the cell. The output module can be used to regulate other genetic circuits of endogenous genes with or without killing the cell. The output module can be an RNA-based circuit.

The deadman and passcode circuits can be used in other organisms, including other bacteria or eukaryotes, including mammalian cells.

For the deadman switch, replacement of TetR or LacI and their regulated promoters with repressors that sense other environmental signals would allow this circuit to sense a wide range of environmental cues.

The ARM and DRM boundary may be in any amino acid within the region defined by homology to E. coli LacI amino acids 36-46.

The ARM and DRM boundaries defined in this study can be used incorporate the sensing modules from many of the ~29,000 LacI family members into the hybrid TFs to detect other environmental signals.

The hybrid TFs can be used in alternative circuit architectures to control the circuit output. Additional hybrid TFs could be used to respond to different environmental signals to control the same promoter or hybrid TFs could be used to respond to the same signal to activate or repress different promoters.

More than two hybrid TFs can be used to control the same promoter.

Two or more hybrid TFs that sense the same molecule can be used in a circuit to control multiple promoters.

This invention is further illustrated by the following examples which should not be construed as limiting. It is understood that the foregoing description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

Example 1

As demonstrated herein, biocontainment systems that couple environmental sensing with circuit-based control of cell viability can be used to prevent escape of genetically modified microbes into the environment. Two exemplary, novel engineered safe-guard systems are described herein: the Deadman and Passcode kill switches. The Deadman kill switch uses unbalanced reciprocal transcriptional repression to couple a specific input signal with cell survival. The Passcode kill switch uses a similar two-layered transcription design and incorporates hybrid LacI/GalR family transcription factors to provide diverse and complex environmental inputs to control circuit function. These exemplary synthetic gene circuits efficiently kill Escherichia coli and can be readily reprogrammed to change their environmental inputs, regulatory architecture and killing mechanism.

With the advent of synthetic biology, genetically modified microorganisms have been increasingly used for biomedical, industrial and environmental applications[1-6]. Deployment of these engineered microbes in large scales and open environments calls for the development of safe and secure means to restrain their proliferation. Pioneering biocontainment systems used metabolic auxotrophy in which target cells could only grow in the presence of an exogenously supplied metabolite[7,8], and the recent creation of an E. coli strain with an altered genetic code enabled production of synthetic auxotrophy strains in which an exogenous supply of non-natural amino acids is required for cell survival[9,10]. Traditional metabolic auxotrophy strains are hampered by the potential for inadvertent complementation by crossfeeding or by the presence of the metabolite in heterogenous environments, and synthetic auxotrophy systems rely on extensive genome-wide engineering that can be impractical for many industrial production and biotherapeutic microbes. Furthermore, they are intrinsically difficult to reprogram for different environmental conditions, limiting their application.

As described herein, an alternative approach to biocontainment is to use gene circuits to maintain essential gene expression or block toxin gene expression under the assigned biocontainment conditions[7,11-14]. Upon loss of the biocontainment signal, the circuit blocks essential gene expression or induces toxin gene expression to kill the cell. These circuits offer the promise of complex environmental signal integration but are typically hindered by a relative lack of programmable environment sensors to enable their use under non-laboratory conditions[15].

Provided herein are programmable biocontainment circuits in E. coli—in some embodiments, a switch termed herein as a "Deadman kill switch" that uses, in part, a transcription-based monostable toggle design to provide rapid and robust target cell killing is used, and, in some embodiments, a circuit termed herein a "Passcode circuit" that uses hybrid LacI/GalR family transcription factors (TFs) to construct complex environmental requirements for cell survival is provided. As described herein, a tripartite strategy of (i) TF protein engineering to detect diverse input signals, (ii) robust circuit design to provide signal processing, and (iii) redundant toxin-induced and protease-mediated cell killing mechanisms was used. The resulting biocontainment systems described herein are modular, flexible and extensible, and are useful across many industrial and biotherapeutic applications.

Deadman Circuit Development

Figure 6:
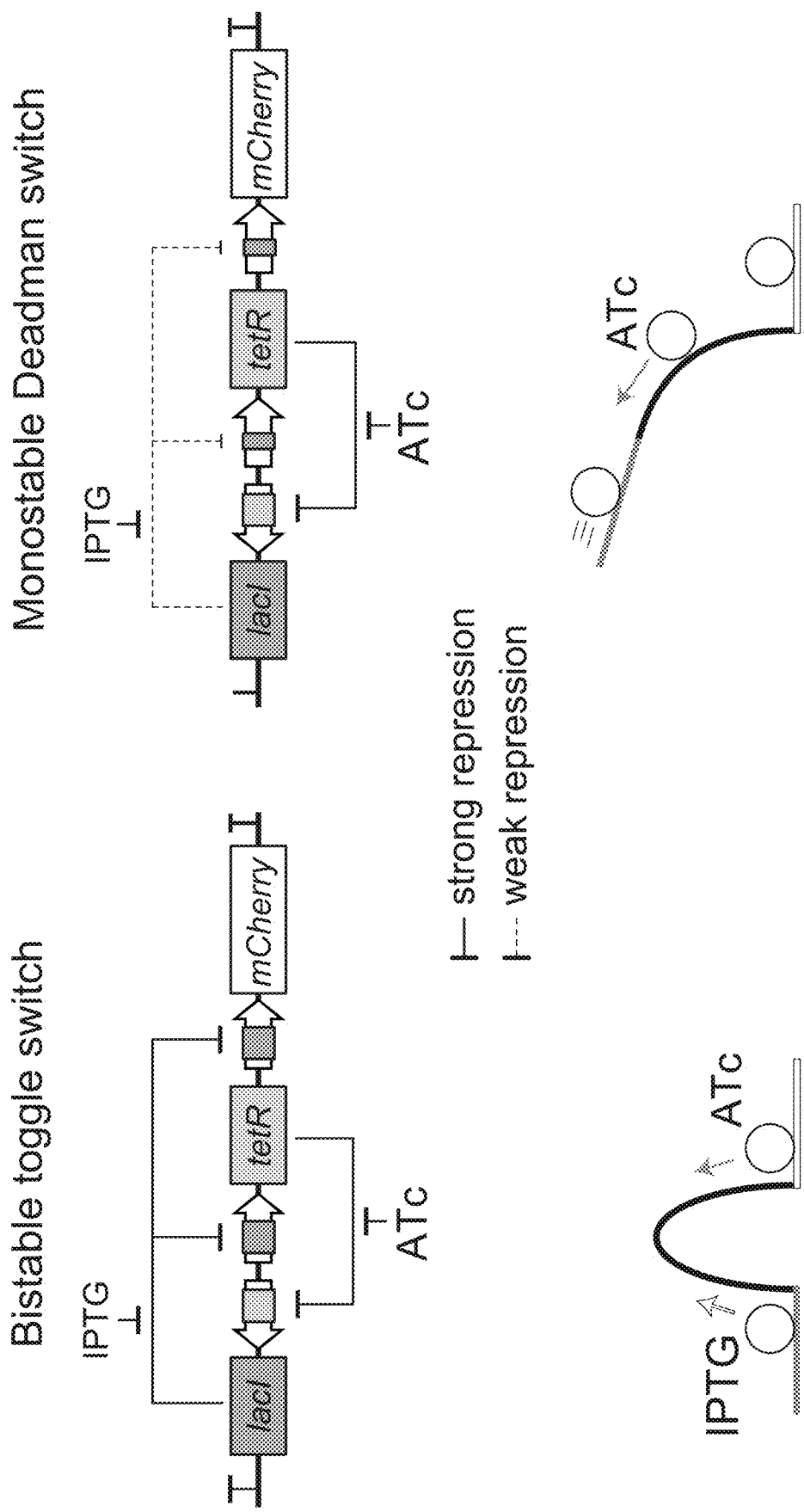
FIG. 6 depicts conversion of a bistable toggle into the monostable Deadman switch. The toggle switch requires strong reciprocal repression by LacI and TetR to create a bistable circuit. The bistable toggle switch was converted into a monostable switch in a single-copy plasmid by weakening LacI expression relative to TetR expression. The resulting Deadman switch requires ATc to maintain the circuit in the LacI+ state and returns to the TetR+ state upon ATc removal. mCherry serves as a fluorescent reporter for the TetR+ state.

We developed the Deadman kill switch to serve as a passively activated biocontainment system for engineered microbes. Similar to biocontainment systems in E. coli[12] and Pseudomonas putida[16], the Deadman circuit uses a small molecule binding transcription factor to produce a 'survival' state in which repression of toxin production is linked to the presence of a specific environmental signal. Upon loss of the environmental signal, the circuit switches to the 'death' state in which de-repressed toxin production kills the cell. To increase the robustness of these biocontainment states, the Deadman circuit uses a genetic 'toggle switch' architecture in which reciprocal repression by the LacI and TetR transcription factors form transcription states that are maintained by the circuit's linked feedback loops[17,18] (FIG. 6). To create a circuit in which the 'death' state is dominant in the absence of the survival signal, we altered the ribosome binding site (RBS) strengths of LacI and TetR to favor TetR expression in a single-copy plasmid (FIGS. 7A-7B and Supplementary Methods). In the resulting monostable circuit, the presence of the TetR inhibitor anhydrotetracycline (ATc) is required to maintain the circuit in the subordinate LacI+ 'survival' state (FIGS. 8A-8C). Incorporation of toxin genes into the TetR+ state creates a kill switch where the presence of ATc is required to block toxin expression and cell death.

We included additional palindromic LacI operator sites in the toxin gene promoter to minimize leaky toxin expression[19] and introduced a transcriptional terminator upstream of the promoter to insulate the gene from spurious transcription (FIGS. 9A-9C). To accelerate the circuit's switching dynamics, we fused a degradation tag to the C-terminus of LacI that is specifically recognized by mf-Lon[20], a heterologous protease under control of a LacI-dependent promoter (FIGS. 10A-10C). Upon removal of ATc, TetR repression of lacI allows expression of mf-Lon, which targets LacI for degradation to create a positive feedback loop that accelerates the switch to the TetR+ state (FIG. 10B). Importantly, single-cell analysis of these circuits by flow cytometry showed a monomodal distribution of cells in the LacI+ and TetR+ state, demonstrating stable circuit expression across the cell population (see 0 and 6 hour data in FIG. 10C).

Deadman Kill Switch Characterization

To identify an efficient mechanism to kill the host cells upon circuit activation, we tested several toxin genes that directly damage the host cell's DNA or RNA. We chose to test the endonuclease ecoRI[21], the DNA gyrase inhibitor ccdB[22] and the ribonuclease-type toxin mazF[23] because they are well-characterized, are native to *E. coli*, and provide a range of killing mechanisms. The toxin genes were independently incorporated into the Deadman circuit, and a range of RBS strengths were tested for each toxin to optimize cell death upon circuit activation[24] (FIGS. 11A-11B). Upon removal of ATc, the toxins produced 3-5 logs of killing within 6 hours as measured by colony forming units (CFUs) (FIG. 1A). To increase the robustness of the circuit and provide an independent method of circuit-dependent cell death, we used mf-Lon protease to not only degrade LacI but also target essential proteins for degradation (FIG. 1B). We attached the mf-Lon degradation tag pdt#1 to the 3' end of five essential genes whose protein products are particularly sensitive to mf-Lon degradation[20], and we then measured cell viability following removal of ATc (FIG. 1B). Among the tested essential gene targets, the peptidoglycan biosynthesis gene murC provided the strongest and fastest cell death phenotype (survival ratio $<1\times10^{-4}$ within 6 hours).

To determine if the toxin- and mf-Lon-mediated killing mechanisms produce synergistic effects, we created Deadman circuits containing each of the toxins in combination with the mf-Lon-MurC targeting module (FIG. 1C). In each instance, the combinatorial approach provided more effective biocontainment, and in particular, coordinated EcoRI expression and mf-Lon-mediated MurC degradation resulted in cell killing below the limit of detection (survival ratio $<1\times10^{-7}$) 6 hours after removal of ATc (FIG. 1C). Furthermore, the Deadman circuit's design provides an additional fail-safe mechanism which bypasses the circuit's sensor system to directly activate toxin expression to cause cell death. Direct derepression of the subordinate TF, in this case derepression of LacI with isopropyl β-D-1-thiogalactopyranoside (IPTG), activates toxin production and cell death irrespective of the presence of the programmed survival signal (FIG. 2).

Hybrid Transcription Factor Design

To extend the versatility and modularity of this system, we built a second circuit, called the Passcode circuit, which uses hybrid LacI/GalR family TFs to expand the range and complexity of environmental signals used to define biocontainment conditions. This survival "passcode" can be easily reprogrammed to restrict cell growth to a new environment or to limit knowledge of the growth conditions to authorized personnel. To build hybrid LacI family TFs, we first identified the boundaries of the environmental sensing modules (ESMs) and DNA recognition modules (DRMs) found in LacI family members (FIG. 3A and FIGS. 12-15). Ee generated hybrid TFs that use the small molecule input defined by the hybrid's ESM to regulate the promoter defined by the hybrid's DRM[25,26] (FIG. 3A and FIGS. 16A-16C).

To construct the hybrid TFs, we used the cellobiose-responsive TF CelR from *Thermobifida fusca* and the galactose-responsive TF GalR and IPTG-responsive LacI from *E. coli*. We fused the ESMs from CelR and GalR to the DRM of LacI to generate the hybrid TFs CelR-LacI and GalR-LacI. To test their functionality, these hybrid TFs or native LacI were used to control GFP expression from a promoter containing lacO operator sites recognized by the LacI DRM. The hybrid TFs allowed strong GFP expression upon exposure to the small molecule input defined by their ESM and showed almost no response to the other inputs (FIG. 3A and FIG. 16B). We fused the LacI, GalR and CelR ESMs to the DRM of ScrR from *Klebsiella pneumoniae* and used the resulting hybrid TFs to regulate a promoter containing scrO operator sites. As predicted from their design, these hybrid TFs only respond to the input defined by their ESM (FIG. 3B and FIG. 16C), although it is interesting to note that the GalR ESM shows distinct inhibition by high levels of IPTG as seen by Shis et al.[27] (FIG. 17). Importantly, the DRMs used in these hybrid TFs provided similar specificity, as they regulated promoters containing their cognate operator sites but not other LacI family operator sites (FIG. 18). Similar to work by Shis et al.[27], we found that co-expression of hybrid TFs containing the same DRM could be used to regulate a single promoter, creating an AND logic gate function (FIG. 19).

Development of the Passcode Kill Switches

We used these hybrid TFs to create a series of Passcode circuits that contain a single transcriptional architecture but respond to distinct combinations of environmental inputs to control gene expression and cell survival. As shown in FIGS. 20A-20C, the Passcode circuits contain the output module (in this case, gfp) under control of a TF (hybrid C) whose expression is controlled by an AND gate formed by two TFs (hybrid A and hybrid B). This serial arrangement, made possible by the orthogonality of the hybrid DRMs and ESMs, creates the condition that both of the inducers recognized by hybrid A and hybrid B (inputs a and b, respectively) must be present to allow expression of hybrid C to repress gfp expression. Loss of input a or input b or the presence of input c allows gfp expression, causing cell death if gfp is replaced by a toxin gene.

To test the functionality and modularity of this circuit architecture, we created three exemplary embodiments of the Passcode circuit that respond to different combinations of input signals to control output expression (FIG. 4A). For example, in one Passcode circuit (FIG. 4B, left column), we used GalR-LacI (A) and CclR-LacI (B) to control expression of LacI-ScrR (C), which in turn represses toxin expression. In this circuit, loss of galactose (input a) or cellobiose (input b) allows GalR-LacI or CelR-LacI to bind the lacO operator, blocking LacI-ScrR expression, thereby enabling toxin expression and causing cell death. Any exposure to IPTG (input c) releases LacI-ScrR repression of toxin expression, thereby killing the cell as well. Importantly, the passcode combinations for cell survival and cell death can be reprogrammed by rearranging the ESMs of the three TFs to rewire the connections between the environmental sensing and transcriptional regulation, in different embodiments.

These Passcode circuits were first evaluated with GFP as the output module in all eight combinations of the three environmental inputs. All three circuits allowed high level GFP expression in all conditions except that designated by the desired three input combination (FIG. 20B), and single-cell fluorescence showed a monomodal population distribution under all conditions (FIG. 20C). GFP was then replaced with the ecoRI and mf-Lon-MurC toxin modules described for the Deadman switch above (FIG. 4A), and toxin expression levels were optimized by testing a range of calculated RBS strengths[24] (FIG. 21). Hybrid C, which directly controls toxin expression in the circuit, was also engineered in the same manner to optimize circuit performance (see Supplementary Methods). Each kill switch circuit was tested in E. coli using eight combinations of input signals, and cell survival was measured by CFU count at multiple time points (FIG. 22). As seen in FIG. 4B, only circuits that received the proper survival code allowed the host cells to survive (each survival condition is highlighted in green). Furthermore, inclusion of both the ecoRI and mf-Lon toxin modules in the Passcode circuit caused the cell survival ratio to drop below $1\times10^{-6}$ for all non-passcode conditions.

Circuit Stability

To measure the long-term stability and robustness of the Passcode and Deadman kill switches, we passaged cells containing the circuits for four days under survival conditions and periodically tested subsets of cells for circuit function under non-permissive conditions. Both the Deadman and Passcode circuits showed reduced killing efficiency over time, and sequence analysis of cells that escaped biocontainment predominantly showed inactivating mutations in the toxin genes (FIGS. 5A-5C and FIG. 23). The noted exception was independent TetR mutations in the two-toxin Deadman circuit where TetR inactivation repressed toxin expression even in the absence of the ATc survival signal. It is important to note, however, that these 'escapees' are still sensitive to IPTG-mediated fail-safe circuit activation as described above (FIG. 2). Genome-encoded insertion-sequence (IS) elements[37], particularly IS1 and IS5, caused a large percentage of inactivating mutations in the one-toxin and two-toxin Passcode circuits. Deletion of these IS elements and other genome repair mechanisms in E. coli reduced the Passcode 'escapee' rate by 3-5 logs after four days, demonstrating that increased stability of the host genome will augment the functionality of these biocontainment systems (FIG. 5B and FIG. 23). As the toxin genes were the main target for circuit inactivation, inclusion of additional redundant killing systems into each circuit should further reduce the escapee rate.

The Deadman and Passcode switches provide robust information processing circuits to couple environmental signals with conditional survival of the microbial host. The Deadman kill switch described above is based on a monostable circuit that passively activates toxin gene expression in the absence of the small molecule input ATc. Since ATc is not normally found in nature, engineered cells that escape biocontainment will trigger cell death to prevent the spread of the organism or its genetic content into the surrounding ecosystem. Unlike auxotrophy-based biocontainment where the environmental signal is an intrinsic feature of the system[9,10], the environmental sensing and cell killing systems are decoupled in the Deadman switch. This circuit relies on two main elements for functionality: (1) the orthogonality of the TFs to create a toggle switch, and (2) their relative activity under induced expression. As such, the Deadman circuit is highly modular, and the environmental signal detected by the circuit may be altered by replacing TetR with a wide range of transcription factors, including more than 80,000 annotated TetR family members[38] as well as orthogonal LacI/GalR family members including hybrid TFs as described for the Passcode switch. In addition, the Deadman circuit has an additional fail-safe mechanism which activates toxin production and cell death in the presence of IPTG, enabling exogenous control over the microbe's survival even as the cell uses the circuit to monitor its environment.

Similar to the Deadman switch, the Passcode circuits are based on a two-layered transcriptional repression design. To build hybrid TFs, we identified the conserved boundaries of the ESMs and DRMs within the LacI/GalR family members LacI, GalR, CelR and ScrR. The resulting environmental sensing and DNA binding modules provide independent control of the sensory input and regulatory output of each hybrid TF. Pioneering work by Meinhardt et al.[27,28] used the boundary between the conserved regulatory domain and HH motif to create hybrid TFs, but some of these hybrids required additional protein engineering and mutagenesis to become functional. Here we identify a discrete boundary between the conserved HH and HTH motifs to create independent environmental sensory and DNA binding domains that can be efficiently combined without further protein engineering. The modularity provided by these hybrid TFs dramatically expands the number and range of environmental signals that can be used to control biocontainment systems such as the Deadman and Passcode circuits described here, as the ESM and DRM boundaries defined in this study may be used to incorporate sensing modules from many of the ~29,000 LacI/GalR family members[39] that detect diverse environmental signals.

These hybrid TFs may also be used to functionalize other synthetic circuits, including the Deadman switch, to respond to different environmental signals. Moreover, the regular use of LacI and TetR in other bacteria[40,41] suggests that these circuits may be readily transferred to other microbes, including industrial production strains. Replacement of the antibiotic resistance cassettes in these plasmids with well characterized selection systems that use toxin-antitoxin modules or auxotrophy complementation should also enable their use in biotherapeutic applications[4,42].

In summary, we have established two exemplary circuit-based microbial kill switches that constrict host cell survival to an environment defined by specific input signals. Unlike existing biocontainment systems with fixed survival conditions that are difficult to modify, the Deadman and Passcode kill switches are inherently customizable, both in the environmental conditions that control circuit activation and in the output modules that control cell fate. In addition to its use as a biocontainment system, the Passcode circuit may find particular utility as a tool for intellectual property protection, where unauthorized growth of strains without the appropriate "passcode" molecules would induce cell death. With the proper choice of toxins, such as the endonuclease EcoRI described here, the Passcode circuit could be used to not only kill the host cell but also degrade its genome and accompanying plasmids to deter attempts at reverse-engineering the strain of interest. Use of hybrid TFs that respond to proprietary small molecule inputs may further secure the strain against theft, even if its genome is sequenced.

Example 1 Methods

Strains. E. coli MG1655ΔlacI was the parental strain for all circuit characterization and was created through P1 phage transduction of lacI::kanR from the Keio collection[43] into E. coli MG1655 (ATCC 47076). Flp recombinase, expressed on pCP20, was used to remove the kanR cassette[44]. To construct E. coli strains containing mf-Lon recognition tags on the essential genes dxs, cysS,fldA, plsB or murC, the pdt#1 mf-Lon recognition tag from each corresponding gene in the EPD library[20] was transferred to MG1655ΔlacI by P1 phage transduction and the kanR cassette was removed as above. P1 phage transduction was used to convert E. coli MDS42pdu[11] (Scarab Genomics) for use in the Passcode switch analysis. Specifically, lack: kanR and recA::kanR deletions from the Keio collection[16] and murC-pdt#1 from the EPD library[17] were independently transferred to MDS42pdu by P1 phage transduction, and the accompanying kanamycin cassettes were removed by FlpE-mediated excision using pECA102.

Cell growth and media. Luria-Bertani (LB) media was used for all experiments, and the following antibiotics and inducers were included when appropriate: ampicillin (50 µg/ml), chloramphenicol (10 µg/ml), kanamycin (50 µg/ml), ATc (100 ng/ml), IPTG (1 mM), galactose (20 mM) and cellobiose (5 mM). For the Deadman switch, single colonies grown on LB agar plates containing ATc were inoculated into liquid cultures containing ATc for growth overnight at 37° C. with shaking. Similarly, cells harboring each of the three Passcode switches were picked from plates with the survival combination of inputs and inoculated into their respective survival liquid media. Overnight cultures were inoculated 1:20,000 into 96-well plates and grown at 37° C. and 900 rpm for further tests.

Plasmid construction. All plasmids were constructed using conventional molecular cloning protocols[45] and Gibson Assembly[46]. E. coli NEB Turbo (New England BioLabs Inc.) was used for cloning purposes, and all primers were purchased from IDT. To create the Deadman switch pDM1 (Genbank accession number TBD), genetic elements from the toggle pECJ3[20] were cloned into the conditionally amplified single-copy plasmid pBAC/oriV[47], and the lacI and tetR RBS strengths were modified as described in FIGS. 2A-2B and the Supplementary Methods. To provide increased control over the promoter controlling mCherry expression, the T1 terminator from rnpB (Registry of Standard Biological Parts BBa_J61048) was inserted upstream (FIG. 8A), and three palindromic lac operator sites[19] were inserted around the −35 and −10 region of the promoter (pDM2, GenBank accession number TBD). Finally, the M. florum protease gene mf-lon was cloned under control of an additional LacI-regulated promoter (FIG. 8A). The resulting plasmid, pDM3 (GenBank accession number TBD), served as the base Deadman circuit, and mCherry was replaced with ecoRI, ccdB and mazF to make the toxin variants (see Table 1).

Hybrid TF genes (lacI-galR LG36-LG46, galR-lacI, celR-lacI, lacI-scrR, galR-scrR, and celR-scrR) were constructed by overlap extension PCR to fuse the environmental sensing modules (ESMs) and the DNA recognition modules (DRMs) of the designated genes. The hybrid TFs were cloned into pTR, a derivative of pKE2-MCS containing the pLtetO-1 promoter and T0 terminator from pZA11[34], using restriction sites BamHI and BsrGI. Transcription from the pLtetO-1 promoter driving TF expression is constitutive because the E. coli strains used in this study did not contain tetR. Reporter plasmids (pREPORT) were constructed from the plasmid pZA12[34], with mcherry or gfp inserted downstream of the pLlacO promoter using KpnI and HindIII. To test hybrid TFs that contain the ScrR DRM, pLlacO-1 was replaced with pLscrO-1 or pLscrO-2 using the Gibson Assembly method[46]. Hybrid TF and plasmid sequences will be deposited in GenBank.

The Passcode circuit was developed using a two-plasmid system. Plasmid pTR (GenBank accession number TBD), derived from pKE2_MCS[17], was constructed to contain the hybrid TF circuit, and pREPORT (GenBank accession number TBD), derived from pZA12[34], was constructed to contain the toxin output module under control of the pLscrO promoter. For pTR, three promoter-hybrid TF-terminator fragments were used to construct each hybrid TF circuit version, as listed in Table 1. For version 1 of pTR, in which LacI-ScrR is used as hybrid C, the promoter pLscrO-2 was utilized to control the expression of toxin gene(s) in pREPORT. For the other two versions of pTR, the promoter-pLscrO-1 was used for toxin control in pREPORT. For Passcode circuits that contain two toxin gene systems, the DNA fragments pLscrO-mf-Lon-terminator and pLscrO-ecoRI-terminator were incorporated into pREPORT using Gibson Assembly (Table 1). For Passcode circuit characterization, pTR was first transformed into the desired E. coli strain and grown in media containing the "passcode" combination of the three inputs (IPTG, galactose and cellobiose). Plasmid pREPORT, which contains the toxin gene(s), was then transformed into the cells to complete the Passcode circuit.

Flow cytometry assay. Cells containing Passcode circuits were grown as described for each experiment, and at the appropriate time were fixed in 2% paraformaldehyde in PBS and then diluted 1:10 in PBS for analysis. GFP fluorescence measurements were performed using a BD FACSARIAII (BD BIOSCIENCES) or a BD LSRFORTESSA™ flow cytometer (BD BIOSCIENCES). Flow cytometry data were gated by forward and side scatter to eliminate multi-cell aggregates, and the geometric mean of GFP fluorescence distributions were calculated using FLOWJO software (TREESTAR). At least 10,000 events were collected for each measurement.

Survival assays. Colony forming unit (CFU) cell viability assays were used to measure functionality of the Deadman and Passcode circuits. Overnight cultures were grown under the survival conditions (Deadman: with ATc, Passcode: with survival "passcode" inputs) and were transferred into fresh LB medium with or without the survival signal(s). For the Passcode circuit, all eight combinations of the three inputs were tested (+/−IPTG, +/−galactose and +/−cellobiose). Samples were collected every two hours, serially diluted in PBS over a 7-log range, and spotted (5 µL) onto a square plate containing LB agar with the appropriate survival signal(s). CFU and survival ratios were calculated as previously reported[11]: CFU/mL=(number of colonies)×(dilution factor)/0.005 mL, survival ratio $(\log_{10})$=log {(CFU/mL without the survival signal)/(CFU/mL with the survival signal)}.

References

1 Moe-Behrens, G. H., Davis, R. & Haynes, K. A. Preparing synthetic biology for the world. *Frontiers in microbiology* 4, 5, doi:10.3389/fmicb.2013.00005 (2013).
2 Bacchus, W., Aubel, D. & Fussenegger, M. Biomedically relevant circuit-design strategies in mammalian synthetic biology. *Molecular systems biology* 9, 691, doi:10.1038/msb.2013.48 (2013).

3 Olson, E. J. & Tabor, J. J. Post-translational tools expand the scope of synthetic biology. *Current opinion in chemical biology* 16, 300-306, doi:10.1016/j.cbpa.2012.06.003 (2012).

4 Wright, O., Delmans, M., Stan, G. B. & Ellis, T. GeneGuard: A Modular Plasmid System Designed for Biosafety. *ACS synthetic biology,* doi:10.1021/sb500234s (2014).

5 Chappell, J. et al. The centrality of RNA for engineering gene expression. *Biotechnology journal* 8, 1379-1395, doi:10.1002/biot.201300018 (2013).

6 Cameron, D. E., Bashor, C. J. & Collins, J. J. A brief history of synthetic biology. Nature reviews. *Microbiology* 12, 381-390, doi:10.1038/nrmicro3239 (2014).

7 Wright, O., Stan, G. B. & Ellis, T. Building-in biosafety for synthetic biology. *Microbiology* 159, 1221-1235, doi:10.1099/mic.0.066308-0 (2013).

8 Steidler, L. et al. Biological containment of genetically modified Lactococcus lactis for intestinal delivery of human interleukin 10. *Nature biotechnology* 21, 785-789, doi:10.1038/nbt840 (2003).

9 Rovner, A. J. et al. Recoded organisms engineered to depend on synthetic amino acids. *Nature* 518, 89-93, doi:10.1038/nature14095 (2015).

10 Mandell, D. J. et al. Biocontainment of genetically modified organisms by synthetic protein design. *Nature* 518, 55-60, doi:10.1038/nature14121 (2015).

11 Callum, J. M., Dwyer, D. J., Isaacs, F. J., Cantor, C. R. & Collins, J. J. Tracking, tuning, and terminating microbial physiology using synthetic riboregulators. *Proceedings of the National Academy of Sciences of the United States of America* 107, 15898-15903, doi:10.1073/pnas.1009747107 (2010).

12 Contreras, A., Molin, S. & Ramos, J. L. Conditional-suicide containment system for bacteria which mineralize aromatics. *Applied and environmental microbiology* 57, 1504-1508 (1991).

13 Cai, Y. et al. Intrinsic biocontainment: Multiplex genome safeguards combine transcriptional and recombinational control of essential yeast genes. *Proceedings of the National Academy of Sciences of the United States of America* 112, 1803-1808, doi:10.1073/pnas.1424704112 (2015).

14 Gallagher, R. R., Patel, J. R., Interiano, A. L., Rovner, A. J. & Isaacs, F. J. Multilayered genetic safeguards limit growth of microorganisms to defined environments. *Nucleic acids research* 43, 1945-1954, doi:10.1093/nar/gku1378 (2015).

15 Voigt, C. A. Genetic parts to program bacteria. *Current opinion in biotechnology* 17, 548-557, doi:10.1016/j.copbio.2006.09.001 (2006).

16 Jensen, L. B., Ramos, J. L., Kaneva, Z. & Molin, S. A substrate-dependent biological containment system for Pseudomonas putida based on the *Escherichia coli* gef gene. *Applied and environmental microbiology* 59, 3713-3717 (1993).

17 Litcofsky, K. D., Afeyan, R. B., Krom, R. J., Khalil, A. S. & Collins, J. J. Iterative plug-and-play methodology for constructing and modifying synthetic gene networks. *Nature methods* 9, 1077-1080, doi:10.1038/nmeth.2205 (2012).

18 Gardner, T. S., Cantor, C. R. & Collins, J. J. Construction of a genetic toggle switch in *Escherichia coli. Nature* 403, 339-342, doi:10.1038/35002131 (2000).

19 Sadler, J. R., Sasmor, H. & Betz, J. L. A perfectly symmetric lac operator binds the lac repressor very tightly. *Proceedings of the National Academy of Sciences of the United States of America* 80, 6785-6789 (1983).

20 Cameron, D. E. & Collins, J. J. Tunable protein degradation in bacteria. *Nature biotechnology* 32, 1276-1281, doi:10.1038/nbt.3053 (2014).

21 Cheng, S. C., Kim, R., King, K., Kim, S. H. & Modrich, P. Isolation of gram quantities of EcoRl restriction and modification enzymes from an overproducing strain. *The Journal of biological chemistry* 259, 11571-11575 (1984).

22 Smith, A. B. & Maxwell, A. A strand-passage conformation of DNA gyrase is required to allow the bacterial toxin, CcdB, to access its binding site. *Nucleic acids research* 34, 4667-4676, doi:10.1093/nar/gk1636 (2006).

23 Zhang, Y. et al. MazF cleaves cellular mRNAs specifically at ACA to block protein synthesis in *Escherichia coli. Molecular cell* 12, 913-923 (2003).

24 Salis, H. M. The ribosome binding site calculator. *Methods in enzymology* 498, 19-42, doi:10.1016/B978-0-12-385120-8.00002-4 (2011).

25 Swint-Kruse, L. & Matthews, K. S. Allostery in the LacI/GalR family: variations on a theme. *Current opinion in microbiology* 12, 129-137, doi:10.1016/j.mib.2009.01.009 (2009).

26 Finn, R. D. et al. Pfam: the protein families database. *Nucleic acids research* 42, D222-230, doi:10.1093/nar/gkt1223 (2014).

27 Mcinhardt, S. & Swint-Kruse, L. Experimental identification of specificity determinants in the domain linker of a LacI/GalR protein: bioinformatics-based predictions generate true positives and false negatives. *Proteins* 73, 941-957, doi:10.1002/prot.22121 (2008).

28 Meinhardt, S. et al. Novel insights from hybrid LacI/GalR proteins: family-wide functional attributes and biologically significant variation in transcription repression. *Nucleic acids research* 40, 11139-11154, doi:10.1093/nar/gks806 (2012).

29 Jarema, M. A., Lu, P. & Miller, J. H. Lac repressor: a genetic and nuclear magnetic resonance study of structure and function. *Biophysical journal* 32, 450-452 (1980).

30 Jarema, M. A., Lu, P. & Miller, J. H. Genetic assignment of resonances in the NMR spectrum of a protein: lac repressor. *Proceedings of the National Academy of Sciences of the United States of America* 78, 2707-2711 (1981).

21 Lewis, M. et al. Crystal structure of the lactose operon repressor and its complexes with DNA and inducer. *Science* 271, 1247-1254 (1996).

32 Bell, C. E. & Lewis, M. A closer view of the conformation of the Lac repressor bound to operator. *Nature structural biology* 7, 209-214, doi:10.1038/73317 (2000).

33 Friedman, A. M., Fischmann, T. O. & Steitz, T. A. Crystal structure of lac repressor core tetramer and its implications for DNA looping. *Science* 268, 1721-1727 (1995).

34 Lutz, R. & Bujard, H. Independent and tight regulation of transcriptional units in *Escherichia coli* via the LacR/O, the TetR/O and AraC/I1-I2 regulatory elements. *Nucleic acids research* 25, 1203-1210 (1997).

35 Spiridonov, N. A. & Wilson, D. B. Characterization and cloning of celR, a transcriptional regulator of cellulase genes from *Thermomonospora fusca. The Journal of biological chemistry* 274, 13127-13132 (1999).

36 Shis, D. L., Hussain, F., Meinhardt, S., Swint-Kruse, L. & Bennett, M. R. Modular, multi-input transcriptional logic gating with orthogonal LacI/GalR family chimeras. *ACS synthetic biology* 3, 645-651, doi:10.1021/sb500262f (2014).

37 Sousa, A., Bourgard, C., Wahl, L. M. & Gordo, I. Rates of transposition in *Escherichia coli*. *Biology letters* 9, 20130838, doi:10.1098/rsbl.2013.0838 (2013).

38 Cuthbertson, L. & Nodwell, J. R. The TetR family of regulators. *Microbiology and molecular biology reviews : MMBR* 77, 440-475, doi:10.1128/MMBR.00018-13 (2013).

39 Finn, R. D. et al. Pfam: the protein families database. *Nucleic acids research* 42, D222-230, doi:10.1093/nar/gkt1223 (2014).

40 Ramos, J. L. et al. The TetR family of transcriptional repressors. *Microbiology and molecular biology reviews : MMBR* 69, 326-356, doi:10.1128/MMBR.69.2.326-356.2005 (2005).

41 Cebolla, A., Vazquez, M. E. & Palomares, A. J. Expression vectors for the use of eukaryotic luciferases as bacterial markers with different colors of luminescence. *Applied and environmental microbiology* 61, 660-668 (1995).

42 Mignon, C., Sodoyer, R. & Werle, B. Antibiotic-free selection in biotherapeutics: now and forever. *Pathogens* 4, 157-181, doi:10.3390/pathogens4020157 (2015).

43 Baba, T. et al. Construction of *Escherichia coli* K-12 in-frame, single-gene knockout mutants: the Keio collection. *Molecular systems biology* 2, 2006 0008, doi:10.1038/msb4100050 (2006).

44 Datsenko, K. A. & Wanner, B. L. One-step inactivation of chromosomal genes in *Escherichia coli* K-12 using PCR products. *Proceedings of the National Academy of Sciences of the United States of America* 97, 6640-6645, doi:10.1073/pnas.120163297 (2000).

45 T, M., EF, F. & J, S. Molecular Cloning: A Laboratory Manual. *Cold Spring Harbor Laboratory Press*, 545 (1982).

46 Gibson, D. G. et al. Enzymatic assembly of DNA molecules up to several hundred kilobases. *Nature methods* 6, 343-345, doi:10.1038/nmeth.1318 (2009).

47 Wild, J., Hradecna, Z. & Szybalski, W. Conditionally amplifiable BACs: switching from single-copy to high-copy vectors and genomic clones. *Genome research* 12, 1434-1444, doi:10.1101/gr.130502 (2002).

Example 2

Methods

Analysis of protein sequences and crystal structures. ClustalW2[12] was used for protein sequence alignment of GalS, GalR, AscG, RbsR, PurR, GntR, LacI, and MalI from *E. coli*; CelR from *T. fusca*; ScrR from *V. alginolyticus* (ScrR-V); and ScrR from *K. pneumonia* (ScrR-K). Protein crystal structure analysis was performed with PyMol 1.5.x using Protein Data Bank (PDB) entries 1EFA, 1LBG, 1LBI, 1LBH, 1QPZ, and 1TLF[5-7,13,14].

Figure 15:
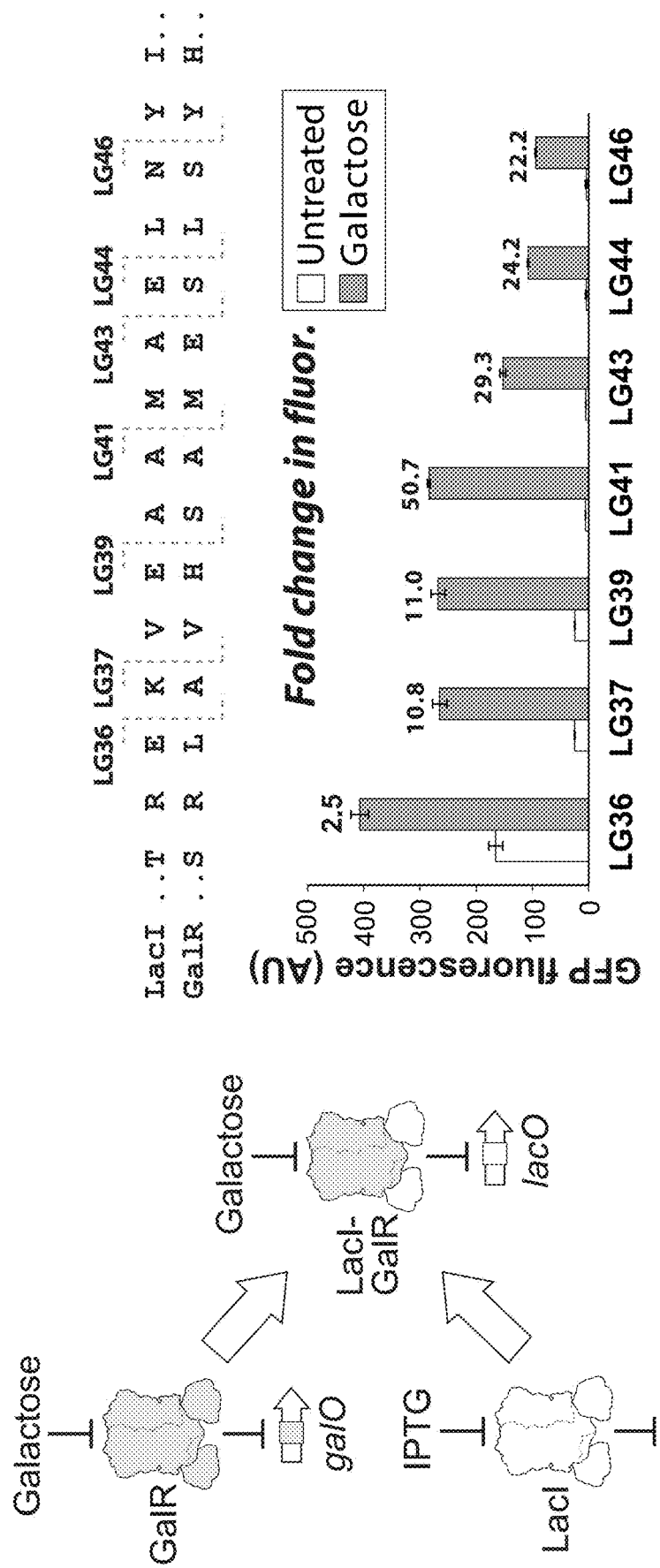
FIG. 15 demonstrates determination of the optimal ESM/DRM boundary for the GalR-LacI hybrid TF. Residues 34-48 of LacI (SEQ ID NO: 66) are aligned with the homologous GalR residues (SEQ ID NO: 67), and the dotted lines indicate the position between the GalR ESM and LacI DRM used to generate the hybrid TFs, which are designated LG36 to LG46 according to the hybrid site used. The TFs were expressed in cells containing a gfp reporter under control of the pLlacO-1 promoter10. Cells were grown in the presence or absence of 20 mM galactose for 1 hour, and GFP fluorescence was measured by flow cytometry. Fold-change in fluorescence is the ratio of fluorescence in galactose treated to untreated cells. Data points represent the mean±S.D. of three biological replicates.

Strain construction. *E. coli* MG1655ΔlacI and *E. coli* MG1655Pro[10,15] were used for Deadman and Passcode switch construction. *E. coli* MG1655ΔlacI was used to perform functional analysis of hybrid TFs as shown in FIGS. 15-17. In this strain, transcription from the pLtetO-1 promoter driving TF expression is constitutive because it does not contain tetR. *E. coli* MG1655Pro, which produces high levels of LacI and TetR[15], was used in hybrid TF analysis when LacI regulation of pLlacO-1 was a desired feature (FIGS. 18-19). In these assays, the TetR inhibitor anhydrotetracycline (ATc; 100 ng/mL) was included in the media to ensure TF expression from the pLtetO promoter. P1 phage transduction was used to convert *E. coli* MDS42pdu[11] (Scarab Genomics) for use in the Passcode switch analysis. Specifically, lacI::kanR and recA::kanR deletions from the Keio collection[16] and murC-pdt#1 from the EPD library[17] ENREF 19 were independently transferred to MDS42pdu by P1 phage transduction, and the accompanying kanamycin cassettes were removed by FlpE-mediated excision using pECA102.

Deadman monostable toggle construction. To construct the monostable toggle, an RBS calculator algorithm[18] was used to identify RBS variants that produce a range of LacI and TetR expressions (Table 1). Cells containing each toggle RBS variant were grown overnight in the presence of ATc, transferred to media without ATc, and then measured for mCherry expression by flow cytometry after 6 hours. Toggle variant 5, which showed the largest change in mCherry fluorescence upon loss of ATc, was chosen for use in the Deadman circuit (FIGS. 2A-2B). To quantify the relative LacI and TetR expression levels, mCherry was fused to the C-terminus of LacI or TetR to yield pBAC-LC and pBAC-ATc, respectively (GenBank accession numbers TBD). RBS variants for LacI and TetR were then cloned into pBAC-LC and pBAC-TC, respectively, and a SpectraMax M5 microplate reader (Molecular Devices) was used to measure mCherry fluorescence with excitation and emission wavelengths of 587 nm and 610 nm, respectively, with an emission filter cutoff at 610 nm. mCherry fluorescence was normalized to cell growth ($OD_{600}$).

RBS strength optimization for toxin expression. To optimize cell death dynamics upon Deadman or Passcode circuit activation, a range of predicted RBS strength variants[18] was generated for each toxin (Table 1). For the Deadman kill switches (FIGS. 6A-6B), RBS variants and the corresponding toxin genes ecoRI, ccdB, and mazF, were cloned into pDM3 to replace mcherry. Overnight cultures were grown in the presence of ATc and then transferred into media with ATc (survival condition) or with IPTG (induced death condition). A SpectraMax M5 microplate reader (Molecular Devices) was used to measure cell growth ($OD_{600}$) every 15 min for 15 hours, and the cell growth ratios of the induced death state to the survival state were calculated at 15 hours.

For Passcode kill switches, RBS variants (Table 1) and the corresponding toxin genes ecoRI and mf-lon were cloned into pREPORT to replace gfp and tested for optimal expression under regulation by the hybrid TFs LacI-ScrR, GalR-ScrR and CelR-ScrR. Plasmids containing each RBS-toxin variant were transformed into cells constitutively expressing LacI-ScrR, GalR-ScrR, or CelR-ScrR, grown overnight without inducers, and then transferred into media with or without the appropriate inducer (1 mM IPTG, 20 mM galactose, or 5 mM cellobiose for cells containing LacI-ScrR, GalR-ScrR, or CelR-ScrR, respectively). Cell growth analysis was performed as described for the Deadman circuit above, and the cell growth ratio was calculated at 12 hours. Representative data are shown in FIG. 21.

RBS strength optimization for ScrR ESM-containing TFs. A range of RBS variants was tested to optimize the expression of ScrR ESM-containing TFs (see TF 'C' in FIG. 4A) in the Passcode circuits (Table 1). Cells with the Passcode circuit harboring RBS variants were transformed with the indicated pREPORT plasmid, grown overnight under survival conditions (see FIGS. 20A-20C for the appropriate inducers for each circuit), and then transferred to media with all 8 combinations of the three inducers (IPTG, galactose, and cellobiose). Performance of each circuit was determined by CFU count after 8 hours of exposure as described in the Methods section.

Long-term growth analysis. Cells containing the Deadman and Passcode kill switches were passaged under survival conditions for 4 days (Deadman: 100 ng/mL ATc; Passcode: unique inducer for each Passcode circuit; see FIGS. 20A-20C). Sub-populations of these cells were transferred 1:20,000 into media with or without the survival signal(s) (Deadman: no ATc; Passcode: no inducers), and samples were collected at 8 hours after inoculation, serially diluted 1:10 in PBS over a 7-log range, and spotted (5 μL) onto LB agar plates with the appropriate survival signal(s). CFU and survival ratios were calculated as previously reported[15]: CFU/mL=(number of colonies)×(dilution factor)/0.005 mL; survival ratio $(\log_{10})$=log {(CFU/mL without the survival signal(s))/(CFU/mL with the survival signal(s))}.

Escapee genetic analysis. Cells containing independent Deadman and Passcode circuit transformants (n=10 for each circuit) were grown under survival conditions (Deadman: 100 ng/mL ATc; Passcode: unique inducer for each Passcode circuit; see FIGS. 20A-20C). The cells were then transferred to media without the survival signal(s) for 8 hours and then placed on LB agar plates containing the appropriate survival signal(s). Deadman circuits were isolated from surviving cells by amplification with Phusion high-fidelity DNA polymerase (NEB), and Passcode circuits were isolated by plasmid DNA purification, and the circuits were then sequenced by QUINTARA BIOSCIENCES (Boston, Mass.).

Flow cytometry. Cells containing Deadman and Passcode circuits were grown as described for each experiment, and at the appropriate time they were fixed in 2% paraformaldehyde in PBS and then diluted 1:10 in PBS for analysis. GFP and mCherry fluorescence measurements were performed using a BD FACSARIAll (FIGS. 7A-9B, 15, 17, 18, 24A-25; BD BIOSCIENCES) or a BD LSRFORTESSA™ flow cytometer (FIGS. 16A-16C, 19, and 20; BD BIOSCIENCES). Flow cytometry data were gated by forward and side scatter to eliminate multi-cell aggregates, and the geometric mean of GFP and mCherry fluorescence distributions were calculated using FLOWJO software (TREESTAR). At least 10,000 events were collected for each measurement.

Supplementary References

1 Swint-Kruse, L. & Matthews, K. S. Allostery in the LacI/GalR family: variations on a theme. *Current opinion in microbiology* 12, 129-137, doi:10.1016/j.mib.2009.01.009 (2009).
2 Finn, R. D. et al. Pfam: the protein families database. *Nucleic acids research* 42, D222-230, doi:10.1093/nar/gkt1223 (2014).
3 Jarcma, M. A., Lu, P. & Miller, J. H. Lac repressor: a genetic and nuclear magnetic resonance study of structure and function. *Biophysical journal* 32, 450-452 (1980).
4 Jarema, M. A., Lu, P. & Miller, J. H. Genetic assignment of resonances in the NMR spectrum of a protein: lac repressor. *Proceedings of the National Academy of Sciences of the United States of America* 78, 2707-2711 (1981).
5 Lewis, M. et al. Crystal structure of the lactose operon repressor and its complexes with DNA and inducer. *Science* 271, 1247-1254 (1996).
6 Bell, C. E. & Lewis, M. A closer view of the conformation of the Lac repressor bound to operator. *Nature structural biology* 7, 209-214, doi:10.1038/73317 (2000).Friedman, A. M., Fischmann, T. 0. & Steitz, T. A. Crystal structure of lac repressor core tetramer and its implications for DNA looping. *Science* 268, 1721-1727 (1995).
8 Meinhardt, S. & Swint-Kruse, L. Experimental identification of specificity determinants in the domain linker of a LacI/GalR protein: bioinformatics-based predictions generate true positives and false negatives. *Proteins* 73, 941-957, doi:10.1002/prot.22121 (2008).
9 Meinhardt, S. et al. Novel insights from hybrid LacI/GalR proteins: family-wide functional attributes and biologically significant variation in transcription repression. *Nucleic acids research* 40, 11139-11154, doi:10.1093/nar/gks806 (2012).
10 Lutz, R. & Bujard, H. Independent and tight regulation of transcriptional units in *Escherichia coli* via the LacR/O, the TetR/O and AraC/I1-I2 regulatory elements. *Nucleic acids research* 25, 1203-1210 (1997).
11 Csorgo, B., Feher, T., Timar, E., Blattner, F. R. & Posfai, G. Low-mutation-rate, reduced-genome *Escherichia coli*: an improved host for faithful maintenance of engineered genetic constructs. *Microbial cell factories* 11,11, doi: 10.1186/1475-2859-11-11 (2012).
12 Larkin, M. A. et al. Clustal W and Clustal X version 2.0. *Bioinformatics* 23, 2947-2948, doi:10.1093/bioinformatics/btm404 (2007).
13 Schumacher, M. A., Choi, K. Y., Lu, F., Zalkin, H. & Brennan, R. G. Mechanism of corepressor-mediated specific DNA binding by the purine repressor. *Cell* 83, 147-155 (1995).
14 Glasfeld, A., Koehler, A. N., Schumacher, M. A. & Brennan, R. G. The role of lysine 55 in determining the specificity of the purine repressor for its operators through minor groove interactions. *Journal of molecular biology* 291, 347-361, doi:10.1006/jmbi.1999.2946 (1999).
15 Callura, J. M., Dwyer, D. J., Isaacs, F. J., Cantor, C. R. & Collins, J. J. Tracking, tuning, and terminating microbial physiology using synthetic riboregulators. *Proceedings of the National Academy of Sciences of the United States of America* 107, 15898-15903, doi:10.1073/pnas.1009747107 (2010).
16 Baba, T. et al. Construction of *Escherichia coli* K-12 in-frame, single-gene knockout mutants: the Keio collection. *Molecular systems biology* 2, 2006 0008, doi: 10.1038/msb4100050 (2006).
17 Cameron, D. E. & Collins, J. J. Tunable protein degradation in bacteria. *Nature biotechnology* 32, 1276-1281, doi:10.1038/nbt.3053 (2014).
18 Salis, H. M. The ribosome binding site calculator. *Methods in enzymology* 498, 19-42, doi:10.1016/B978-0-12-385120-8.00002-4 (2011).

TABLE 1

DNA sequences of genes, promoters, and ribosomal binding site.

| Name | Sequence (5' to 3') (Cloned into pDM2L between 9396 to 9397) | Source | SEQ ID NO: |
|---|---|---|---|
| DNA fragments used to construct the Deadman kill switch ||||
| rnpB T1 terminator +pTrc-2 derivative promoter +RBS (bold) | ccggcttatcggtcagtttcacctgatttacgtaaaaacccgcttcggcgggttttgcttttggaggg gcagaaagatgaatgactgtccacgacgctataccaaaagaaagagctcggactggactcgaa ttgtgagcgctcacaattactagcggccgcatggaattgtgagcgctcacaatttgacaattaatca tccggctcgtataatgtgtgggaattgtgagcgctcacaatttcacacaattgataatatacaag attaaggaggtaaagaatggtgagcaagggcgaggaggataacatggccatcatcaaggagt tcatgcgcttcaaggttcacatggagggctccgtgaacggccacgagttcgagatcgagggcga gggcgagggccgcccctacgagggcacccagaccgccaagctgaaggtgaccaagggtggc | rnpB T1 terminator, BBa_J61048; pTrc-2 derivative and RBS, this study; | 1 |

TABLE 1-continued

DNA sequences of genes, promoters, and ribosomal binding site.

| | | | |
|---|---|---|---|
| +mCherry +3'UTR | cccctgccctcgcctgggacatcctgtcccctcagttcatgtaccggctccaaggcctacgtgaag caccccgccgacatccccgactacttgaagctgtccttccccgaggggcttcaagtgggagcgcgt gatgaacttcgaggacggcggcgtggtgaccgtgacccaggactcctccctgcaagacggcgca gttcatctacaaggtgaagctgcgcggcaccaacttcccctccgacggccccgtaatgcagaaga agactatgggctgggaggcctcctccgagcggatgtaccccgaggacggcgcgctgaagggc gagatcaagcagaggctgaagctgaaggacggcggccactacgacgctgaggtcaagaccac ctacaaggccaagaagcccgtgcaactgcccggcgcgtacaacgtcaacatcaagttggacatc acctcccacaacgaggactacaccatcgtggaacagtacgaacgcgccgagggccgccactcc accggcggcatggacgagctgtataagtaagatatctatcgccctagggaccgt | mCherry, pECJ3[17] | |
| rnpB T1 terminator +pTrc-2 derivative promoter +RBS (bold) +ecoRI +3' UTR | ccggcttatcggtcagtncacctgatttacgtaaaaacccgcttcggcgggtttttgcttttggaggg gcagaaagatgaatgactgtccacgacgctatacccaaaagaaagagctcggactggactcgaa ttgtgagcgctcacaattactagcggccgcatggaattgtgagcgctcacaattttgacaattaatca tccggctcgtataatgtgtgggaattgtgagcgctcacaatttcacaccaattgtaacagtggaaa catggattcatgtctaataaaaacagtcaaataggctaactgaacaacataagttatctcaaggtg taattgggattttttggggattatgcaaaagctcatgatctcgctgttggtgaggtncaaaattagtaaa gaaagctcttagcaacgaataccctcaattatcatttcgatatagaagtagtataaagaaaacagaa ataaatgaagattaaaaaaaattgaccctgatcttggcggtactnatngtttcaaattccagcatca aacctgatggtggaattgtagaggtcaaagatgattatggtgaatggagagttgtacttgttgctgaa gccaaacaccaaggtaaagatattataaatataaggaatggtngttagttgggaaaagaggagat caagatttaatggctgctggtaatgctatcgaaagatctcataagaatatatcagagatagcgaa atgctctgagagccacttcccttacgtcctttcttagagggggtctaacttttt-taacagaaaatctc aataacaagaccagatgaagggttgttaatcttgagtataattctggtatattaaataggnagatcg actaactgcagctaattatggaatgcctataaatagtaatctatgtattaacaaatngtaaatcataaa gacaaaagcattatgctacaagcagcatctatatatactcaaggagatgggagggagtgggattc gaaaatcatgtttgaaataatgtttgatatatcaacgacttcgctcagagtgttggggcgtgacttgttt gaacagcttacatctaagtgactcgagggtcttgataat | ecoRI, pSCC2 (Addgene plasmid # 39993) | 2 |
| rnpB T1 terminator +pTrc-2 derivative promoter +RBS (bold) +ccdB +3' UTR | ccggcttatcggtcagtncacctgatttacgtaaaaacccgcttcggcgggtttttgcttttggaggg gcagaaagatgaatgactgtccacgacgctatacccaaaagaaagagctcggactggactcgaa ttgtgagcgctcacaattactagcggccgcatggaattgtgagcgctcacaattttgacaattaatca tccggctcgtataatgtgtgggaattgtgagcgctcacaatttcacaccaattgattaaagcccat aacagtaccatgcagtnaaggtnacacctataaaagagagagccgttatcgtctgtttgtggatgt acagagtgatattattgacacgcccgggcgacggatggtgatcccctggccagtgcacgtctgc tgtcagataaagtctcccgtgaactttacccggtggtgcatatcggggatgaaagctggcgcatga tgaccaccgatatggccagtgtgccggtctccgttatcggggaagaagtggctgatctcagccac cgcgaaaatgacatcaaaaacgccattaacctgatgttctggggaatataactcgagggtcttgata at | ccdB, RR12(14)Cc dB[15] | 3 |
| rnpB T1 terminator +pTrc-2 derivative promoter +RBS (bold) +mazF +3' UTR | ccggcttatcggtcagtttcacctgatttacgtaaaaacccgcttcggcgggtttttgcttttggaggg gcagaaagatgaatgactgtccacgacgctatacccaaaagaaagagctcgaactggactcgaa ttgtgagcgctcacaattactagcggccgcatggaattgtgagcgctcacaattttgacaattaatca tccggctcgtataatgtgtgggaattgtgagcgctcacaatttcacaccaattgtaactgggaaag ataacggagactggtaatggtaagccgatacgtacccgatatgggcgatctgataggttgata tgacccgacaaaaggtagcgagcaagctggacatcgtccagctgttgtcctgagtcctncatgta caacaacaaaacaggtatgtgtctgtgtgttccttgtacaacgcaatcaaaaggatatccgttcgaa gttgttttatccggtcaggaacgtgatggcgtagcgttagctgatcaggtaaaaagtatcgcctggc gggcaagaggagcaacgaagaaaggaacagttgccccagaggaattacaactcattaaagcca aaattaacgtactgattgggtaat | mazF, Escherichia coli K-12 MG1655 | 4 |

RBS used to design monostable toggle

| | | | |
|---|---|---|---|
| L1 | (NcoI)aacgggcggccgtcccctatcagtgatagagattgacatccctatcagtgatagatatact gagcacatcagcaggacgcactgaccggaggatagaaaatcaagaattaaggaggtacaatA TG | This study | 5 |
| L2 | (NcoI)aactctagtgtaccctatcagtgatagagattgacatccctatcagtgatagatatactga gcacatcagcaggacgcactgaccgctgataagccgaggatagaaaatcaagaattaaggaggt acaatATG | This study | 6 |
| L3 | (NcoI)aacgggcggccgtcccctatcagtgatagagattgacatccctatcagtgatagatatact gagcacatcagcaggacgcactgaccgctcacatgacgaggatagaaaatcaagaattaagga ggtacaatATG | This study | 7 |
| T1 | (NcoI)ctgaaatgagctgttgacaattaatcatccggctcgtataatgtgtggaattgtgagcgga taacaatttcacacgtcgaccgcctcggcgaagctagggacgagagctagcATG | This study | 8 |
| T2 | (NcoI)ctgaaatgagctgttgacaattaatcatccggctcgtataatgtgtggaattgtgagcgga taacaatttcacacgtcgacgcaccgggaggcggaaagtaaggaggttagatATG | This study | 9 |
| T3 | (NcoI)ctgaaatgagctgttgacaattaatcatccggctcgtataatgtgtggaattgtgagcgga taacaatttcacacgtcgacgcaccataaagcggaaagtaaggaggttagatATG | This study | 10 |

TABLE 1-continued

DNA sequences of genes, promoters, and ribosomal binding site.

| Name | Sequence (5' to 3') (Restriction sites in parentheses, RBS region in bold) | Source | |
|---|---|---|---|
| RBS tested for EcoRI expression | | | |
| ecoRI-50 | (MfeI) ctaggagctacagataacctttcttattagaaggATG | This study | 11 |
| ecoRI-200 | (MfeI) acgcaattcgtaagaacagatatattcccagtaatATG | This study | 12 |
| ecoRI-1500 | (MfeI) taacagtggaaacatggattcATG | This study | 13 |
| ecoRI-5000 | (MfeI) tatcgcatctaaagcggaattaacgataaaagcATG | This study | 14 |
| ecoRI-15000 | (MfeI) ataaagagaattaagatcaataaaggatatctcttATG | This study | 15 |
| RBS tested for CcdB expression | | | |
| ccdB-50 | (MfeI) gcgagaaagtaatcatccgcattataggttaATG | This study | 16 |
| ccdB-500 | (MfeI) attaaagcccataacagtaccATG | This study | 17 |
| ccdB-1500 | (MfeI) tttacaaaataatttattaacatcgcgcgtatATG | This study | 18 |
| ccdB-5000 | (MfeI) tcatcacaaataatcagatactaagagccccaaATG | This study | 19 |
| RBS tested for MazF expression | | | |
| mazF-50 | (MfeI) ggagaaataccactcagactctcatccataaATG | This study | 20 |
| mazF-200 | (MfeI) ataaaaattacaacatagacctacaggaaatctATG | This study | 21 |
| mazF-1000 | (MfeI) taactgggaaagataacggagactggtaATG | This study | 22 |
| mazF-5000 | (MfeI) gacacaacgctaacataaggacgcaatttcaaATG | This study | 23 |
| mazF-15000 | (MfeI) cagactaatctaaaataattaagccggaggcgcaaATG | This study | 24 |
| DNA fragments used to construct the Passcode circuit | | | |
| pLlacO | (XhoI) ttgacaattgtgagcgctcacaagatactgagcacatcagcaggacgcactgacc (AvrII) | This study | 25 |
| pLscrO-1 | (EagI) ttattaaaccggtttagcattgacaattaaaccggtttagcagatactgagcacatcagcaggacgcactgacc(MfeI) | This study | 26 |
| pLscrO-2 | (EagI) catttattaaaccggtttattgacataaaccggtttagcatagatactgagcacatcagcaggacgcactgacc(MfeI) | This study | 27 |
| RBS+lacI-lacI | (SacI) atcagcaggacgcactgaccggatccatgaaaccagtaacgttatacgatgtcgcagagtatgccggtgtctcttatcagaccgtacccgcgtggtgaaccaggccagccacgtactgcgaaacgcgggaaaaagtggaagcggcgatggcggagctgaattacattcccaaccgcgtggcacaacaactggcgggcaaacagtcgttgctgattggcgttgccacctccagtctggccctgcacgcgccgtcgcaaattgtcgcggcgattaaatctcgcgccgatcaactgggtgccagcgtggtggtgtcgatggtagaacgaagcggcgtcgaagcctgtaaagcggcggtgcacaatcttctcgcgcaacgcgtcagtgggctgatcattaactatccgctggatgaccaggatgccattgctgtggaagctgcctgcactaatgttccggcgttatttcttgatgtctctgaccagacacccatcaacagtattatttttctcccatgaagacggtacgcgactgggcgtggagcatcggtcgcattcaccagcaaatcgcgctgttagcgggcccattaagttctgtctcggcgcgtctgcgtctggctggctggcataaatatctcactcgcaatcaaattcagccgatagcggaacgggaaggcgactgagtgccatgtccggttttcaacaaaccatgcaaatgctgaatgagggcatcgttcccactgcgatgctggttgccaacgatcagatggcgctggcgcaatgcgcgccattaccgagtccgggccgcgttggtgcggatatctcggtagtgggatacgacgataccgaagacagctcatgttatatcccgccgttaaccaccatcaaacaggattttcgcctgctggggcaaaccagcgtggaccgcttgctgcaactctctcagggccaggcggtgaagggcaatcagctgttgcccgtctcactggtgaaaagaaaaaccaccctggcgcccaatacgcaaaccgcctctccccgcgcgttggccgattcattaatgcagctggcacgacaggtacccgactggaaagcgggcagtga(BsrGI) | Escherichia coli K-12 MG1655 | 28 |
| RBS+galR-lacI | (SacI) atcagcaggacgcactgaccggatccatgaaaccagtaacgttatacgatgtcgcagagtatgccggtgtctcttatcagaccgtacccgcgtggtgaaccaggccagccacgtactgcgaaacgcgggaaaaagtggaagcggcgatggagtctcttagctctatcacccgaacgccaacgcccgtgcgctggcgcagcagaccactgaaacggtcggtctggtcgttggtgatgtttccgatccgttttcggtgcaatggtgaaagcggtcgaacaggtggcttatcacaccggtaattttttattgattggcaacggttaccacaacgaacaaaaagagcgtcaggccattgagcaactgatccgccatcgctgtgctgcgttggtcgtccatgccaaaatgatcccggatgctgatttagcctcattaatgaaacaaatgcccggtat | This study | 29 |

TABLE 1-continued

DNA sequences of genes, promoters, and ribosomal binding site.

|  |  |  |  |
|---|---|---|---|
|  | ggtgctgatcaaccgtatcctgcctggctttgaaaaccgttgtattgctctggacgatcgttacggtg<br>cctggctggcaacgcgtcatttaattcagcaaggtcataccgcattggttatctgtgctctaaccac<br>tctatttctgacgccgaagatcgtctgcaagggtattacgatgcccttgctgaaagtggtattgcggc<br>caatgaccggctggtgacatttggcgaaccagacgaaagcggcggcgaacaggcaatgaccg<br>agcttttgggacgaggaagaaatttcactgcggtagcctgttataacgattcaatggcggcgggtg<br>cgatgggcgttctcaatgataatggtattgatgtaccgggtgagatttcgttaattggctttgatgatgt<br>gctggtgtcacgctatgtgcgtccgcgcctgaccaccgtgcgttacccaatcgtgacgatggcga<br>cccaggctgccgaactggctttggcgctggcggataatcgccctctcccggaaatcactaatgtct<br>tagtccgacgctggtacgtcgtcattcagtgtcaactccgtcgctggaggcaagtcatcatgcaac<br>cagcgactaa(BsrGI) |  |  |
| RBS+celR-<br>lacI | (SacI) atcagcaggacgcactgaccggatccatgaaaccagtaacgttatacgatgtcgcaga<br>gtatgccggtgtctcttatcagaccgtacccgcgtggtgaaccaggccagccacgtactgcgaaa<br>acgcgggaaaaagtggaagcggcgatcaaagagctgggctacgtgccgaaccgcgcagccc<br>gcaccctggtcacccgaccgtaccgacaccgtagccctggtggtgtcggaaaaacaaccagaagct<br>cttcgccgaaccccttctatgccgggatcgtgctcggcgtgggggttgctctgtccgaacggggatt<br>ccagttcgtcctggccacgggccgctccgggatagagcatgagcggctgggcggctacctggc<br>cggacagcacgtcgacggggtcctcctgctgtcgctccaccgcgacgacccgctgccgcagat<br>gctggacgaggccggggtgcgtacgtctacgggcgctccgctcggcgtccccgaagaac<br>aggtgtcctatgtcgatatcgacaacatcggcggggacgccaggccacccagcggctgatcga<br>gaccgggcaccggcggatcgctacgatcgcgggcccgcaggacatggtcgctggtgtggaac<br>gcctccaggggtatcgcgaagcactgctcgccgcggggatggagtacgacgagacgctggtga<br>gctacggtgacttcacctacgacgcggggtggccgcgatgcgggagctgctggatcgggccc<br>ccgacgtggacgccgtgttcgcggcctccgacttgatggggctggccgcgctgcgggtgctgcg<br>tgcttcgggacgccgcgtgcccgaggatgtggcggtggtcggctacgacgactcgaccgtagc<br>cgagcacgccgaaccgccgatgaccagcgtcaaccagcccaccgagctgatgggccgggag<br>atggcccggctgctcgtggaccggatcaccggggagaccaccgaaccggtgcggctggtgctg<br>gagacccatttgatggtgcgggaatcccgggtga(3srGI) | This study | 30 |
| RBS+lacI-<br>scrR | (AvII) ctctagccatttttataggatcttaagatgaaaaccaaacgcgtaactatcaaagatatc<br>gccgaactggcgggcgtctccaaagcgaccgccagtctggtgctcaacggccgtggcaaagag<br>ctgcgcgtggcgcaggagacgcgcgagcgcgtgctggcgatcatggcgggagctgaattacatt<br>cccaaccgcgtggcacaacaactggcgggcaaacagtcgttgctgattggcgttgccacctcca<br>gtctgggccctgcacgcgccgtcgcaaattgtcgcggcgattaaatctcgcgccgatcaactgggt<br>gccagcgtggtggtgtcgatggtagaacgaagcggcgtcgaagcctgtaaagcggcggtgcac<br>aatcttctcgcgcaacgcgtcagtgggctgatcattaactatccgctggatgaccaggatgccattg<br>ctgtggaagctgcctgcactaatgttccggcgttatttcttgatgtctctgaccagacacccatcaac<br>agtattattttctcccatgaagacggtacgcgactgggcgtggagcatctggtcgcattgggtcacc<br>agcaaatcgcgctgttagcgggcccattaagttctgtctcggcgcgtctgcgtctggctggctggc<br>ataaatatctcactcgcaatcaaattcagccgatagcggaagggaaggcgactggagctcatg<br>tccggttttcaacaaaccatgcaaatgctgaatgagggcatcgttcccactgcgatgctggttgcca<br>acgatcagatggcgctgggcgcaatgcgcgccattaccgagtccgggctgcgcgttggtgcgg<br>atatctcggtagtgggatacgacgataccgaagacagctcatgttatatcccgccgttaaccaccat<br>caaacaggattttcgcctgctggggcaaaccagcgtggaccgcttgctgcaactctctcagggcc<br>aggcggtgaagggcaatcagctgttgcccgtctcactggtgaaaagaaaaaccaccctggcgcc<br>caatacgcaaaccgcctctccccgcgcgttggccgattcattaatgcagctggcacgacaggtttc<br>ccgactggaaagcgggcagtga(XmaI) | This study | 31 |
| RBS+galR-<br>scrR | (AvrII) ggtcaagagtcaagaggaggcttaagatgaaaaccaaacgcgtaactatcaaagat<br>atcgccgaactggcgggcgtctccaaagcgaccgccagtctggtgctcaacggccgtggcaaa<br>gagctgcgcgtggcgcaggagacgcgcgagcgcgtgctggcgatcatggagtctcttagctatc<br>acccgaacgccaacgcccgtcgcgctggcgcagcagaccactgaaacggtcggtctggtcgttg<br>gtgatgtttccgatccgttttcggtgcaatggtgaaagcggtcgaacaggtggcttatcacaccgg<br>taattttttattgattggcaacggttaccacaacgaacaaaaagagcgtcaggccattgagcaactg<br>atccgccatcgctgtgctgcgttggtcgtccatgccaaaatgatcccggatgctgatttagcctcatt<br>aatgaaacaaatgcccggtatggtgctgatcaaccgtatcctgcctggctttgaaaaccgttgtattg<br>ctctggacgatcgttacggtgcctggtggcaacgcgtcatttaattcagcaaggtcatacccgcat<br>tggttatctgtgctctaaccactctatactgacgccgaagatcgtctgcaagggtattacgatgccct<br>tgctgaaagtggtattgcggccaatgaccggctggtgacataggcgaaccagacgaaagcggc<br>ggcgaacaggcaatgaccgagcttttgggacgaggaagaaatttcactgcggtagcctgttataa<br>cgattcaatggcggcgggtgcgatgggcgttctcaatgataatggtattgatgtaccgggtgagatt<br>tcgttaattggctttgatgatgtgctggtgtcacgctatgtgcgtccgcgcctgaccaccgtgcgtta<br>cccaatcgtgacgatggcgacccaggctgccgaactggctttggcgctggcggataatcgccct<br>ctcccggaaatcactaatgtctttagtccgacgctggtacgtcgtcattcagtgtcaactccgtcgct<br>ggaggcaagtcatcatgcaaccagcgactaa | This study | 32 |
| RBS+celR-<br>scrR | (AvrII) ctctagccatttttataggatcttaagatgaagacgaaacgcgtaaccattaaagatatc<br>gcggaattagctggggtgagtaaagcaacggcaagtcttgttcttaatggtcgtggtaaagaactg<br>cgtctcgcccaggaaacccgtgagcgcgtgctggctattatcaaagaactcggttacgtcccgaa<br>tcgcgcggcacgcacattggttacacgccgcacggacaccgtggctaggtggtgtccgaaaata<br>accagaaactgtttgcggaaccgttttatgcaggtatcgtgctgggtgtcggtgtggctctgagtga<br>acgtggtttccagttcgtcctggctacgggtcgttcgggcattgagcacgaacgcctgggggggct<br>atctggcaggccagcatgtggacggcgtgctgcttcttagtttgcaccgcgacgatccgctgccg<br>cagatgctggacgaagctggagtaccgtatgtatatgtggcgcccgctgggtgtgccggaag<br>agcaggtcagctatgtcgatatcgacaatattggtggcgggcgccaggctacccagcgtctgatc<br>gaaacgggtcatcgtcgtatcgcgactattgccggcccgcaagatggtggcaggagtagagc<br>gtctgcaaggataccgtgaggcattattagccgcgggcatggaatacgatgaaacattagtatcat<br>atggtgactttacgtatgattcgggcgtcgccgccatgcgcgaacttctgaccgcgcaccggat | This study | 33 |

TABLE 1-continued

DNA sequences of genes, promoters, and ribosomal binding site.

gtggatgccgtattcgcagcatctgatcttatggggctggcggcgttacgtgtactgcgtgcatcgg
ggcgccgtgtgcctgaagatgtcgcggtcgttgggtacgacgattcgacggtggcggaacacgc
ggaaccccccatgacgagcgtcaaccagccgacagaattaatgggtcgtgagatggctcgtagc
ttgtagatcgtattacaggcgaaactacggaaccggttcgtaggtactcgaaactcatttaatggttc
gcgaaagtgggtaa(XmaI)

Promoter and RBS for toxin expression regulation used with pPasscode1 (CelR-LacI, GalR-LacI, and CelR-ScrR)

| Name | Sequence (5' to 3') (Restriction sites in parentheses, RBS region in bold) | Source | |
|---|---|---|---|
| ecoRI | (EagI)catttattaaaccggtttattgacataaaccggtttagcatagatactgagcacatcagcaggacgcactgacccaattgctcacaaccacgaaggaaca(BamHI) | This study | 34 |
| mf-lon | (XhoI)catttattaaaccggtttattgacataaaccggtttagcatagatactgagcacatcagcaggacgcactgaccgaattcgtatctagga(KpnI) | This study | 35 |

| Name | Sequence (5' to 3') (Restriction sites in parentheses, RBS region in red) | Source | |
|---|---|---|---|
| Promoter and RBS for toxin expression regulation used with pPasscode2 (LacI-LacI, CelR-LacI, and GalR-ScrR) | | | |
| ecoRI | (EagI)ttattaaaccggtttagcattgacaattaaaccggtttagcagatactgagcacatcagcaggacgcactgacccaattgtcaggaataggcccgtcgcc(BamHI) | This study | 36 |
| mf-lon | (XhoI)ttattaaaccggtttagcattgacaattaaaccggtttagcagatactgagcacatcagcaggacgcactgaccgaattccagttacaggtcac(KpnI) | This study | 37 |

| Name | Sequence (5' to 3') (Restriction sites in parentheses, RBS region in bold) | Source | |
|---|---|---|---|
| Promoter and RBS for toxin expression regulation used with pPasscode3 (GalR-LacI, LacI-LacI, and CelR-ScrR) | | | |
| ecoRI | (EagI)catttattaaaccggtttattgacataaaccggtttagcatagatactgagcacatcagcaggacgcactgacccaattgtcaggaataggcccgtcgcc(BamHI) | This study | 38 |
| mf-lon | (XhoI)ttattaaaccggtttagcattgacaattaaaccggtttagcagatactgagcacatcagcaggacgcactgaccgaattcgtatctagga(KpnI) | This study | 39 |
| RBS tested for EcoRI expression | | | |
| ecoRI-200 | (MfeI)tcaggaataggcccgtcgcc(BamHI) | This study | 40 |
| ecoRI-1000 | (MfeI)taccgataacgaccgaaag(BamHI) | This study | 41 |
| ecoRI-10000 | (MfeI)tggcacaaacctaagtagggc(BamHI) | This study | 42 |
| ecoRI-40000 | (MfeI)ctcacaaccacgaaggaaca(BamHI) | This study | 43 |
| ecoRI-80000 | (MfeI)ctaaggatcgaacacgggag(BamHI) | This study | 44 |
| RBS tested for mf-Lon expression | | | |
| mf-lon-500 | (EcoRI)cagttacaggtcac(KpnI) | This study | 45 |
| mf-lon-1000 | (EcoRI)gcggccgcgactc(KpnI) | This study | 46 |
| mf-lon-10000 | (EcoRI)gacgcaaaaggcaa(KpnI) | This study | 47 |
| mf-lon-30000 | (EcoRI)ggtcggtcttcggg(KpnI) | This study | 48 |
| mf-lon-100000 | (EcoRI)gtatctagga(KpnI) | This study | 49 |
| RBS tested for TF C (ScrR ESM-containing TFs) | | | |
| scrR-2000 | (AyrII)ggcgcaaccaagtcctaggt(AflII) | This study | 50 |
| scrR-10000 | (AyrII)ctctagccatttataggat(AflII) | This study | 51 |
| scrR-25000 | (AyrII)gggccgcattaggagggtac(AflII) | This study | 52 |

TABLE 1-continued

DNA sequences of genes, promoters, and ribosomal binding site.

| scrR-100000 | (AyrII)ggtcaagagtcaagaggagg(AflII) | This study | 53 |
| scrR-150000 | (AvrII)acttacttataataaggagg(AflII) | This study | 54 |

We claim:

1. A system to render cell growth restricted to the presence of a predetermined set of at least two selected input agents, the system comprising a nucleic acid construct encoding expression modules comprising:
   i) a toxin expression module comprising a nucleic acid sequence that encodes a toxin that is toxic to a host cell, wherein the nucleic acid sequence encoding the toxin is operably linked to a promoter P1 that comprises a nucleic acid binding site for and is repressed by the binding of a first hybrid repressor protein hRP1; and
   ii) a first hybrid repressor protein expression module comprising a nucleic acid sequence that encodes the first hybrid repressor protein hRP1, wherein the first hybrid repressor protein expression module further comprises a nucleic acid binding site for two hybrid transcription factors (hTF1 and hTF2),
      wherein the first of the two hybrid transcription factors (hTF1) comprises a binding site for an input agent $A_1$,
      wherein the second of the two hybrid transcription factors (hTF2) comprises a binding site for an input agent $A_2$,
      wherein expression of hRP1 is controlled by an AND gate formed by the two hybrid transcription factors hTF1 and hTF2, the binding or activity of which is responsive to input agents $A_1$ and $A_2$, respectively, such that both input agents $A_1$ and $A_2$ are required for expression of hRP1,
      wherein hybrid factors hTF1, hTF2 and hybrid repressor protein hRP1 each comprise:
      (a) an environmental sensing module from one LacI/GalR family transcription factor selected from the group consisting of LacI, GalR, ScrR and CelR and
      (b) a DNA recognition module (DRM) from a different LacI/GalR family transcription factor selected from the group consisting of LacI, GalR, ScrR and CelR that renders the binding of the respective DRM sensitive to the presence of an environmental input agent, $A_1$, or $A_2$, selected from the group consisting of Isopropyl β-D-1-thiogalactopyranoside (IPTG), galactose and cellobiose, that is different from that which the respective DRM binds in nature and
      wherein, when introduced to a host cell in the absence of either $A_1$ or $A_2$, hRP1 expression is insufficient to repress toxin promoter module P1 and toxin production, such that the host cell is killed.

2. A method of restricting cell growth to require the presence of a predetermined set of at least two selected input agents, the method comprising introducing the system of claim 1 to a host cell.

* * * * *

SEQUENCE LISTING

<160> NUMBER OF SEQ ID NOS: 70

<210> SEQ ID NO 1
<211> LENGTH: 1018
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
ccggcttatc ggtcagtttc acctgattta cgtaaaaacc cgcttcggcg ggttttttgct      60
tttggagggg cagaaagatg aatgactgtc cacgacgcta tacccaaaag aaagagctcg     120
gactggactc gaattgtgag cgctcacaat tactagcggc cgcatggaat tgtgagcgct     180
cacaattttg acaattaatc atccggctcg tataatgtgt gggaattgtg agcgctcaca     240
atttcacacc aattgataat atacaagatt aaggaggtaa agaatggtga gcaagggcga     300
ggaggataac atggccatca tcaaggagtt catgcgcttc aaggttcaca tggagggctc     360
cgtgaacggc cacgagttcg agatcgaggg cgagggcgag ggccgcccct acgagggcac     420
ccagaccgcc aagctgaagg tgaccaaggg tggccccctg cccttcgcct gggacatcct     480
gtcccctcag ttcatgtacg gctccaaggc ctacgtgaag caccccgccg acatccccga     540
ctacttgaag ctgtccttcc ccgagggctt caagtgggag cgcgtgatga acttcgagga     600
cggcggcgtg gtgaccgtga cccaggactc ctccctgcaa gacggcgagt tcatctacaa     660
ggtgaagctg cgcggcacca acttcccctc cgacggcccc gtaatgcaga gaagactat     720
gggctgggag gcctcctccg agcggatgta ccccgaggac ggcgcgctga gggcgagat     780
caagcagagg ctgaagctga aggacggcgg ccactacgac gctgaggtca agaccaccta     840
caaggccaag aagcccgtgc aactgcccgg cgcgtacaac gtcaacatca gttggacat     900
cacctcccac aacgaggact acaccatcgt ggaacagtac gaacgcgccg agggccgcca     960
ctccaccggc ggcatggacg agctgtataa gtaagatatc tatcgcccta gggaccgt    1018
```

<210> SEQ ID NO 2
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
ccggcttatc ggtcagtttc acctgattta cgtaaaaacc cgcttcggcg ggttttttgct      60
tttggagggg cagaaagatg aatgactgtc cacgacgcta tacccaaaag aaagagctcg     120
gactggactc gaattgtgag cgctcacaat tactagcggc cgcatggaat tgtgagcgct     180
cacaattttg acaattaatc atccggctcg tataatgtgt gggaattgtg agcgctcaca     240
```

```
atttcacacc aattgtaaca gtggaaacat ggattcatgt ctaataaaaa acagtcaaat      300
aggctaactg aacaacataa gttatctcaa ggtgtaattg ggattttggg ggattatgca      360
aaagctcatg atctcgctgt tggtgaggtt tcaaaattag taaagaaagc tcttagcaac      420
gaataccctc aattatcatt tcgatataga gatagtataa agaaaacaga ataaatgaa       480 gctttaaaaa aaattgaccc tgatcttggc ggtactttat ttgtttcaaa ttccagcatc      540
aaacctgatg gtggaattgt agaggtcaaa gatgattatg tgaatggag  agttgtactt      600 gttgctgaag ccaaacacca aggtaaagat attataaata taaggaatgg tttgttagtt      660
gggaaaagag gagatcaaga tttaatggct gctggtaatg ctatcgaaag atctcataag      720
aatatatcag agatagcgaa ttttatgctc tctgagagcc actttcctta cgtccttttc      780 ttagagggt ctaacttttt aacagaaaat atctcaataa caagaccaga tggaagggtt       840
gttaatcttg agtataattc tggtatatta aataggttag atcgactaac tgcagctaat      900
tatgaaatgc ctataaatag taatctatgt attaacaaat ttgtaaatca taagacaaa       960 agcattatgc tacaagcagc atctatatat actcaaggag atgggaggga gtgggattcg     1020
aaaatcatgt ttgaaataat gtttgatata tcaacgactt cgctcagagt gttggggcgt     1080
gacttgtttg aacagcttac atctaagtga ctcgagggtc ttgataat                  1128
```

```
<210> SEQ ID NO 3
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ccggcttatc ggtcagtttc acctgattta cgtaaaaacc cgcttcggcg ggttttgct       60 tttgagggg cagaaagatg aatgactgtc cacgacgcta tacccaaaag aaagagctcg      120
gactggactc gaattgtgag cgctcacaat tactagcggc cgcatggaat tgtgagcgct     180
cacaattttg acaattaatc atccggctcg tataatgtgt gggaattgtg agcgctcaca    240
atttcacacc aattgattaa agcccataac agtaccatgc agtttaaggt ttacacctat     300
aaaagagaga gccgttatcg tctgtttgtg gatgtacaga gtgatattat tgacacgccc     360
gggcgacgga tggtgatccc cctggccagt gcacgtctgc tgtcagataa agtctcccgt     420
gaactttacc cggtggtgca tatcggggat gaaagctggc gcatgatgac caccgatatg     480
gccagtgtgc cggtctccgt tatcggggaa gaagtggctg atctcagcca ccgcgaaaat     540
gacatcaaaa acgccattaa cctgatgttc tggggaatat aactcgaggg tcttgataat     600
```

```
<210> SEQ ID NO 4
<211> LENGTH: 620
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ccggcttatc ggtcagtttc acctgattta cgtaaaaacc cgcttcggcg ggttttgct       60 tttgagggg cagaaagatg aatgactgtc cacgacgcta tacccaaaag aaagagctcg      120
gactggactc gaattgtgag cgctcacaat tactagcggc cgcatggaat tgtgagcgct     180
```

```
cacaattttg acaattaatc atccggctcg tataatgtgt gggaattgtg agcgctcaca    240
atttcacacc aattgtaact gggaaagata acggagactg gtaatggtaa gccgatacgt    300
acccgatatg ggcgatctga ttgggttga ttttgacccg acaaaggta gcgagcaagc      360 tggacatcgt ccagctgttg tcctgagtcc tttcatgtac aacaacaaaa caggtatgtg    420
tctgtgtgtt ccttgtacaa cgcaatcaaa aggatatccg ttcgaagttg ttttatccgg    480
tcaggaacgt gatggcgtag cgttagctga tcaggtaaaa agtatcgcct ggcgggcaag    540
aggagcaacg aagaaaggaa cagttgcccc agaggaatta caactcatta aagccaaaat    600
taacgtactg attgggtaat                                                620
```

```
<210> SEQ ID NO 5
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
aacgggcggc cgtccctatc agtgatagag attgacatcc ctatcagtga tagatatact    60
gagcacatca gcaggacgca ctgaccggag gatagaaaat caagaattaa ggaggtacaa    120
tatg                                                                 124
```

```
<210> SEQ ID NO 6
<211> LENGTH: 134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
aactctagtg tttccctatc agtgatagag attgacatcc ctatcagtga tagatatact    60
gagcacatca gcaggacgca ctgaccgctg ataagccgag gatagaaaat caagaattaa    120
ggaggtacaa tatg                                                      134
```

```
<210> SEQ ID NO 7
<211> LENGTH: 134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
aacgggcggc cgtccctatc agtgatagag attgacatcc ctatcagtga tagatatact    60
gagcacatca gcaggacgca ctgaccgctc acatgacgag gatagaaaat caagaattaa    120
ggaggtacaa tatg                                                      134
```

```
<210> SEQ ID NO 8
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
ctgaaatgag ctgttgacaa ttaatcatcc ggctcgtata atgtgtggaa ttgtgagcgg    60
```
ataacaattt cacacgtcga ccgccttcgg cgaagctagg gacgagagct agcatg    116

<210> SEQ ID NO 9
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
ctgaaatgag ctgttgacaa ttaatcatcc ggctcgtata atgtgtggaa ttgtgagcgg    60
ataacaattt cacacgtcga cgcaccggga ggcggaaagt aaggaggtta gatatg    116

<210> SEQ ID NO 10
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
ctgaaatgag ctgttgacaa ttaatcatcc ggctcgtata atgtgtggaa ttgtgagcgg    60
ataacaattt cacacgtcga cgcaccataa agcggaaagt aaggaggtta gatatg    116

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctaggagcta cagataacct ttcttattag aaggatg    37

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
acgcaattcg taagaacaga tatattccca gtaatatg    38

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
taacagtgga aacatggatt catg    24

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 14
tatcgcatct aaagcggaat taacgataaa agcatg                                    36

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ataaagagaa ttaagatcaa taaaggatat ctcttatg                                  38

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcgagaaagt aatcatccgc attataggtt aatg                                      34

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
attaaagccc ataacagtac catg                                                 24

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tttacaaaat aatttattaa catcgcgcgt atatg                                     35

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tcatcacaaa taatcagata ctaagagccc caaatg                                    36

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ggagaaatac cactcagact ctcatccata aatg     34

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ataaaaatta caacatagac ctacaggaaa tctatg     36

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
taactgggaa agataacgga gactggtaat g     31

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gacacaacgc taacataagg acgcaatttc aaatg     35

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cagactaatc taaaataatt aagccggagg cgcaaatg     38

<210> SEQ ID NO 25
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ttgacaattg tgagcgctca caagatactg agcacatcag caggacgcac tgacc     55

<210> SEQ ID NO 26
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 26
ttattaaacc ggtttagcat tgacaattaa accggtttag cagatactga gcacatcagc    60
aggacgcact gacc                                                      74

<210> SEQ ID NO 27
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
catttattaa accggtttat tgacataaac cggtttagca tagatactga gcacatcagc    60
aggacgcact gacc                                                      74

<210> SEQ ID NO 28
<211> LENGTH: 1109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
atcagcagga cgcactgacc ggatccatga aaccagtaac gttatacgat gtcgcagagt    60
atgccggtgt ctcttatcag accgtttccc gcgtggtgaa ccaggccagc cacgtttctg   120
cgaaaacgcg ggaaaaagtg gaagcggcga tggcggagct gaattacatt cccaaccgcg   180
tggcacaaca actggcgggc aaacagtcgt tgctgattgg cgttgccacc tccagtctgg   240
ccctgcacgc gccgtcgcaa attgtcgcgg cgattaaatc tcgcgccgat caactgggtg   300
ccagcgtggt ggtgtcgatg gtagaacgaa gcggcgtcga agcctgtaaa gcggcggtgc   360
acaatcttct cgcgcaacgc gtcagtgggc tgatcattaa ctatccgctg gatgaccagg   420
atgccattgc tgtggaagct gcctgcacta atgttccggc gttatttctt gatgtctctg   480
accagacacc catcaacagt attatttttct cccatgaaga cggtacgcga ctgggcgtgg   540
agcatctggt cgcattgggt caccagcaaa tcgcgctgtt agcgggccca ttaagttctg   600
tctcggcgcg tctgcgtctg gctggctggc ataaatatct cactcgcaat caaattcagc   660
cgatagcgga acgggaaggc gactggagtg ccatgtccgg ttttcaacaa accatgcaaa   720
tgctgaatga gggcatcgtt cccactgcga tgctggttgc caacgatcag atggcgctgg   780
gcgcaatgcg cgccattacc gagtccgggc tgcgcgttgg tgcggatatc tcggtagtgg   840
gatacgacga taccgaagac agctcatgtt atatcccgcc gttaaccacc atcaaacagg   900
attttcgcct gctggggcaa accagcgtgg accgcttgct gcaactctct cagggccagg   960
cggtgaaggg caatcagctg ttgcccgtct cactggtgaa agaaaaaacc accctggcgc  1020
ccaatacgca aaccgcctct ccccgcgcgt tggccgattc attaatgcag ctggcacgac  1080
aggtttcccg actggaaagc gggcagtga                                    1109

<210> SEQ ID NO 29
<211> LENGTH: 1064
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 29

```
atcagcagga cgcactgacc ggatccatga aaccagtaac gttatacgat gtcgcagagt      60
atgccggtgt ctcttatcag accgtttccc gcgtggtgaa ccaggccagc cacgtttctg     120
cgaaaacgcg ggaaaaagtg aagcggcga tggagtctct tagctatcac ccgaacgcca     180
acgcccgtgc gctggcgcag cagaccactg aaacggtcgg tctggtcgtt ggtgatgttt     240
ccgatccgtt tttcggtgca atggtgaaag cggtcgaaca ggtggcttat cacaccggta     300
atttttatt gattggcaac ggttaccaca acgaacaaaa agagcgtcag gccattgagc     360
aactgatccg ccatcgctgt gctgcgttgg tcgtccatgc caaaatgatc ccggatgctg     420
atttagcctc attaatgaaa caaatgcccg gtatggtgct gatcaaccgt atcctgcctg     480
gctttgaaaa ccgttgtatt gctctggacg atcgttacgg tgcctggctg caacgcgtc     540
atttaattca gcaaggtcat acccgcattg gttatctgtg ctctaaccac tctatttctg     600
acgccgaaga tcgtctgcaa gggtattacg atgcccttgc tgaaagtggt attgcggcca     660
atgaccggct ggtgacattt ggcgaaccag acgaaagcgg cggcgaacag gcaatgaccg     720
agcttttggg acgaggaaga aatttcactg cggtagcctg ttataacgat tcaatggcgg     780
cgggtgcgat gggcgttctc aatgataatg gtattgatgt accgggtgag atttcgttaa     840
ttggcttga tgatgtgctg gtgtcacgct atgtgcgtcc gcgcctgacc accgtgcgtt     900
acccaatcgt gacgatggcg acccaggctg ccgaactggc tttggcgctg gcggataatc     960
gccctctccc ggaaatcact aatgtctta gtccgacgct ggtacgtcgt cattcagtgt    1020
caactccgtc gctggaggca agtcatcatg caaccagcga ctaa                   1064
```

<210> SEQ ID NO 30
<211> LENGTH: 1040
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
atcagcagga cgcactgacc ggatccatga aaccagtaac gttatacgat gtcgcagagt      60
atgccggtgt ctcttatcag accgtttccc gcgtggtgaa ccaggccagc cacgtttctg     120
cgaaaacgcg ggaaaaagtg aagcggcga tcaaagagct gggctacgtg ccgaaccgcg     180
cagcccgcac cctggtcacc cgacgtaccg acaccgtagc cctggtggtg tcggaaaaca     240
accagaagct cttcgccgaa cccttctatg ccgggatcgt gctcggcgtg ggggttgctc     300
tgtccgaacg gggattccag ttcgtcctgg ccacgggccg ctccgggata gagcatgagc     360
ggctgggcg ctacctggcc ggacagcacg tcgacgggg cctcctgctg tcgctccacc     420
gcgacgaccc gctgccgcag atgctggacg aggccggggt gccgtacgtc tacggcggcc     480
gtccgctcgg cgtccccgaa gaacaggtgt cctatgtcga tatcgacaac atcggcgggg     540
gacgccaggc cacccagcgg ctgatcgaga ccggcaccg gcggatcgct acgatcgcgg     600
gcccgcagga catggtcgct ggtgtggaac gcctccaggg gtatcgcgaa gcactgctcg     660
ccgcgggat ggagtacgac gagacgctgg tgagctacg tgacttcacc tacgacagcg     720
gggtggccgc gatgcgggag ctgctggatc ggcccccga cgtggacgcc gtgttcgcgg     780
cctccgactt gatgggctg gccgcgctgc gggtgctgcg tgcttcggga cgccgcgtgc     840
ccgaggatgt ggcggtggtc ggctacgacg actcgaccgt agccgagcac gccgaaccgc     900
```

```
cgatgaccag cgtcaaccag cccaccgagc tgatgggccg ggagatggcc cggctgctcg    960
tggaccggat caccggggag accaccgaac cggtgcggct ggtgctggag acccatttga   1020
tggtgcggga atccgggtga                                                1040

<210> SEQ ID NO 31
<211> LENGTH: 1124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
ctctagccat tttataggat cttaagatga aaaccaaacg cgtaactatc aaagatatcg     60
ccgaactggc gggcgtctcc aaagcgaccg ccagtctggt gctcaacggc cgtggcaaag    120
agctgcgcgt ggcgcaggag acgcgcgagc gcgtgctggc gatcatggcg gagctgaatt    180
acattcccaa ccgcgtggca caacaactgg cgggcaaaca gtcgttgctg attggcgttg    240
ccacctccag tctggccctg cacgcgccgt cgcaaattgt cgcggcgatt aaatctcgcg    300
ccgatcaact gggtgccagc gtggtggtgt cgatggtaga acgaagcggc gtcgaagcct    360
gtaaagcggc ggtgcacaat cttctcgcgc aacgcgtcag tgggctgatc attaactatc    420
cgctggatga ccaggatgcc attgctgtgg aagctgcctg cactaatgtt ccggcgttat    480
ttcttgatgt ctctgaccag acacccatca acagtattat tttctcccat gaagacggta    540
cgcgactggg cgtggagcat ctggtcgcat tgggtcacca gcaaatcgcg ctgttagcgg    600
gcccattaag ttctgtctcg gcgcgtctgc gtctggctgg ctggcataaa tatctcactc    660
gcaatcaaat tcagccgata gcggaacggg aaggcgactg gagtgccatg tccggttttc    720
aacaaaccat gcaaatgctg aatgagggca tcgttcccac tgcgatgctg gttgccaacg    780
atcagatggc gctgggcgca atgcgcgcca ttaccgagtc cgggctgcgc gttggtgcgg    840
atatctcggt agtgggatac gacgataccg aagacagctc atgttatatc ccgccgttaa    900
ccaccatcaa acaggatttt cgcctgctgg ggcaaaccag cgtggaccgc ttgctgcaac    960
tctctcaggg ccaggcggtg aagggcaatc agctgttgcc cgtctcactg gtgaaaagaa   1020
aaaccaccct ggcgcccaat acgcaaaccg cctctccccg cgcgttggcc gattcattaa   1080
tgcagctggc acgacaggtt tcccgactgg aaagcgggca gtga                    1124

<210> SEQ ID NO 32
<211> LENGTH: 1079
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
ggtcaagagt caagaggagg cttaagatga aaaccaaacg cgtaactatc aaagatatcg     60
ccgaactggc gggcgtctcc aaagcgaccg ccagtctggt gctcaacggc cgtggcaaag    120
agctgcgcgt ggcgcaggag acgcgcgagc gcgtgctggc gatcatggag tctcttagct    180
atcacccgaa cgccaacgcc cgtgcgctgg cgcagcagac cactgaaacg gtcggtctgg    240
tcgttggtga tgttttccgat ccgttttttcg gtgcaatggt gaaagcggtc gaacaggtgg    300
cttatcacac cggtaatttt ttattgattg gcaacggtta ccacaacgaa caaaagagc    360 gtcaggccat tgagcaactg atccgccatc gctgtgctgc gttggtcgtc catgccaaaa    420
```

```
tgatcccgga tgctgattta gcctcattaa tgaaacaaat gcccggtatg gtgctgatca    480
accgtatcct gcctggcttt gaaaaccgtt gtattgctct ggacgatcgt tacggtgcct    540
ggctggcaac gcgtcattta attcagcaag gtcatacccg cattggttat ctgtgctcta    600
accactctat ttctgacgcc gaagatcgtc tgcaaggggta ttacgatgcc cttgctgaaa   660
gtggtattgc ggccaatgac cggctggtga catttggcga accagacgaa agcggcggcg    720
aacaggcaat gaccgagctt ttgggacgag gaagaaattt cactgcgta gcctgttata    780 acgattcaat ggcggcgggt gcgatgggcg ttctcaatga taatggtatt gatgtaccgg    840
gtgagatttc gttaattggc tttgatgatg tgctggtgtc acgctatgtg cgtccgcgcc    900
tgaccaccgt gcgttaccca atcgtgacga tggcgaccca ggctgccgaa ctggctttgg    960
cgctggcgga taatcgccct ctcccggaaa tcactaatgt ctttagtccg acgctggtac   1020
gtcgtcattc agtgtcaact ccgtcgctgg aggcaagtca tcatgcaacc agcgactaa    1079
```

<210> SEQ ID NO 33
<211> LENGTH: 1055
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
ctctagccat tttataggat cttaagatga agacgaaacg cgtaaccatt aaagatatcg     60
cggaattagc tggggtgagt aaagcaacgg caagtcttgt tcttaatggt cgtggtaaag    120
aactgcgtgt cgcccaggaa acccgtgagc gcgtgctggc tattatcaaa gaactcggtt    180
acgtcccgaa tcgcgcggca cgcacattgg ttacacgccg cacggacacc gtggctttgg    240
tggtgtccga aaataaccag aaactgtttg cggaaccgtt ttatgcaggt atcgtgctgg    300
gtgtcggtgt ggctctgagt gaacgtggtt tccagttcgt cctggctacg ggtcgttcgg    360
gcattgagca cgaacgcctg gggggctatc tggcaggcca gcatgtggac ggcgtgctgc    420
ttcttagttt gcaccgcgac gatccgctgc cgcagatgct ggacgaagct ggagtaccgt    480
atgtatatgg tggccgcccg ctgggtgtgc cggaagagca ggtcagctat gtcgatatcg    540
acaatattgg tggcgggcgc caggctaccc agcgtctgat cgaaacgggt catcgtcgta    600
tcgcgactat tgccggcccg caagatatgg tggcaggagt agagcgtctg caaggatacc    660
gtgaggcatt attagccgcg ggcatggaat acgatgaaac attagtatca tatggtgact    720
ttacgtatga ttcgggcgtc gccgccatgc gcgaacttct ggaccgcgca ccggatgtgg    780
atgccgtatt cgcagcatct gatcttatgg ggctggcggc gttacgtgta ctgcgtgcat    840
cggggcgccg tgtgcctgaa gatgtcgcgg tcgttgggta cgacgattcg acggtggcgg    900
aacacgcgga accccccatg acgagcgtca ccagccgac agaattaatg ggtcgtgaga    960
tggctcgttt gcttgtagat cgtattacag gcgaaactac ggaaccggtt cgtttggtac   1020
tcgaaactca tttaatggtt cgcgaaagtg ggtaa                              1055
```

<210> SEQ ID NO 34
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
catttattaa accggtttat tgacataaac cggtttagca tagatactga gcacatcagc    60
aggacgcact gacccaattg ctcacaacca cgaaggaaca                         100

<210> SEQ ID NO 35
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
catttattaa accggtttat tgacataaac cggtttagca tagatactga gcacatcagc    60
aggacgcact gaccgaattc gtatctagga                                     90

<210> SEQ ID NO 36
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
ttattaaacc ggtttagcat tgacaattaa accggtttag cagatactga gcacatcagc    60
aggacgcact gacccaattg tcaggaatag gcccgtcgcc                         100

<210> SEQ ID NO 37
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ttattaaacc ggtttagcat tgacaattaa accggtttag cagatactga gcacatcagc    60
aggacgcact gaccgaattc cagttacagg tcac                                94

<210> SEQ ID NO 38
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
catttattaa accggtttat tgacataaac cggtttagca tagatactga gcacatcagc    60
aggacgcact gacccaattg tcaggaatag gcccgtcgcc                         100

<210> SEQ ID NO 39
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ttattaaacc ggtttagcat tgacaattaa accggtttag cagatactga gcacatcagc    60
aggacgcact gaccgaattc gtatctagga                              90

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tcaggaatag gcccgtcgcc                                         20

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
taccgataac gaccgaaag                                          19

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tggcacaacc taagtagggc                                         20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ctcacaacca cgaaggaaca                                         20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ctaaggatcg aacacgggag                                         20

<210> SEQ ID NO 45
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cagttacagg tcac                                               14

<210> SEQ ID NO 46
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gcggccgcga ctc                                                      13

<210> SEQ ID NO 47
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gacgcaaaag gcaa                                                     14

<210> SEQ ID NO 48
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ggtcggtctt cggg                                                     14

<210> SEQ ID NO 49
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gtatctagga                                                          10

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ggcgcaacca agtcctaggt                                               20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ctctagccat tttataggat                                               20

-continued

```
<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gggccgcatt aggagggtac                                                   20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ggtcaagagt caagaggagg                                                   20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
acttacttat aataaggagg                                                   20

<210> SEQ ID NO 55
<211> LENGTH: 70
<212> TYPE: PRT
<213> ORGANISM: Escherichia coli

<400> SEQUENCE: 55

Met Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
        35                  40                  45

Pro Asn Arg Val Ala Gln Gln Leu Ala Gly Lys Gln Ser Leu Leu Ile
    50                  55                  60

Gly Val Ala Thr Ser Ser
65                  70

<210> SEQ ID NO 56
<211> LENGTH: 68
<212> TYPE: PRT
<213> ORGANISM: Escherichia coli

<400> SEQUENCE: 56

Met Ala Thr Ile Lys Asp Val Ala Arg Leu Ala Gly Val Ser Val Ala
1               5                   10                  15

Thr Val Ser Arg Val Ile Asn Asn Ser Pro Lys Ala Ser Glu Ala Ser
            20                  25                  30

Arg Leu Ala Val His Ser Ala Met Glu Ser Leu Ser Tyr His Pro Asn
        35                  40                  45
```

```
Ala Asn Ala Arg Ala Leu Ala Gln Gln Thr Thr Glu Thr Val Gly Leu
    50                  55                  60

Val Val Gly Asp
65

<210> SEQ ID NO 57
<211> LENGTH: 68
<212> TYPE: PRT
<213> ORGANISM: Escherichia coli

<400> SEQUENCE: 57

Met Ala Thr Ile Lys Asp Val Ala Lys Arg Ala Asn Val Ser Thr Thr
1               5                   10                  15

Thr Val Ser His Val Ile Asn Lys Thr Arg Phe Val Ala Glu Glu Thr
                20                  25                  30

Arg Asn Ala Val Trp Ala Ala Ile Lys Glu Leu His Tyr Ser Pro Ser
            35                  40                  45

Ala Val Ala Arg Ser Leu Lys Val Asn His Thr Lys Ser Ile Gly Leu
        50                  55                  60

Leu Ala Thr Ser
65

<210> SEQ ID NO 58
<211> LENGTH: 75
<212> TYPE: PRT
<213> ORGANISM: Klebsiella pneumoniae

<400> SEQUENCE: 58

Met Lys Thr Lys Arg Val Thr Ile Lys Asp Ile Ala Glu Leu Ala Gly
1               5                   10                  15

Val Ser Lys Ala Thr Ala Ser Leu Val Leu Asn Gly Arg Gly Lys Glu
                20                  25                  30

Leu Arg Val Ala Gln Glu Thr Arg Glu Arg Val Leu Ala Ile Ala Arg
            35                  40                  45

Glu Gln His Tyr Gln Pro Ser Ile His Ala Arg Ser Leu Arg Asp Asn
        50                  55                  60

Arg Ser His Thr Ile Gly Leu Val Val Pro Glu
65                  70                  75

<210> SEQ ID NO 59
<211> LENGTH: 73
<212> TYPE: PRT
<213> ORGANISM: Thermobifida fusca

<400> SEQUENCE: 59

Met Glu Arg Arg Arg Pro Thr Leu Glu Met Val Ala Ala Leu Ala
1               5                   10                  15

Gly Val Gly Arg Gly Thr Val Ser Arg Val Ile Asn Gly Ser Asp Gln
                20                  25                  30

Val Ser Pro Ala Thr Arg Glu Ala Val Lys Arg Ala Ile Lys Glu Leu
            35                  40                  45

Gly Tyr Val Pro Asn Arg Ala Ala Arg Thr Leu Val Thr Arg Arg Thr
        50                  55                  60

Asp Thr Val Ala Leu Val Val Ser Glu
65                  70

<210> SEQ ID NO 60
<211> LENGTH: 68
<212> TYPE: PRT
```

<213> ORGANISM: Escherichia coli

<400> SEQUENCE: 60

Met Ile Thr Ile Arg Asp Val Ala Arg Gln Ala Gly Val Ser Val Ala
1               5                   10                  15

Thr Val Ser Arg Val Leu Asn Asn Ser Thr Leu Val Ser Ala Asp Thr
            20                  25                  30

Arg Glu Ala Val Met Lys Ala Val Ser Glu Leu Asp Tyr Arg Pro Asn
        35                  40                  45

Ala Asn Ala Gln Ala Leu Ala Thr Gln Val Ser Asp Thr Ile Gly Val
    50                  55                  60

Val Val Met Asp
65

<210> SEQ ID NO 61
<211> LENGTH: 69
<212> TYPE: PRT
<213> ORGANISM: Escherichia coli

<400> SEQUENCE: 61

Met Met Thr Thr Met Leu Glu Val Ala Lys Arg Ala Gly Val Ser Lys
1               5                   10                  15

Ala Thr Val Ser Arg Val Leu Ser Gly Asn Gly Tyr Val Ser Gln Glu
            20                  25                  30

Thr Lys Asp Arg Val Phe Gln Ala Val Glu Glu Ser Gly Tyr Arg Pro
        35                  40                  45

Asn Leu Leu Ala Arg Asn Leu Ser Ala Lys Ser Thr Gln Thr Leu Gly
    50                  55                  60

Leu Val Val Thr Asn
65

<210> SEQ ID NO 62
<211> LENGTH: 68
<212> TYPE: PRT
<213> ORGANISM: Escherichia coli

<400> SEQUENCE: 62

Met Ala Thr Met Lys Asp Val Ala Arg Leu Ala Gly Val Ser Thr Ser
1               5                   10                  15

Thr Val Ser His Val Ile Asn Lys Asp Arg Phe Val Ser Glu Ala Ile
            20                  25                  30

Thr Ala Lys Val Glu Ala Ala Ile Lys Glu Leu Asn Tyr Ala Pro Ser
        35                  40                  45

Ala Leu Ala Arg Ser Leu Lys Leu Asn Gln Thr His Thr Ile Gly Met
    50                  55                  60

Leu Ile Thr Ala
65

<210> SEQ ID NO 63
<211> LENGTH: 68
<212> TYPE: PRT
<213> ORGANISM: Vibrio alginolyticus

<400> SEQUENCE: 63

Met Ala Ser Leu His Asp Val Ala Arg Leu Ala Gly Val Ser Lys Ser
1               5                   10                  15

Thr Val Ser Arg Val Ile Asn Asp Glu Tyr Gly Val Lys Glu Ala Thr
            20                  25                  30

```
Lys Gln Lys Val Arg Gln Ala Val Ala Glu Cys Gly Tyr Val Pro Asn
            35                  40                  45

Gln Val Ala Lys Asp Leu Lys Ser Gln Lys Thr Asn Leu Val Gly Val
 50                  55                  60

Ile Val Pro Arg
 65

<210> SEQ ID NO 64
<211> LENGTH: 72
<212> TYPE: PRT
<213> ORGANISM: Escherichia coli

<400> SEQUENCE: 64

Met Lys Lys Lys Arg Pro Val Leu Gln Asp Val Ala Asp Arg Val Gly
  1               5                  10                  15

Val Thr Lys Met Thr Val Ser Arg Phe Leu Arg Asn Pro Glu Gln Val
                 20                  25                  30

Ser Val Ala Leu Arg Gly Lys Ile Ala Ala Leu Asp Glu Leu Gly
            35                  40                  45

Tyr Ile Pro Asn Arg Ala Pro Asp Ile Leu Ser Asn Ala Thr Ser Arg
 50                  55                  60

Ala Ile Gly Val Leu Leu Pro Ser
 65                  70

<210> SEQ ID NO 65
<211> LENGTH: 73
<212> TYPE: PRT
<213> ORGANISM: Escherichia coli

<400> SEQUENCE: 65

Met Ala Thr Ala Lys Lys Ile Thr Ile His Asp Val Ala Leu Ala Ala
  1               5                  10                  15

Gly Val Ser Val Ser Thr Val Ser Leu Val Leu Ser Gly Lys Gly Arg
                 20                  25                  30

Ile Ser Thr Ala Thr Gly Glu Arg Val Asn Ala Ala Ile Glu Glu Leu
            35                  40                  45

Gly Phe Val Arg Asn Arg Gln Ala Ser Ala Leu Arg Gly Gly Gln Ser
 50                  55                  60

Gly Val Ile Gly Leu Ile Val Arg Asp
 65                  70

<210> SEQ ID NO 66
<211> LENGTH: 15
<212> TYPE: PRT
<213> ORGANISM: Escherichia coli

<400> SEQUENCE: 66

Thr Arg Glu Lys Val Glu Ala Ala Met Ala Glu Leu Asn Tyr Ile
  1               5                  10                  15

<210> SEQ ID NO 67
<211> LENGTH: 15
<212> TYPE: PRT
<213> ORGANISM: Escherichia coli

<400> SEQUENCE: 67

Ser Arg Leu Ala Val His Ser Ala Met Glu Ser Leu Ser Tyr His
  1               5                  10                  15

<210> SEQ ID NO 68
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ttgacaattg tgagcgctca caagatact                                        29

<210> SEQ ID NO 69
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ttattaaacc ggtttagcat tgacaattaa accggtttag cagatact                   48

<210> SEQ ID NO 70
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ttattaaacc ggtttattga cataaaccgg tttagcagat act                        43
```